United States Patent
Xia et al.

(10) Patent No.: US 10,918,645 B2
(45) Date of Patent: Feb. 16, 2021

(54) SUBSTITUTED TRICYCLIC HETEROCYCLIC COMPOUNDS AND USE THEREOF

(71) Applicants: LIFEARC, London (GB); SUZHOU YABAO PHARMACEUTICAL R&D CO., LTD., Jiangsu (CN)

(72) Inventors: Yan Xia, Jiangsu (CN); Edward Giles McIver, London (GB); Yang Song, Jiangsu (CN); Yuanyuan Xu, Jiangsu (CN); Lin Zhu, Jiangsu (CN); Chunjun Chu, Jiangsu (CN); Ling Wu, Jiangsu (CN); Miao Liu, Jiangsu (CN); Justin Stephen Bryans, London (GB)

(73) Assignees: LIFEARC, London (GB); SUZHOU YABAO PHARMACEUTICAL R&D CO., LTD., Suzhou (CN)

( * ) Notice: Subject to any disclaimer, the term of this patent is extended or adjusted under 35 U.S.C. 154(b) by 0 days.

(21) Appl. No.: 16/309,227

(22) PCT Filed: Jun. 13, 2017

(86) PCT No.: PCT/CN2017/088137
§ 371 (c)(1),
(2) Date: Dec. 12, 2018

(87) PCT Pub. No.: WO2017/215600
PCT Pub. Date: Dec. 21, 2017

(65) Prior Publication Data
US 2019/0307763 A1 Oct. 10, 2019

Related U.S. Application Data

(63) Continuation of application No. PCT/CN2016/089365, filed on Jul. 8, 2016, which is a continuation of application No. PCT/CN2016/085811, filed on Jun. 15, 2016.

(51) Int. Cl.
| | |
|---|---|
| *C07D 471/14* | (2006.01) |
| *C07D 471/22* | (2006.01) |
| *C07D 487/16* | (2006.01) |
| *A61K 31/55* | (2006.01) |
| *A61P 25/00* | (2006.01) |
| *A61P 35/00* | (2006.01) |

(52) U.S. Cl.
CPC ............ *A61K 31/55* (2013.01); *A61P 25/00* (2018.01); *A61P 35/00* (2018.01); *C07D 471/14* (2013.01); *C07D 471/22* (2013.01)

(58) Field of Classification Search
CPC ... C07D 487/16; C07D 471/22; C07D 487/22
See application file for complete search history.

(56) References Cited

FOREIGN PATENT DOCUMENTS

| | | |
|---|---|---|
| EP | 1479670 A1 | 11/2004 |
| WO | 2010106333 A1 | 9/2010 |
| WO | 2012038743 A1 | 3/2012 |
| WO | 2013139882 A1 | 9/2013 |
| WO | 2013164323 A1 | 11/2013 |
| WO | 2017215600 A1 | 12/2017 |

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Testa et al. Pure Appl. Chem. vol. 76, pp. 907-914 (2004).*
Zimprich et al. (2004) "Mutations in LRRK2 Cause Autosomal-Dominant Parkinsonism with Pleomorphic Pathology," Neuron, 44:601-607.
Bu et al. (2002) "Synthesis and cytotoxicity of potential anticancer derivatives of pyrazolo[3,4,5,kl]acridine and indolo [2,3-a]acridine," Tetrahedron, 58:175-181.
Agalliu et al. (2015) "Higher frequency of certain cancers in LRRK2 G2019S mutation carriers with Parkinson's disease: A pooled analysis," JAMA Neurol., 72(1):58-65.
Bailey et al. (2013) "LRRK2 phosporylates novel tau epitopes and promotes tauopathy," Acta Neuropathol., 126:809-827.
Brand et al. (1993) "Targeted gene expression as a means of altering cell fates and generating dominant phenotypes," Development, 118:401-415.

(Continued)

*Primary Examiner* — Emily A Bernhardt
(74) *Attorney, Agent, or Firm* — Brian C. Trinque; Lathrop GPM LLP

(57) ABSTRACT

Provided are a substituted tricyclic heterocyclic compound of formula I or a stereoisomer, a tautomer, an N-oxide, a hydrate, a solvate, a metabolite, a pharmaceutically acceptable salt, ester or a prodrug thereof, a pharmaceutical composition including the same and uses thereof. The substituted tricyclic heterocyclic compounds and the pharmaceutical compositions comprising the compounds disclosed herein can be used for treating a disorder caused by at least one of cancer and neurodegenerative diseases. Further the compounds and the pharmaceutical compositions comprising the compounds disclosed herein can be also used for preventing or treating a disorder caused by, associated with or accompanied by any abnormal kinase activity.

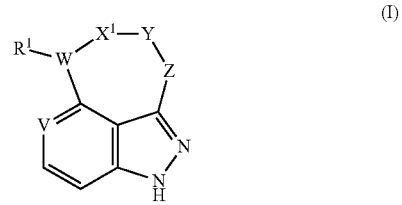

(I)

9 Claims, No Drawings

(56) References Cited

OTHER PUBLICATIONS

Di Fonzo et al. (2006) "A common missense variant in the LRRK2 gene, Gly2385Arg, associated with Parkinson's disease risk in Taiwan," Neurogenetics, 7:133-138.
Farrer et al. (2007) "Lrrk2 G2385R is an ancestral risk factor for Parkinson's disease in Asia," Parkinsonism and Related Disorders, 13:89-92.
Gennaro, A. R., (1985) Remington's Pharmaceutical Sciences, 17th Edition, (9 pages).
Goedert et al. (2005) "Mutations causing neurodegenerative tauopathies,"Biochimica et Biophysica Acta, 1739:240-250.
Greggio et al. (2006) "Kinase activity is requried for the toxic effects of mutant LRRK2/dardarin," Neurobiology of Disease, 23:329-341.
Heo et al. (2010) "LRRK2 enhances oxidative stress-induced neurotoxicity via its kinase activity," Experimental Cell Research, 316:649-656.
Ishihara et al. (2007) "Screening for Lrrk2 G2019S and Clinical Comparison of Tunisian and North American Caucasian Parkinson's Disease Families," Movement Disorders, 22(1):55-61.
Jaleel et al. (2007) "LRRK2 phosphorylates moesin at threonine-558: characterization of how Parkinson's disease mutants affect kinase activity," Biochem. J., 405:307-317.
Jostins et al. (2012) "Host-microbe interactions have shaped the genetic architecture of inflammatory bowel disease," Nature, 491(7422):119-124.
Kachergus et al. (2005) "Identification of a novel LRRK2 mutation linked to autosomal dominant Parkinsonism: evidence of a common founder across European populations," Am. J. Hum. Genet., 76:672-680.
Kawamaki et al. (2012) "LRRK2 phosphorylates tubulin-associated tau but not the free molecule: LRRK2-mediated regulation of the tau-tubulin association and neurite outgrowth," PLoS ONE, 7(1):30834, 9 pages.
Khan et al. (2005) "Mutations in the gene LRRK2 encoding dardarin (PARK8) cause familial Parkinson's disease: clinical, pathological, olfactory and functional imaging and genetic data," Brain, 128:2786-2796.
Lees et al. (2009) "Parkinson's disease," The Lancet, 373:2055-2066.
Li et al. (2009) "Mutant LRRK2 R1441G BAC transgenic mice recapitulate cardinal features of Parkinson's disease," Nat. Neurosci., 12(7):826-828.
Li et al. (2010) "Autophagy Dysfunction in Alzheimer's Disease," Neurodegenerative Dis, 7:265-271.
Liu et al. (2008) "A *Drosophila* model for LRRK2-linked parkinsonism," PNAS, 105(7):2693-2698.
Liu et al. (2011) "Inhibitors of LRRK2 kinase attenuate neurodegeneration and Parkinson-like phenotypes in Caenorhabditis elegans and *Drosophila* Parkinson's disease models," Human Molecular Genetics, 20(20):3933-3942.
Manzoni et al. (2013) "Dysfunction of the autophagy/lysomal degradation pathway is a shared feature of the genetic synucleinopathies," The FASEB Journal, 27:3424-3429.
Manzoni et al. (2013) "Inhibition of LRRK2 kinase activity stimulates macroautophagy," Biochim Biophys Acta, 1833(12):2900-2910.
March (1985) Advanced Organic Chemistry, Third Edition, (5 pages).
Marcinek et al. (2013) "LRRK2 and RIPK2 variants in the NOD 2-mediated signaling pathway are associated with susceptibility to *Mycobacterium leprae* in Indian populations," PLoS ONE, 8(8):e73103, 6 pages.
Marin. Ignacio (2006) "The Parkinson Disease Gene LRRK2: Evolutionary and Structural Insights," Mol. Biol. Evol., 23(12):2423-2433.

Mata et al. (2006) "LRRK2 in Parkinson's disease: protein domains and functional insights," TRENDS in Neurosciences, 29(5):286-293.
Nalls et al. (2014) "Large-scale meta-analysis of genome-wide association data identifies six new risk loci for Parkinson's disease," Nat. Genet., 46(9):989-993.
Nxon et al. (2013) "The role of autophagy in neurodegenerative disease," Nature Medicine, 19(8):983-997.
Orenstein et al. (2013) "Interplay of LRRK2 with chaperone-mediated autophagy," Nat. Neurosci., 16(4):394-406.
Ozelius et al. (2006) "LRRK2 G2019S as a Cause of Parkinson's Disease in Ashkenazi Jews," The New England Journal of Medicine, 354(4):424-425.
Paisan-Ruiz et al. (2004) "Cloning of the Gene Containing Mutations that Cause PARK8-Linked Parkinson's Disease," Neuron, 44:595-600.
Reddy et al. (2006) "Clues to Neuro-Degeneration in Niemann-Pick Type C Disease from Global Gene Expression Profiling," PLoS ONE, 1:e19, 7 pages.
Reinhardt et al. (2013) "Genetic Correction of a LRRK2 Mutation in Human iPSCs Links Parkinsonian Neurodegeneration to ERK-Dependent Changes in Gene Expression," Cell Stem Cell, 12:354-367.
Ross et al. (2008) "Analysis of Lrrk2 R1628P as a Risk Factor for Parkinson's Disease," Ann. Neurol., 64:88-96.
Ross et al. (2011) "LRRK2 exonic variants and susceptibility to Parkinson's disease," Lancet Neurol., 10(10):898-908.
Rothman et al. (2008) "Dopamine/serotonin releasers as medications for stimulant addictions," Progress in Brain Research, 172:385-406.
Rudenko et al. (2012) "The G2385R Variant of Leucine-Rich Repeat Kinase 2 Associated with Parkinson's Disease is a Partial Loss of Function Mutation," Biochem J., 446(1):99-111.
Rudenko et al. (2014) "Heterogeneity of Leucine-Rich Repeat Kinase 2 Mutations: Genetics, Mechanishms and Therapeutic Implications," Neurotherapeutics, 11:738-750.
Sanders et al. (2014) "LRRK2 mutations cause mitochondrial DNA damage in iPSC-derived neural cells from Parkinson's disease patients: Reversal by gene correction," Neurobiol. Dis., vol. 62, 13 pages.
Satake et al. (2009) "Genome-wide association study identifies common variants at four loci as genetic risk factors for Parkinson's disease," Nature Genetics, 41(12):1303-1307.
Simon-Sanchez et al. (2009) "Genome-Wide Association Study reveals genetic risk underlying Parkinson's disease," Nat. Genet., 41(12):1308-1312.
Singleton et al. (2013) "The genetics of Parkinson's disease: progress and therapeutic implications," Mov. Disord., 28(1)14-23.
Swan et al. (2013) "The association between beta-glucocerebrosidase mutations and parkinsonism," Curr. Neurol. Neurosci. Rep., 13(8):16 pages.
Tan et al. (2006) "Identification of a common Genetic Risk Variant (LRRK2 Gly2385Arg) in Parkinson's Disease," Ann. Acad. Med Singapore, 35:840-842.
Taylor et al. (2006) "LRRK2: a common pathway for parkinsonism, pathogens and prevention," TRENDS in Molecular Medicine, 12(2):76-82.
Taymans et al. (2010) "Mechanisms in dominant parkinsonism: The toxic triangle of LRRK2, alpha-synuclein and tau," Bioessays, 32(3):227-235.
Wade et al. (1994) Handbook of Pharmaceutical Excipients, Second Edition, (2 pages).
West et al. (2005) "Parkinson's disease-associated mutations in leucine-rich repeat kinase 2 augment kinase activity," PNAS, 102(46):16842-16847.
Westbroek et al. (2011) "Exploring the link between glucocerebroside mutations and parkinsonism," Trends in Mol. Med., 17(9):485-493.
Wuts, P. and Greene, T. (2007) "Greene's Protective Groups in Organic Synthesis," Fourth Edition, (5 pages).

\* cited by examiner

SUBSTITUTED TRICYCLIC HETEROCYCLIC COMPOUNDS AND USE THEREOF

RELATED APPLICATIONS

This application is a 35 U.S.C. § 371 filing of International Application No. PCT/CN2017/088137, filed on Jun. 13, 2017, which claims priority and benefits of International Patent Application No. PCT/CN2016/085811, filed with State Intellectual Property Office on Jun. 15, 2016, and International Application No. PCT/CN2016/089365, filed on Jul. 8, 2016. The entire contents of which is are incorporated herein by reference.

FIELD OF THE INVENTION

The present invention belongs to the field of pharmaceutical technology, and more specifically relates to a compound, a composition including the same and uses thereof for treating a disorder caused by cancer and neurodegenerative diseases. Particularly, provided herein are substituted tricyclic heterocyclic compounds capable of inhibiting one or more kinases, particularly, LRRK, more particularly, LRRK2.

BACKGROUND OF THE INVENTION

Parkinson's disease (PD) is the second most common neurodegenerative disease, affecting 1-2% of the elderly population [1]. Genome-wide association studies (GWAS) have related 28 genetic risk variants at 24 loci with non-familial PD [2]. Among those, mutations in LRRK2 (Park8) are also found in hereditary forms, pinpointing a shared molecular pathway driving pathogenesis in both familial and non-familial PD and comprising the most common cause of the disease [3, 4]. PD pathogenic LRRK2 mutations map is predominantly related to the kinase (G2019S, I2020T) and the ROC-COR domains (R1441C/G/H, Y1699C), implying that these enzymatic activities are crucial for pathogenesis [5]. The frequency of the pathogenic mutations is rare at around 2% overall [6, 7], however the most common mutation G2019S is found in up to 40% of patients in certain ethnic populations, which activates the kinase two to three fold [8-13]. In addition to pathogenic mutations, common genetic variability in LRRK2 is a risk factor for sporadic PD [14-16].

In 2004, LRRK2 was identified as the gene responsible for PD inheritance associated with the PARK8 locus [17, 18] and was found to be comprised of 51 exons, giving rise to a large (268 kDa) protein. Subsequently, many variants in LRRK2 primary structure have been identified, including dominant mutations segregating with familial PD that also occur in sporadic PD [19], together with polymorphisms at the LRRK2 locus that increase the lifetime risk for the development of sporadic PD [20-22].

LRRK2 is a multidomain protein encompassing two enzymatic functions at its core. The GTPase domain, comprising of Ras of complex protein (ROC) terminating with a spacer domain called the C-terminal of the Roc-domain (COR), is immediately followed by the kinase domain, belonging to the serine/threonine kinases. This enzymatic core is surrounded by protein-protein interaction domains comprising the armadillo, ankyrin and leucine-rich repeat (LRR) domains at the LRRK2 N terminus [23]. The LRRK2 C terminus harbours the WD40 domain, which is deemed essential for protein folding, thus controlling LRRK2 function and kinase activity [24]. Interestingly, the dominant, pathogenic mutations described up to date, occur within the enzymatic core of LRRK2, suggesting that modification of LRRK2 activity greatly impacts PD onset and progression.

To date, almost 40 single amino acid substitution mutations have been linked to autosomal-dominant PD [25, 26]. The most prevalent mutant form of LRRK2 accounting for approximately 6% of familial PD and 3% of sporadic PD cases in Europe, comprises an amino acid substitution of Gly2019 to a Ser residue. Gly2019 is located within the conserved DYG-$Mg^{2+}$-binding motif, in subdomain-VII of the kinase domain [25]. Recent reports suggest that this mutation enhances the autophosphorylation of LRRK2, as well as its ability to phosphorylate myelin basic protein by 2-3 folds [8, 12, 27]. Cellular toxicity, in both the absence and presence of oxidative stress, and the formation of inclusion bodies were observed when overexpressing G2019S-LRRK2 in cell lines and primary neuronal cultures [27, 28]. These results, and the fact that genetic inactivation of LRRK2 kinase activity showed a protective effect against such a toxic phenotype, suggest that an alteration in LRRK2 kinase activity is potentially involved in the neurotoxic and pathogenic mechanisms of LRRK2-PD.

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors with LRRK2 kinase activity [29]. Increased mitochondrial damage associated with LRRK2 G2019S mutation in iPSCs is also blocked by genetic correction of the G2019S mutation [30].

Additional evidence links LRRK2 function and dysfunction with autophagy-lysosomal pathways [31]. LRRK2 proteins confer defects in chaperone-mediated autophagy that negatively impact the ability of cells to degrade alpha-synuclein [32]. In other cell models, selective LRRK2 inhibitors have been shown to stimulate macroautophagy [33]. These data suggest that small molecule inhibitors with LRRK2 kinase activity may be effective in the treatment of diseases characterized by defects in cellular proteostasis that result from aberrant autophagy/lysosomal degradation pathways including forms of Parkinson's disease associated with GBA mutations [34], other alpha-synucleinopathies, tauopathies, Alzheimer's disease [35] and other neurodegenerative diseases [36] and Gaucher disease [37]. Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders [38]. This observation suggests that LRRK2 inhibitors may be effective in the treatment of NPC.

The PD-associated G2019S mutant form of LRRK2 has also been reported to enhance phosphorylation of tubulin-associated Tau [39], and disease models have been proposed in which LRRK2 acts upstream of the pathogenic effects of Tau and alpha-synuclein [40]. In support of this, LRRK2 expression has been associated with increased aggregation of insoluble Tau, and increased Tau phosphorylation, in a transgenic mouse model [41]. Over-expression of the PD pathogenic mutant protein LRRK2 R1441G is reported to cause symptoms of Parkinson's disease and hyperphosphorylation of Tau in transgenic mouse models [42]. Therefore, these data suggest that LRRK2 inhibitors with kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) [43]. In addition, LRRK2 inhibitors may have utility in treatment of other diseases characterized by diminished dopamine levels such as withdrawal symptoms/relapse associated with drug addiction [44].

SUMMARY OF THE INVENTION

In one aspect, provided herein is a compound of formula I, or a stereoisomer, a tautomer, an N-oxide, a hydrate, a solvate, a metabolite, a pharmaceutically acceptable salt, ester or a prodrug thereof:

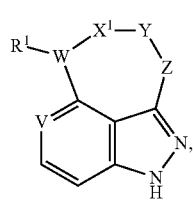

(I)

Wherein:

V is CH or N;

W is N or O;

$R^1$ is absent, H, $C_{1-10}$ alkyl, $C_{3-10}$ cycloalkyl, $C_{2-10}$ heterocycloalkyl, $C_{6-14}$ aryl, $C_{1-10}$ heteroaryl, $C_{1-5}$ alkyl-$C_{1-10}$ heteroaryl, or $C_{1-5}$ alkyl-$C_{6-14}$ aryl, wherein each of said $C_{1-10}$ alkyl, $C_{3-10}$ cycloalkyl, $C_{2-10}$ heterocycloalkyl, $C_{6-14}$ aryl, $C_{1-10}$ heteroaryl, $C_{1-5}$ alkyl-$C_{1-10}$ heteroaryl and $C_{1-5}$ alkyl-$C_{6-14}$ aryl is independently and optionally substituted with one or more substituents chosen from F, Cl, Br, I, —$NO_2$, —CN, —$N_3$, —$NH_2$, —OH, $C_{1-6}$ alkyl, $C_{3-7}$ cycloalkyl, and $C_{2-7}$ heterocycloalkyl;

$X^1$ is a bond, CO, or —$(CH_2)_n$—;

Y is —$(CH_2)_n$—, —$(CR^2R^3)$—, $C_{6-14}$ aryl or $C_{1-10}$ heteroaryl, optionally $R^2$ and $R^3$ together with the carbon atom to which they are attached, form a $C_3$-$C_{10}$ carbocyclic ring or a 3- to 10-membered heterocyclic ring, wherein each of said —$(CH_2)_n$—, —$(CR^2R^3)$—, $C_{6-14}$ aryl, $C_{1-10}$ heteroaryl, $C_3$-$C_{10}$ carbocyclic ring and 3- to 10-membered heterocyclic ring is independently and optionally substituted with one or more substituents chosen from $C_{1-6}$ alkyl, $C_{3-7}$ cycloalkyl, $C_{3-7}$ heterocycloalkyl, F, Cl, Br, I, —$NO_2$, —CN, —$N_3$, —$NH_2$, —OH, and $C_{1-6}$ haloalkyl;

Z is a bond, $NR^2$, —$(CH_2)_n$— or —$(CR^2R^3)$—, wherein each of said $NR^2$, —$(CH_2)_n$— and —$(CR^2R^3)$— is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl;

n is 0, 1, 2, 3, 4 or 5;

$R^2$ and $R^3$ are independently selected from —H, $C_{1-6}$ alkyl, $C_{3-7}$ cycloalkyl, $C_{2-7}$ heterocycloalkyl, $C_{6-14}$ aryl or $C_{1-10}$ heteroaryl, wherein each of said $C_{1-6}$ alkyl, $C_{3-7}$ cycloalkyl, $C_{2-7}$ heterocycloalkyl, $C_{6-14}$ aryl and $C_{1-10}$ heteroaryl is optionally and independently substituted with one or more substituents chosen from F, Cl, Br, I, —$NO_2$, —CN, —$N_3$, —$NH_2$, —OH, and —$CO_2H$.

In some embodiments, $R^1$ is H, $C_{1-6}$ alkyl, $C_{3-7}$ cycloalkyl, $C_{3-7}$ heterocycloalkyl, $C_{6-10}$ aryl, $C_{3-8}$ heteroaryl, $C_{1-3}$ alkyl-$C_{1-7}$ heteroaryl, or $C_{1-3}$-alkyl-$C_{6-10}$ aryl, wherein each of said $C_{1-6}$ alkyl, $C_{3-7}$ cycloalkyl, $C_{3-7}$ heterocycloalkyl, $C_{6-10}$ aryl, $C_{3-8}$ heteroaryl, $C_{1-3}$ alkyl-$C_{1-7}$ heteroaryl, and $C_{1-3}$ alkyl-$C_{6-10}$ aryl is independently and optionally substituted with one or more substituents chosen from F, Cl, Br, I, —$NO_2$, —CN, —$N_3$, —$NH_2$, —OH, $C_{1-6}$ alkyl, $C_{3-7}$ cycloalkyl, and $C_{3-7}$ heterocycloalkyl.

In some embodiments, $X^1$ is CO, —$CH_2$—, —$(CH_2)_2$—, or —$(CH_2)_3$—.

In some embodiments, Y is —$CH_2$—, —$(CH_2)_2$—, —$(CH_2)_3$—, —$(CR^2R^3)$—, $C_{6-10}$ aryl or $C_{3-8}$ heteroaryl, optionally $R^2$ and $R^3$ together with the carbon atom to which they are attached, form a $C_3$-$C_8$ carbocyclic ring or a 3- to 8-membered heterocyclic ring, wherein each of said —$CH_2$—, —$(CH_2)_2$—, —$(CH_2)_3$—, —$(CR^2R^3)$—, $C_{6-10}$ aryl, $C_{3-8}$ heteroaryl, $C_3$-$C_8$ carbocyclic ring and 3- to 8-membered heterocyclic ring is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl.

In some embodiments, Y is —$CH_2$—, —$(CH_2)_2$—, —$(CH_2)_3$—, —$(CR^2R^3)$—,

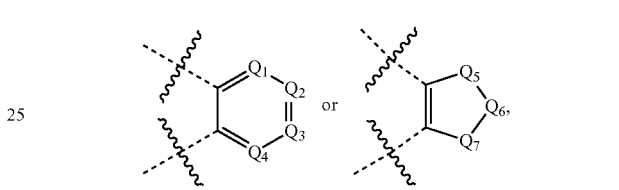

wherein each of $Q_1$, $Q_2$, $Q_3$ and $Q_4$ is independently C or N, and each of $Q_1$, $Q_2$, $Q_3$ and $Q_4$ is optionally substituted with one or more substituents chosen from $C_{1-6}$ alkyl, $C_{3-7}$ cycloalkyl, $C_{3-7}$ heterocycloalkyl, F, Cl, Br, I, —$NO_2$, —CN, —$N_3$, —$NH_2$, —OH, $C_{1-6}$ alkyl and $C_{1-6}$ haloalkyl, wherein each of $Q_5$, $Q_6$ and $Q_7$ is independently C, N, O or S, and each of $Q_5$, $Q_6$ and $Q_7$ is optionally substituted with one or more substituents chosen from $C_{1-6}$ alkyl, $C_{3-7}$ cycloalkyl, $C_{3-7}$ heterocycloalkyl, F, Cl, Br, I, —$NO_2$, —CN, —$N_3$, —$NH_2$, —OH, $C_{1-6}$ alkyl or $C_{1-6}$ haloalkyl.

In some embodiments, Z is a bond, $NR^2$, —$CH_2$—, —$(CH_2)_2$—, —$(CH_2)_3$— or —$(CR^2R^3)$—, wherein each of said $NR^2$, —$CH_2$—, —$(CH_2)_2$—, —$(CH_2)_3$— and —$(CR^2R^3)$— is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl.

In some embodiments, $R^2$ and $R^3$ are independently selected from —H, $C_{1-3}$ alkyl, $C_{3-5}$ cycloalkyl, $C_{3-5}$ heterocycloalkyl, $C_{6-8}$ aryl or $C_{3-8}$ heteroaryl, wherein each of said $C_{1-3}$-alkyl, $C_{3-5}$ cycloalkyl, $C_{3-5}$ heterocycloalkyl, $C_{6-8}$ aryl and $C_{3-8}$ heteroaryl is optionally and independently substituted one or more substituents chosen from F, Cl, Br, I, —$NO_2$, —CN, —$N_3$, —$NH_2$, —OH, and —$CO_2H$.

In some embodiments, $R^1$ is selected from the following groups:

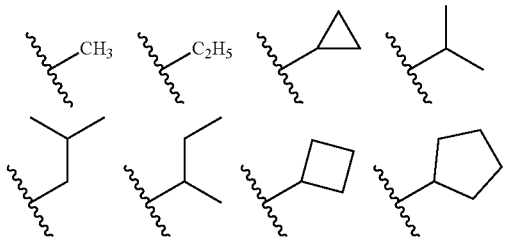

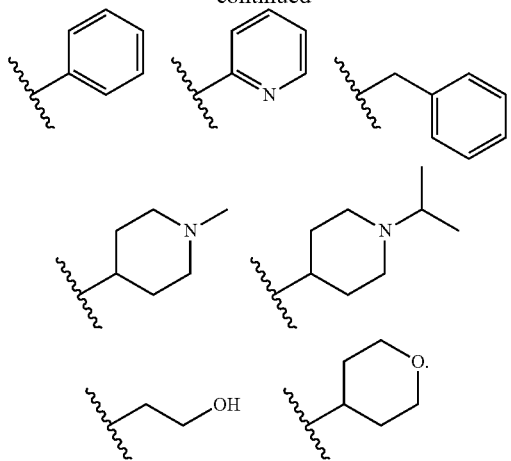

In some embodiments, R¹ is preferably selected from the following groups:

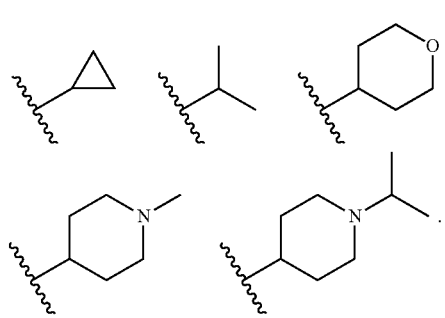

In some embodiments, Y is —CH₂—, —(CH₂)₂—, —(CH₂)₃—, —(CR²R³)—, a benzene ring, a 5- to 6-membered heteroaromatic ring, $C_{6-10}$ aryl or $C_{3-8}$ heteroaryl, optionally R² and R³ together with the carbon atom to which they are attached, form a $C_3$-$C_6$ carbocyclic ring or a 3- to 6-membered heterocyclic ring, wherein each of said benzene ring, a 5- to 6-membered heteroaromatic ring, $C_{6-10}$ aryl, $C_{3-8}$ heteroaryl, $C_3$-$C_6$ carbocyclic ring and 3- to 6-membered heterocyclic ring is independently and optionally substituted with one or more substituents chosen from F, Cl, Br, I, —NO₂, —CN, —N₃, —NH₂, —OH, methyl, ethyl, n-propyl, isopropyl, —CF₃, and $C_{1-3}$ haloalkyl.

In some embodiments, Y is selected from the following groups:

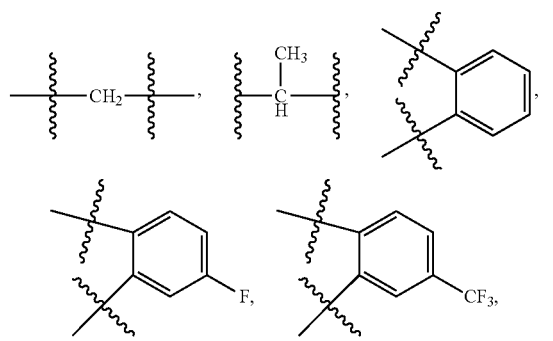

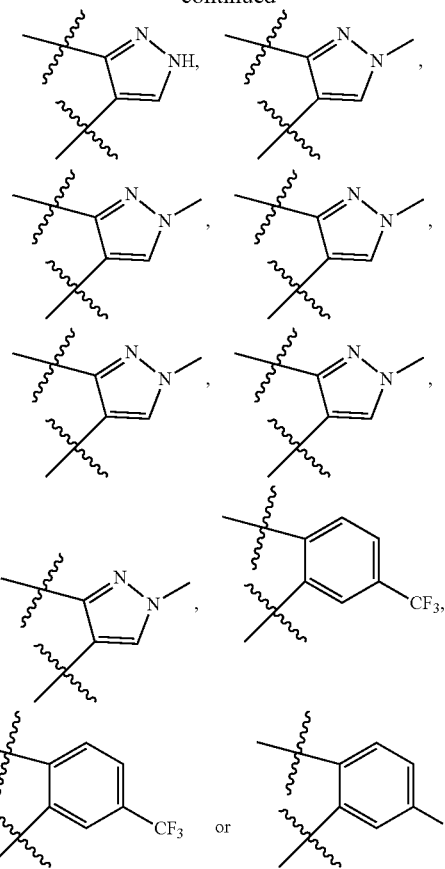

In some embodiments, Y is preferably selected from the following groups:

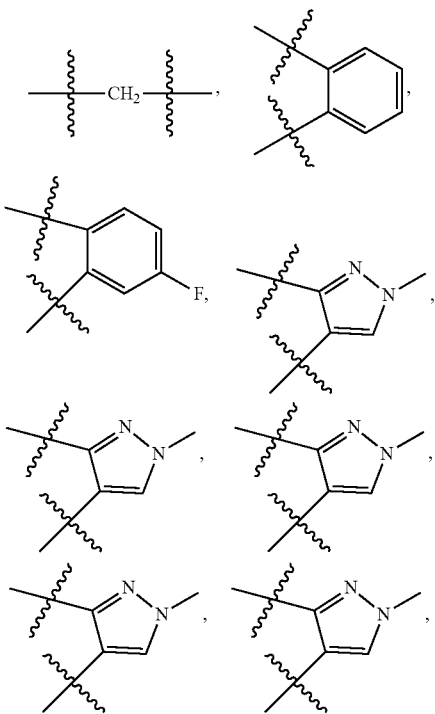

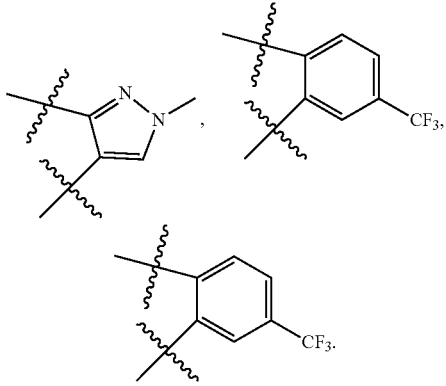
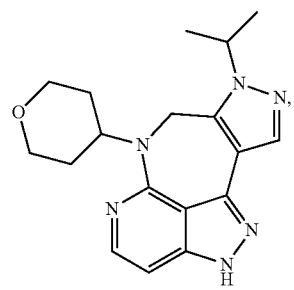
In some embodiments, provided herein is the compound having one of the following structures or a stereoisomer, a tautomer, an N-oxide, a hydrate, a solvate, a metabolite, a pharmaceutically acceptable salt, ester or a prodrug thereof:
67
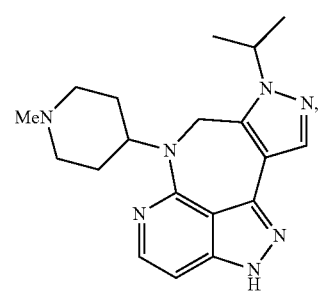
68
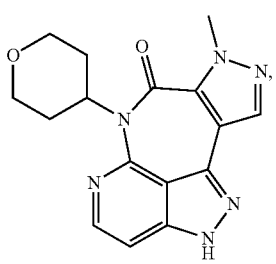
71
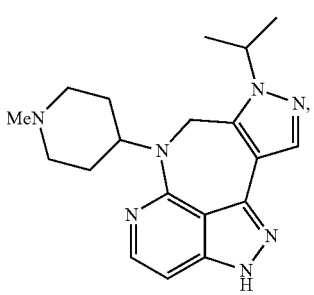
73
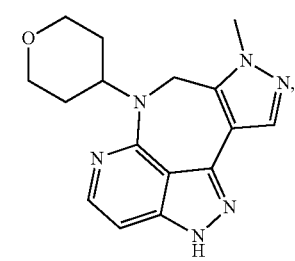
75
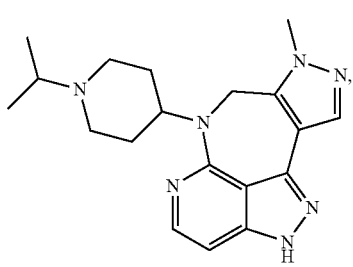
80
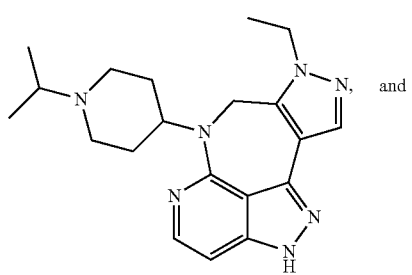
83
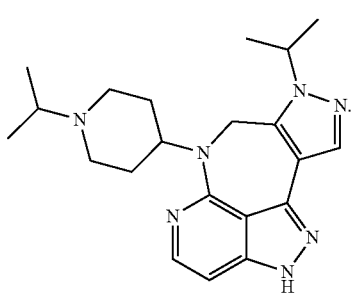
85
and
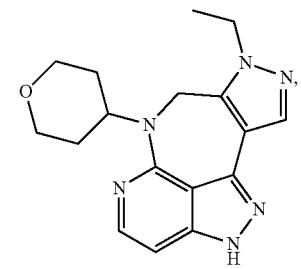
87

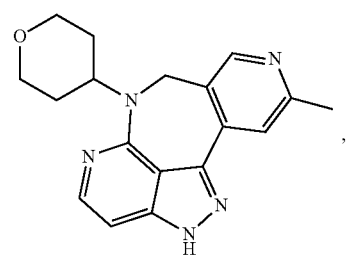
90
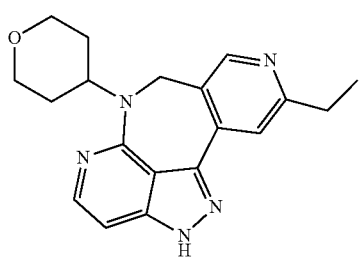
91
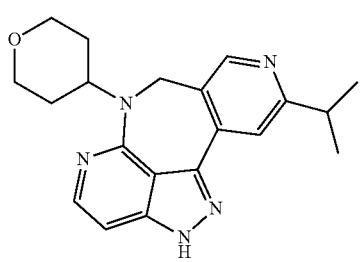
92
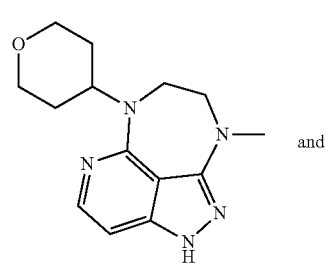
and
93
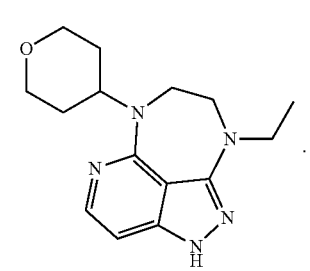
94
In some embodiments, provided herein is the compound having one of the following structures or a stereoisomer, a tautomer, an N-oxide, a hydrate, a solvate, a metabolite, a pharmaceutically acceptable salt, ester or a prodrug thereof preferably:
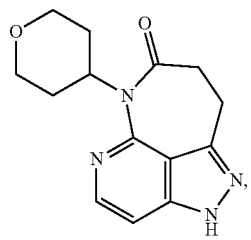
14
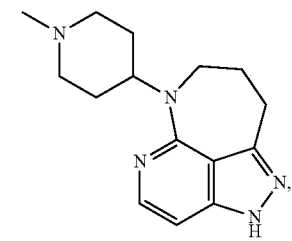
26
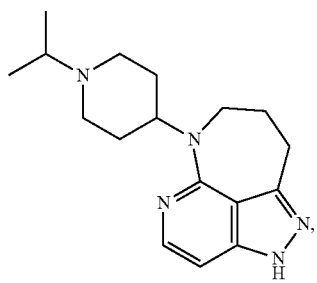
27
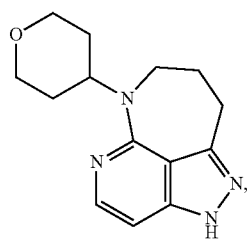
29
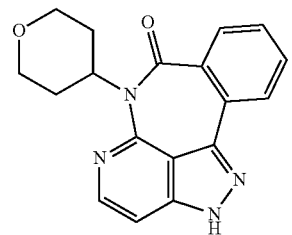
44
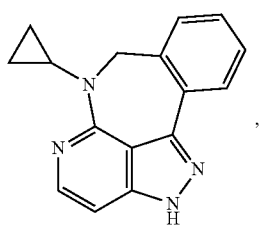
47

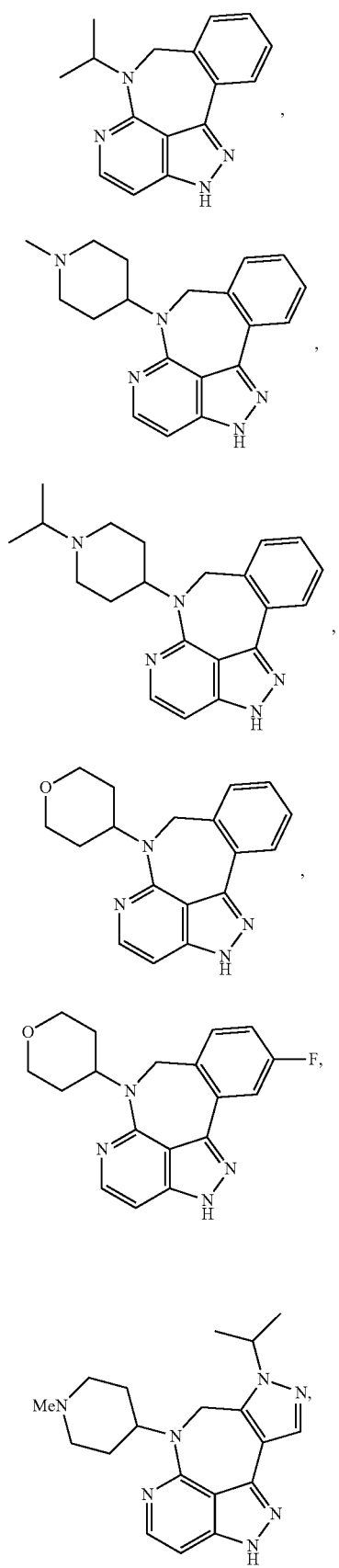
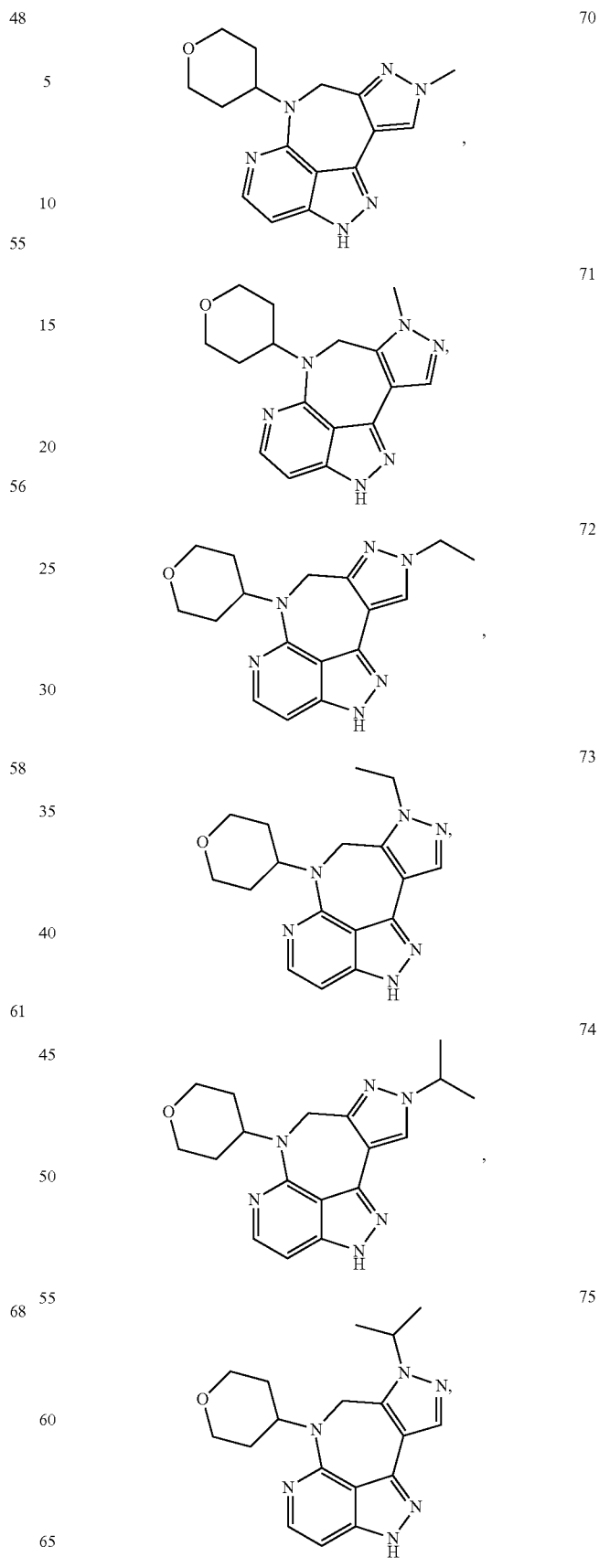

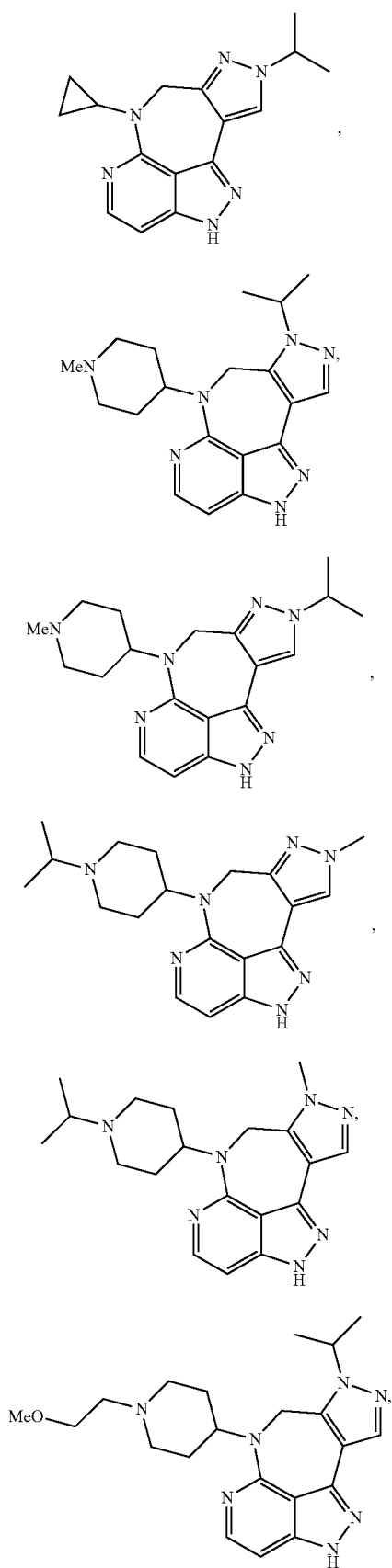
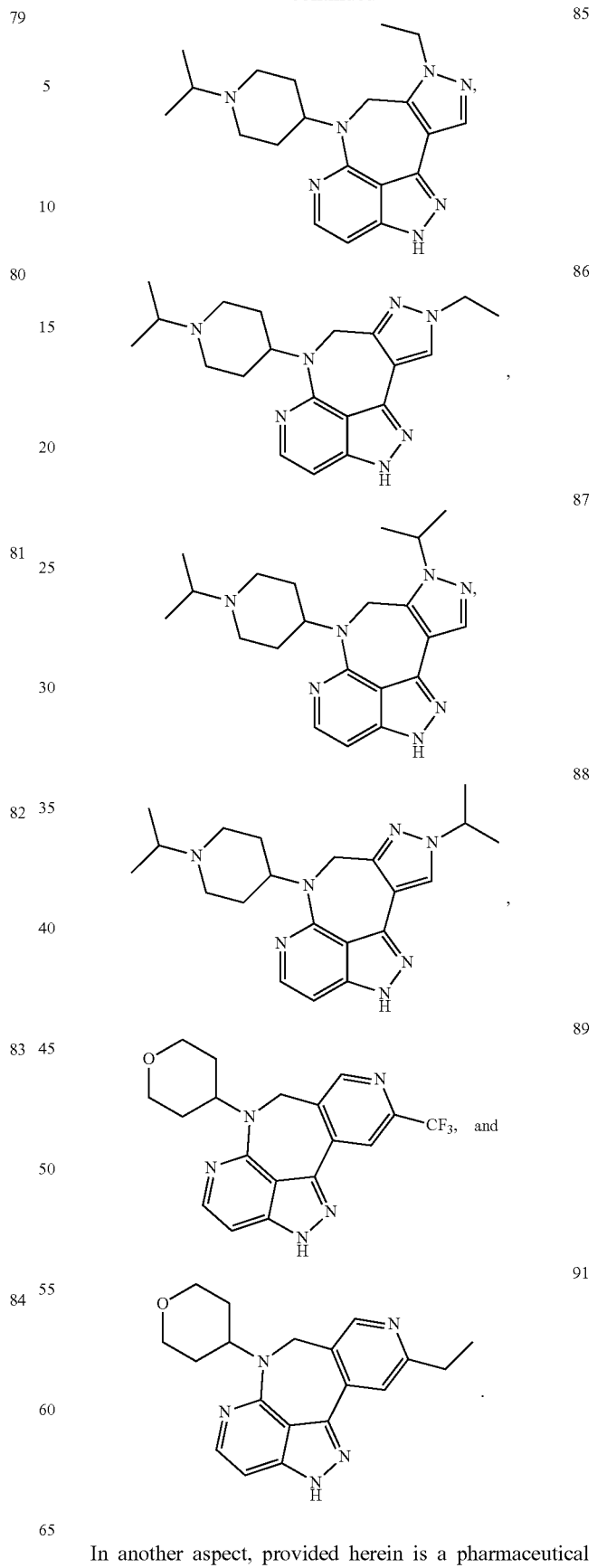
In another aspect, provided herein is a pharmaceutical composition comprising the compound disclosed herein.

In some embodiments, the pharmaceutical composition disclosed herein further comprises a pharmaceutically acceptable carrier, diluent, excipient or a combination thereof.

In some embodiments, the pharmaceutical composition disclosed herein further comprises a second therapeutic agent.

In another aspect, provided herein is use of the compound or the pharmaceutical composition disclosed herein in the manufacture of medicament for treating a disorder caused by at least one of cancer and neurodegenerative disease.

In some embodiments, the neurodegenerative disease is Parkinson's Disease.

In another aspect, provided herein is a method of treating a disorder caused by at least one of cancer and neurodegenerative diseases comprising administrating the subject a therapeutically effective amount of the compound or the pharmaceutical composition disclosed herein.

In some embodiments, the neurodegenerative disease is Parkinson's Disease.

In another aspect, provided herein is the compound or the pharmaceutical composition disclosed herein for use in treating a disorder caused by at least one of cancer and neurodegenerative diseases.

In some embodiments, the neurodegenerative disease is Parkinson's Disease.

In another aspect, provided herein is use of the compound or the pharmaceutical composition disclosed herein in the manufacture of medicament for preventing or treating a disorder caused by, associated with or accompanied by any abnormal kinase activity.

In some embodiments, the kinase is LRRK.
In some embodiments, the kinase is LRRK2.

In another aspect, provided herein is a method of preventing or treating a disorder caused by, associated with or accompanied by any abnormal kinase activity comprising administrating the subject a therapeutically effective amount of the compound or the pharmaceutical composition disclosed herein.

In some embodiments, the kinase is LRRK.
In some embodiments, the kinase is LRRK2.

In another aspect, provided herein is the compound or the pharmaceutical composition disclosed herein for use in preventing or treating a disorder caused by, associated with or accompanied by any abnormal kinase activity.

In some embodiments, the kinase is LRRK.
In some embodiments, the kinase is LRRK2.

In another aspect, provided herein is use of the compound or the pharmaceutical composition disclosed herein in an assay for identifying further candidate compounds capable of inhibiting of a kinase.

In some embodiments, the kinase is LRRK.
In some embodiments, the kinase is LRRK2.

In another aspect, provided herein is a compound of formula II, or a stereoisomer, a tautomer, a N-oxide, a hydrate, a solvate, a metabolite, a pharmaceutically acceptable salt, ester or a prodrug thereof:

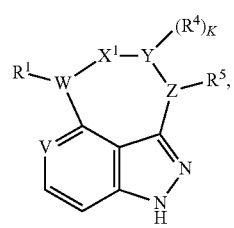

(II)

Wherein V is CH or N;

W is N or O;

$R^1$ is absent, H, $C_{1-10}$ alkyl, $C_{3-10}$ cycloalkyl, $C_{2-10}$ heterocycloalkyl, $C_{6-14}$ aryl, $C_{1-10}$ heteroaryl, $C_{1-5}$ alkyl-$C_{1-10}$-heteroaryl, or $C_{1-5}$-alkyl-$C_{6-14}$-aryl, wherein each of said $C_{1-10}$ alkyl, $C_{3-10}$ cycloalkyl, $C_{2-10}$ heterocycloalkyl, $C_{6-14}$ aryl, $C_{1-10}$ heteroaryl, $C_{1-5}$ alkyl-$C_{1-10}$ heteroaryl and $C_{1-5}$ alkyl-$C_{6-14}$ aryl is independently and optionally substituted with one or more substituents chosen from F, Cl, Br, I, —$NO_2$, —CN, —$N_3$, —$NH_2$, —OH, $C_{1-6}$ alkyl, $C_{3-7}$ cycloalkyl, $C_{2-7}$ heterocycloalkyl, amides, sulfonamides and sulfones;

$X^1$ is a bond, CO, or —$(CH_2)_n$—;

Y is —$(CH_2)_n$—;

Z is a bond, N, or —$(CH_2)_n$—;

each $R^4$ is independently absent, F, Cl, Br, I, —$NO_2$, —CN, —$N_3$, —$NH_2$, —OH, $C_{1-6}$ alkyl, or $C_{1-6}$ haloalkyl, optionally two $R^4$ attached to Y, together with Y, form a $C_3$-$C_{10}$ carbocyclic ring or a 3- to 10-membered heterocyclic ring, wherein each of said $C_3$-$C_{10}$ carbocyclic ring and 3- to 10-membered heterocyclic ring is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl;

$R^5$ is absent, F, Cl, Br, I, —$NO_2$, —CN, —$N_3$, —$NH_2$, —OH, $C_{1-6}$ alkyl, $C_{1-6}$ haloalkyl, optionally $R^4$ and $R^5$ together with Y—Z to which they are attached form a benzene ring, a $C_3$-$C_{10}$ carbocyclic ring, a 3- to 10-membered heterocyclic ring or a 5- to 10-membered heteroaromatic ring, wherein each of said benzene ring, $C_3$-$C_{10}$ carbocyclic ring, a 3- to 10-membered heterocyclic ring and a 5- to 10-membered heteroaromatic ring is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl;

k is 0, 1, 2, 3 or 4;

n is 0, 1, 2, 3, 4 or 5;

In some embodiments, $R^1$ is H, $C_{1-6}$ alkyl, $C_{3-7}$ cycloalkyl, $C_{3-7}$ heterocycloalkyl, $C_{6-10}$ aryl, $C_{1-8}$ heteroaryl, $C_{1-3}$ alkyl-$C_{1-8}$ heteroaryl, or $C_{1-3}$ alkyl-$C_{6-10}$ aryl, wherein each of said $C_{1-6}$ alkyl, $C_{3-7}$ cycloalkyl, $C_{3-7}$ heterocycloalkyl, $C_{6-10}$ aryl, $C_{1-8}$ heteroaryl, $C_{1-3}$ alkyl-$C_{1-8}$ heteroaryl, and $C_{1-3}$ alkyl-$C_{6-10}$ aryl is independently and optionally substituted with one or more substituents chosen from F, Cl, Br, I, —$NO_2$, —CN, —$N_3$, —$NH_2$, —OH, $C_{1-6}$ alkyl, $C_{3-7}$ cycloalkyl, and $C_{3-7}$ heterocycloalkyl.

In some embodiments, X1 is CO, —$CH_2$—, —$(CH_2)_2$—, or —$(CH_2)_3$—.

In some embodiments, Y is —$CH_2$—, —$(CH_2)_2$—, or —$(CH_2)_3$—.

In some embodiments, Z is a bond, N, —$CH_2$—, —$(CH_2)_2$—, or —$(CH_2)_3$—.

In some embodiments, each $R^4$ is independently absent, F, Cl, Br, I, —$NO_2$, —CN, —$N_3$, —$NH_2$, —OH, $C_{1-3}$ alkyl, or $C_{1-3}$ haloalkyl, optionally two $R^4$ attached to Y, together with Y, form a $C_3$-$C_7$ carbocyclic ring or a 3- to 7-membered heterocyclic ring, wherein each of said $C_3$-$C_7$ carbocyclic ring and 3- to 7-membered heterocyclic ring is independently and optionally substituted with one or more substituents chosen from F, Cl, Br, I, —$NO_2$, —CN, —$N_3$, —$NH_2$, —OH, $C_{1-6}$ alkyl, and $C_{1-6}$ haloalkyl.

In some embodiments, $R^5$ is absent, F, Cl, Br, I, —$NO_2$, —CN, —$N_3$, —$NH_2$, —OH, $C_{1-3}$ alkyl, or $C_{1-6}$ haloalkyl, optionally $R^4$ and $R^5$ together with Y—Z to which they are attached form a benzene ring, a $C_3$-$C_7$ carbocyclic ring, a 3- to 7-membered heterocyclic ring or a 5- to 7-membered heteroaromatic ring, wherein each of said benzene ring, $C_3$-$C_7$ carbocyclic ring, a 3- to 7-membered heterocyclic ring and a 5- to 7-membered heteroaromatic ring is independently and optionally substituted with one or more substituents chosen from F, Cl, Br, I, —$NO_2$, —CN, —$N_3$, —$NH_2$, —OH, $C_{1-6}$ alkyl, $C_{1-6}$ haloalkyl.

In some embodiments, $R^1$ is selected from the following groups:

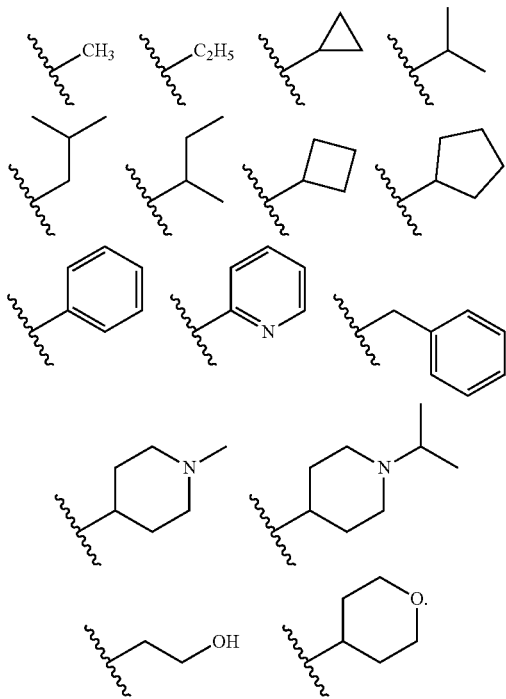

In some embodiments, $R^5$ is absent, F, Cl, Br, I, —$NO_2$, —CN, —$N_3$, —$NH_2$, —OH, $C_{1-3}$ alkyl, or $C_{1-3}$ haloalkyl, optionally $R^4$ and $R^5$ together with Y—Z to which they are attached form the benzene ring or the pyrazole ring, wherein each of said benzene ring and pyrazole ring is independently and optionally substituted with one or more substituents chosen from F, Cl. Br, —CN, —OH, —$CO_2H$, and —$CF_3$.

In another aspect, provided herein is a pharmaceutical composition comprising the compound of formula II disclosed herein.

In some embodiments, the pharmaceutical composition disclosed herein further comprises a pharmaceutically acceptable carrier, diluent, excipient or a combination thereof.

In some embodiments, the pharmaceutical composition disclosed herein further comprises a second therapeutic agent.

In another aspect, provided herein is use of the compound of formula II or the pharmaceutical composition comprising the compound of formula II disclosed herein in the manufacture of medicament for treating a disorder caused by at least one of cancer and neurodegenerative disease.

In some embodiments, the neurodegenerative disease is Parkinson's Disease.

In another aspect, provided herein is a method of treating a disorder caused by at least one of cancer and neurodegenerative diseases comprising administrating the subject a therapeutically effective amount of the compound of formula II or the pharmaceutical composition comprising the compound of formula II disclosed herein.

In some embodiments, the neurodegenerative disease is Parkinson's Disease.

In another aspect, provided herein is the compound of formula II or the pharmaceutical composition comprising the compound of formula II disclosed herein for use in treating a disorder caused by at least one of cancer and neurodegenerative disease.

In some embodiments, the neurodegenerative disease is Parkinson's Disease.

In another aspect, provided herein is use of the compound of formula II or the pharmaceutical composition comprising the compound of formula II disclosed herein in the manufacture of medicament for preventing or treating a disorder caused by, associated with or accompanied by any abnormal kinase activity.

In some embodiments, the kinase is LRRK.
In some embodiments, the kinase is LRRK2.

In another aspect, provided herein is a method of preventing or treating a disorder caused by, associated with or accompanied by any abnormal kinase activity comprising administrating the subject a therapeutically effective amount of the compound of formula II or the pharmaceutical composition comprising the compound of formula II disclosed herein.

In some embodiments, the kinase is LRRK.
In some embodiments, the kinase is LRRK2.

In another aspect, provided herein is the compound of formula II or the pharmaceutical composition comprising the compound of formula II disclosed herein for use in preventing or treating a disorder caused by, associated with or accompanied by any abnormal kinase activity.

In some embodiments, the kinase is LRRK.
In some embodiments, the kinase is LRRK2.

In another aspect, provided herein is use of the compound of formula II or the pharmaceutical composition comprising the compound of formula II disclosed herein in an assay for identifying further candidate compounds capable of inhibiting of a kinase.

In some embodiments, the kinase is LRRK.
In some embodiments, the kinase is LRRK2.

DETAILED DESCRIPTION OF THE INVENTION

Definitions and General Terminology

All references cited in the present invention are hereby incorporated by reference in their entirety, and in case of there are inconsistencies between the incorporated references and the present inventive, the present disclosure will prevail. In addition, all terms and phrases used herein have the general meaning known to those skilled in the art. Even so, it is still desired for making a more detailed explanation to the terms and phrases in the present invention. In case of there are inconsistencies between mentioned terms and phrases and well known meaning, the present disclosure will prevail. The following definitions of general terms used in the present description apply irrespective of whether the terms in question appear alone or in combination.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of Example, "a component" means one or more components, and thus, possibly, more than one component is contemplated and may be employed or used in an implementation of the described embodiments.

As described herein, compounds disclosed herein may optionally be substituted with one or more substituents, such as are illustrated generally below, or as exemplified by particular classes, subclasses, and species of the invention.

The term "halogen" refers to Fluoro (F), Chloro (Cl), Bromo (Br), or Iodo (I).

The term "alkyl" refers to a saturated linear or branched-chain monovalent hydrocarbon radical of 1 to 10 carbon atoms. Unless otherwise stated, the alkyl group contains 1-10 carbon atoms. In some embodiments, the alkyl group contains 1-8 carbon atoms; in other embodiments, the alkyl group contains 1-6 carbon atoms; in still other embodiments, the alkyl group contains 1-4 carbon atoms; in yet other embodiments, the alkyl group contains 1-3 carbon atoms. The alkyl group is optionally substituted with one or more substituents described herein.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), etc.

The term "cycloalkyl" refers to a monovalent or multivalent saturated ring having 3 to 10 carbon atoms as a monocyclic, bicyclic, or tricyclic ring system. And wherein the bicyclic or tricyclic ring system may include fused ring, briged ring and spiro ring. In some embodiments, the cycloalkyl group contains 3 to 8 carbon atoms. In other embodiments, the cycloalkyl group contains 3 to 6 carbon atoms. The cycloalkyl radical is optionally substituted with one or more substituents described herein.

The term "aryl" refers to a monovalent or multivalent monocyclic, bicyclic, or tricyclic carbocyclic ring system having a total of 6 to 12 ring members, preferably, 6 to 10 ring members, and more preferably 6 ring members, and wherein at least one ring in the system is aromatic. The aryl group is generally, but not necessarily bonded to the parent molecule through an aromatic ring of the aryl group. The terms "aryl" and "aromatic ring" can be used interchangeably herein. Examples of aryl group may include phenyl, naphthyl, anthracene, and the like. The aryl radical is optionally substituted with one or more substituents described herein.

The term "heteroaryl" refers to a monovalent or multivalent monocyclic, bicyclic, or tricyclic ring system having a total of 5 to 10 ring members, and wherein at least one ring in the system is aromatic, and at least one ring contains one or more heteroatoms. The heteroaryl group is generally, but not necessarily bonded to the parent molecule through an aromatic ring of the heteroaryl group. The term "hetreroaryl" and "heteroaromatic ring" or "heteroaromatic compound" can be used interchangeably herein. The heteroaryl group is optionally substituted with one or more substituents disclosed herein. In some embodiments, a 5- to 10-membered heteroaryl group contains 1, 2, 3 or 4 heteroatoms independently selected from O, S and N; in some other embodiments, 5- to 6-membered heteroaryl is monocyclic ring system and contains 1, 2, 3 or 4 heteroatoms independently selected from O, S and N.

Some non-limiting examples of the heteroaryl ring include thienyl, furanyl, pyrrolyl, pyridinyl, oxazolyl, thiazolyl, imidazolyl, pyrazolyl, isoxazolyl, isothiazolyl, oxadiazolyl, triazolyl, thiadiazolyl, tetrazolyl etc. and benzo derivatives thereof, such as benzofuranyl, benzothienyl, benzimidazolyl, indolyl, isoindolyl, indazolyl etc.; or pyridyl, pyrazinyl, pyrimidinyl, pyridazinyl, triazinyl etc. and benzo derivatives thereof, such as quinolinyl, isoquinolinyl, cinnolinyl, phthalazinyl, quinazolinyl, quinoxalinyl, naphthyridinyl etc.

"Heterocycloalkyl" refers to a cyclic aliphatic group containing one or more heteroatoms selected from nitrogen, oxygen and sulphur, which is optionally interrupted by one or more —(CO)-groups in the ring and/or which optionally contains one or more double bonds in the ring. Alternatively, the heterocycloalkyl group is a $C_{4-7}$-heterocycloalkyl, more preferably a $C_{4-6}$-heterocycloalkyl. Preferred heterocycloalkyl groups include, but are not limited to, piperazinyl, piperidinyl, morpholinyl, thiomorpholinyl, pyrrolidinyl, tetrahydrofuranyl and tetrahydropyranyl.

Description of Compounds of the Invention

Therapeutic Applications

A further aspect of the invention relates to a compound as described above for use in medicine.

Another aspect of the invention relates to a compound as described above for use in treating cancer or a neurodegenerative disorder.

Another aspect relates to the use of a compound as described above in the preparation of a medicament for treating or preventing a neurodegenerative disorder. Preferably, the neurodegenerative disorder is Parkinson's Disease.

Another aspect relates to the use of a compound as described above in the preparation of a medicament for treating or preventing a proliferative disorder, for example, cancer.

Preferably, the compound is administered in an amount sufficient to inhibit one or more kinases, preferably LRRK, even more preferably LRRK2.

Yet another aspect relates to the use of a compound of the invention in the preparation of a medicament for the prevention or treatment of a disorder caused by, associated with or accompanied by any abnormal activity against a biological target, wherein the target is a kinase, more preferably LRRK, even more preferably LRRK2.

Preferably, the disorder is Parkinson's Disease.

Another aspect of the invention relates to a method of treating a protein kinase related disease or disorder. The method according to this aspect of the present invention is effected by administering to a subject in need thereof a therapeutically effective amount of a compound of the present invention, as described hereinabove, either per se, or, more preferably, as a part of a pharmaceutical composition, mixed with, for example, a pharmaceutically acceptable carrier, as is detailed hereinafter.

Yet another aspect of the invention relates to a method of treating a mammal having a disease state alleviated by inhibition of a protein kinase, wherein the method comprises administering to a mammal a therapeutically effective amount of a compound according to the invention.

Preferably, the disease state is alleviated by the inhibition of the protein kinase LRRK, more preferably LRRK2.

Preferably, the mammal is a human.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "administering" as used herein refers to a method for bringing a compound of the present invention and a protein kinase together in such a manner that the compound can affect the enzyme activity of the protein kinase either directly, i.e., by interacting with the protein kinase itself or indirectly, i.e., by interacting with another molecule on which the catalytic activity of the protein kinase is dependent. As used herein, administration can be accomplished either in vitro, i.e. in a test tube, or in vivo, i.e., in cells or tissues of a living organism.

Herein, the term "treating" includes abrogating, substantially inhibiting, slowing or reversing the progression of a disease or disorder, substantially ameliorating clinical symptoms of a disease or disorder or substantially preventing the appearance of clinical symptoms of a disease or disorder.

Herein, the term "preventing" refers to a method for barring an organism from acquiring a disorder or disease in the first place.

The term "therapeutically effective amount" refers to that amount of the compound being administered which will relieve to some extent one or more of the symptoms of the disease or disorder being treated.

For any compound used in this invention, a therapeutically effective amount, also referred to herein as a therapeutically effective dose, can be estimated initially from cell culture assays. For example, a dose can be formulated in animal models to achieve a circulating concentration range that includes the $IC_{50}$ or the $IC_{100}$ as determined in cell culture. Such information can be used to more accurately determine useful doses in humans. Initial dosages can also be estimated from in vivo data. Using these initial guidelines one of ordinary skill in the art could determine an effective dosage in humans.

Moreover, toxicity and therapeutic efficacy of the compounds described herein can be determined by standard pharmaceutical procedures in cell cultures or experimental animals, e.g., by determining the $LD_{50}$ and the $ED_{50}$. The dose ratio between toxic and therapeutic effect is the therapeutic index and can be expressed as the ratio between $LD_{50}$ and $ED_{50}$. Compounds which exhibit high therapeutic indices are preferred. The data obtained from these cell cultures assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (see, e.g., Fingl et al, 1975, In: The Pharmacological Basis of Therapeutics, chapter 1, page 1).

Dosage amount and interval may be adjusted individually to provide plasma levels of the active compound which are sufficient to maintain therapeutic effect. Usual patient dosages for oral administration range from about 1-2000 mg/kg/day, commonly from about 2-1000 mg/kg/day, preferably from about 5-700 mg/kg/day and most preferably from about 10-500 mg/kg/day. Preferably, therapeutically effective serum levels will be achieved by administering multiple doses each day. In cases of local administration or selective uptake, the effective local concentration of the drug may not be related to plasma concentration. One skilled in the art will be able to optimize therapeutically effective local dosages without undue experimentation.

As used herein, "kinase related disease or disorder" refers to a disease or disorder characterized by inappropriate kinase activity or over-activity of a kinase as defined herein. Inappropriate activity refers to either; (i) kinase expression in cells which normally do not express said kinase; (ii) increased kinase expression leading to unwanted cell proliferation, differentiation and/or growth; or, (iii) decreased kinase expression leading to unwanted reductions in cell proliferation, differentiation and/or growth. Over-activity of kinase refers to either amplification of the gene encoding a particular kinase or production of a level of kinase activity, which can correlate with a cell proliferation, differentiation and/or growth disorder (that is, as the level of the kinase increases, the severity of one or more of the symptoms of the cellular disorder increases). Over activity can also be the result of ligand independent or constitutive activation as a result of mutations such as deletions of a fragment of a kinase responsible for ligand binding.

Preferred diseases or disorders that the compounds described herein may be useful in preventing, include cancer and neurodegenerative disorders such as Parkinson's Disease.

Thus, the present invention further provides use of compounds as defined herein for the manufacture of medicaments for the treatment of diseases where it is desirable to inhibit LRRK2. Such diseases include Parkinson's Disease.

Pharmaceutical Compostions

For use according to the present invention, the compounds or physiologically acceptable salt, ester or other physiologically functional derivative thereof, described herein, may be presented as a pharmaceutical formulation, comprising the compounds or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and PJ Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise, or in addition to, as the carrier, excipient or diluent, any suitable binder(s), lubricant(s), suspending agent(s), coating agent(s), solubilising agent(s), buffer(s), flavouring agent(s), surface active agent(s), thickener(s), preservative(s) (including anti-oxidants) and the like, and substances included for the purpose of rendering the formulation isotonic with the blood of the intended recipient.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds. Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

According to a further aspect of the invention, there is provided a process for the preparation of a pharmaceutical or veterinary composition as described above, the process comprising bringing the active compound(s) into association with the carrier, for example by admixture.

In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) in conjunction or association with a pharmaceutically or veterinarily acceptable carrier or vehicle.

Salts/Esters

The compounds of the invention can be present as salts or esters, in particular pharmaceutically and veterinarily acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. hydrohalic acids such as hydrochloride, hydrobromide and hydroiodide, sulphuric acid, phosphoric acid sulphate, bisulphate, hemisulphate, thiocyanate, persulphate and sulphonic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Salts which are not pharmaceutically or veterinarily acceptable may still be valuable as intermediates.

Preferred salts include, for example, acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, palmoate, pectinate, 3-phenylpropionate, picrate, pivalate, proprionate, tartrate, lactobionate, pivolate, camphorate, undecanoate and succinate, organic sulphonic acids such as methanesulphonate, ethanesulphonate, 2-hydroxyethane sulphonate, camphorsulphonate, 2-naphthalenesulphonate, benzenesulphonate, p-chlorobenzenesulphonate and p-toluenesulphonate; and inorganic acids such as hydrochloride, hydrobromide, hydroiodide, sulphate, bisulphate, hemisulphate, thiocyanate, persulphate, phosphoric and sulphonic acids.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers, diastereoisomers and tautomers of the compounds of the invention. The person skilled in the art will recognise compounds that possess optical properties (one or more chiral carbon atoms) or tautomeric characteristics. The corresponding enantiomers and/or tautomers may be isolated/prepared by methods known in the art.

Enantiomers are characterised by the absolute configuration of their chiral centres and described by the R- and S-sequencing rules of Cahn, Ingold and Prelog. Such conventions are well known in the art (e.g. see 'Advanced Organic Chemistry', $3^{rd}$ edition, ed. March, J., John Wiley and Sons, New York, 1985).

Compounds of the invention containing a chiral centre may be used as a racemic mixture, an enantiomerically enriched mixture, or the racemic mixture may be separated using well-known techniques and an individual enantiomer may be used alone.

Stereo and Geometric Isomers

Some of the compounds of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^{2}H$, $^{3}H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. For example, the invention includes compounds of general formula (I) where any hydrogen atom has been replaced by a deuterium atom. Isotopic variations of the agent of the present invention and pharmaceutically acceptable salts thereof of this invention can generally be prepared by conventional procedures using appropriate isotopic variations of suitable reagents.

Prodrugs

The invention further includes the compounds of the present invention in prodrug form, i.e. covalently bonded compounds which release the active parent drug according to general formula (I) in vivo. Such prodrugs are generally compounds of the invention wherein one or more appropriate groups have been modified such that the modification may be reversed upon administration to a human or mammalian subject. Reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out by an esterase etc. Other such systems will be well known to those skilled in the art.

Solvates

The present invention also includes solvate forms of the compounds of the present invention. The terms used in the claims encompass these forms.

Polymorphs

The invention further relates to the compounds of the present invention in their various crystalline forms, polymorphic forms and (an)hydrous forms. It is well established within the pharmaceutical industry that chemical compounds may be isolated in any of such forms by slightly varying the method of purification and/or isolation form the solvents used in the synthetic preparation of such compounds.

Administration

The pharmaceutical compositions of the present invention may be adapted for rectal, nasal, intrabronchial, topical (including buccal and sublingual), vaginal or parenteral (including subcutaneous, intramuscular, intravenous, intraarterial and intradermal), intraperitoneal or intrathecal administration. Preferably the formulation is an orally administered formulation. The formulations may conveniently be presented in unit dosage form, i.e., in the form of discrete portions containing a unit dose, or a multiple or sub-unit of a unit dose. By way of example, the formulations may be in the form of tablets and sustained release capsules, and may be prepared by any method well known in the art of pharmacy.

Formulations for oral administration in the present invention may be presented as: discrete units such as capsules, gellules, drops, cachets, pills or tablets each containing a predetermined amount of the active agent; as a powder or granules; as a solution, emulsion or a suspension of the active agent in an aqueous liquid or a non-aqueous liquid; or as an oil-in-water liquid emulsion or a water-in-oil liquid emulsion; or as a bolus etc. Preferably, these compositions contain from 1 to 250 mg and more preferably from 10-100 mg, of active ingredient per dose.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropyl-methylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may be optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

Other forms of administration comprise solutions or emulsions which may be injected intravenously, intraarterially, intrathecally, subcutaneously, intradermally, intraperitoneally or intramuscularly, and which are prepared from sterile or sterilisable solutions. Injectable forms typically contain between 10-1000 mg, preferably between 10-250 mg, of active ingredient per dose.

The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin together with such stabilisers and preservatives as may be required.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The dosages disclosed herein are exemplary of the average case. There can of course be individual instances where higher or lower dosage ranges are merited, and such are within the scope of this invention.

In accordance with this invention, an effective amount of a compound of general formula (I) may be administered to inhibit the kinase implicated with a particular condition or disease. Of course, this dosage amount will further be modified according to the type of administration of the compound. For example, to achieve an "effective amount" for acute therapy, parenteral administration of a compound of general formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit a kinase. The compounds may be administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

The compounds of this invention may also be administered orally to the patient, in a manner such that the concentration of drug is sufficient to achieve one or more of the therapeutic indications disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention. The compounds of this invention, which may have good bioavailability, may be tested in one of several biological assays to determine the concentration of a compound which is required to have a given pharmacological effect.

Combinations

In a particularly preferred embodiment, the one or more compounds of the invention are administered in combination with one or more other active agents, for example, existing drugs available on the market. In such cases, the compounds of the invention may be administered consecutively, simultaneously or sequentially with the one or more other active agents.

Drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance.

Beneficial combinations may be suggested by studying the inhibitory activity of the test compounds with agents known or suspected of being valuable in the treatment of a particular disorder. This procedure can also be used to determine the order of administration of the agents, i.e. before, simultaneously, or after delivery. Such scheduling may be a feature of all the active agents identified herein.

Assay

A further aspect of the invention relates to the use of a compound as described above in an assay for identifying further candidate compounds capable of inhibiting one or more kinases, more preferably LRRK, even more preferably, LRRK2.

Preferably, the assay is a competitive binding assay.

More preferably, the competitive binding assay comprises contacting a compound of the invention with a kinase, preferably LRRK, more preferably LRRK2, and a candidate compound and detecting any change in the interaction between the compound according to the invention and the kinase.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

This invention also contemplates the use of competitive drug screening assays in which neutralising antibodies capable of binding a compound specifically compete with a test compound for binding to a compound.

Another technique for screening is provided for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Preferably, the competitive binding assay comprises contacting a compound of the invention with a kinase in the presence of a known substrate of said kinase and detecting any change in the interaction between said kinase and said known substrate.

A further aspect of the invention provides a method of detecting the binding of a ligand to a kinase, said method comprising the steps of:

(i) contacting a ligand with a kinase in the presence of a known substrate of said kinase;

(ii) detecting any change in the interaction between said kinase and said known substrate; and wherein said ligand is a compound of the invention.

One aspect of the invention relates to a process comprising the steps of:

(a) performing an assay method described hereinabove;

(b) identifying one or more ligands capable of binding to a ligand binding domain; and (c) preparing a quantity of said one or more ligands.

Another aspect of the invention provides a process comprising the steps of:

(a) performing an assay method described hereinabove;

(b) identifying one or more ligands capable of binding to a ligand binding domain; and (c) preparing a pharmaceutical composition comprising said one or more ligands.

Another aspect of the invention provides a process comprising the steps of:
(a) performing an assay method described hereinabove;
(b) identifying one or more ligands capable of binding to a ligand binding domain;
(c) modifying said one or more ligands capable of binding to a ligand binding domain;
(d) performing the assay method described hereinabove;
(e) optionally preparing a pharmaceutical composition comprising said one or more ligands.

The invention also relates to a ligand identified by the method described hereinabove.

Yet another aspect of the invention relates to a pharmaceutical composition comprising a ligand identified by the method described hereinabove.

Another aspect of the invention relates to the use of a ligand identified by the method described hereinabove in the preparation of a pharmaceutical composition for the treatment of one or more disorders.

The above methods may be used to screen for a ligand useful as an inhibitor of one or more kinases.

Compounds of general formula (I) are useful both as laboratory tools and as therapeutic agents. In the laboratory certain compounds of the invention are useful in establishing whether a known or newly discovered kinase contributes a critical or at least significant biochemical function during the establishment or progression of a disease state, a process commonly referred to as 'target validation'.

General Synthetic Procedures

The invention is described by the following examples. But it is to be understood that the invention is not limited to those embodiments thereof, the examples are meant only to suggest a method of practicing the present invention.

The following abbreviations are used throughout the specification:
AcOH Acetic acid
AlCl₃ Aluminium muriate
BH₃ Borane
Bn Benzyl
BuOH Butanol
CuI Copper(I) iodide
DCM Dichloromethane
DMF N,N-Dimethylformamide
DMSO Dimethyl sulphoxide
DIEA, DIPEA N,N-diisopropylethylamine
EA Ethyl Acetate
EDCI 1,3-Propanediamine, N3-(ethylcarbonimidoyl)-N1,N1-dimethyl-, hydrochloride
EtOH Ethanol
EtOAc Ethyl Acetate
Et₃N Triethylamine
HATU N,N,N',N'-Tetramethyl-O-(7-azabenzotriazol-1-yl)uronium-hexafluorophospate
HOBT Hydroxybenzotriazole
I₂ Iodine
IPA Isopropanol
KOAc Potassium acetate
KOH Potassium hydroxide
K₃PO₄ Tripotassium phosphate
LiAlH₄ Lithium aluminium hydride
LiCl Lithium chloride
LCMS Mass spectrometry directed high pressure liquid chromatography
MeOH Methanol
MeCN Acetonitrile
MeI Methyl iodide
MsCl Methanesulfonyl chloride
Na₂CO₃ Sodium carbonate
NaHCO₃ Dicarbonate
Na₂S₂O₃ Sodium Thiosulfate
NaOH Sodium hydroxide
NaBH₄ Sodium borohydride
(n-Bu)₄NI Tetrabutylammonium Iodide
n-BuLi n-Butyllithium
NH₃ Ammonia
NH₄Cl Ammonia chloride
NIS N-Iodosuccinimide
NMR Nuclear magnetic resonance
prep-HPLC Preparation High Performance Liquid Chromatography
prep-TLC Preparation Thin-layer chromatography
PMB p-methoxybenzyl
PMBCl p-methoxybenzyl chloride
PPh₃ triphenylphosphine
Pd(dppf)Cl₂ 1,1'-Bis(diphenylphosphino)ferrocene]palladium(II) dichloride
Pd(PPh₃)₄ Tetrakis(triphenylphosphine)palladium(0)
Pd(OAc)₂ Palladium(II) acetate
PE Petroleum Ether
rt Room temperature
Sphos 2-Dicyclohexylphosphino-2',6'-dimethoxybiphenyl
t-BuOK Potassium tert-butoxide
t-BuONa Sodium tert-butoxide
TEA Triethylamine
TLC Thin-layer chromatography
THF Tetrahydrofuran
TFA Trifluoroacetic acid
Trt Trityl
UV Ultraviolet Scheme 1

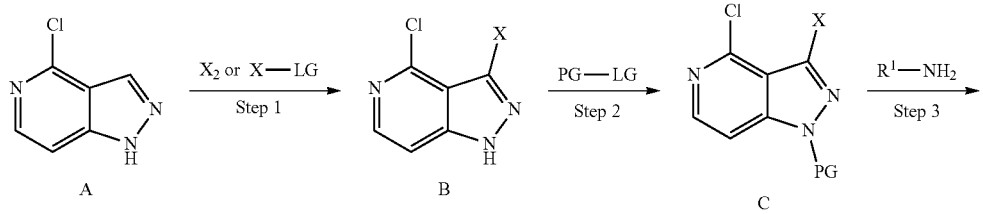

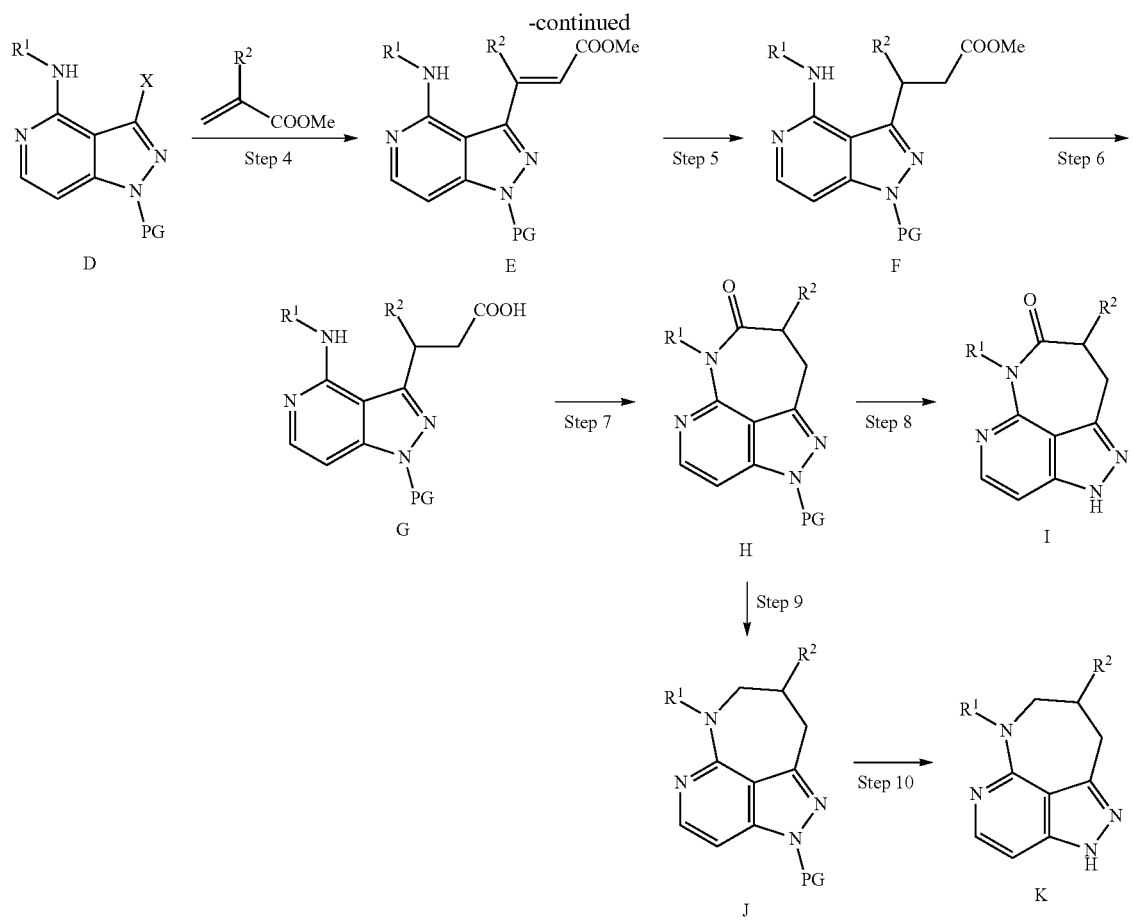

Step 1

Step 1 describes the conversion of formula A into formula B, wherein X is a halogen, preferably bromine or iodine and LG is a leaving group such as succinimide.

The reaction is carried out in the presence of a suitable halogenating agent, such as iodine or N-bromosuccinimide, optionally in the presence of a base, such as potassium hydroxide in a suitable solvent.

Typical conditions (X=I), 1 eq. of formula A, 2 eq. of $I_2$, 3.7 eq of KOH in dioxane at 75° C. for 4 h.

Step 2

Step 2 describes the conversion of formula B into formula C, wherein PG is defined as a protecting group, including but not limited to tert-butoxycarbonyl-; benzyloxycarbonyl-; benzyl-; 4-methoxybenzyl-; 2,4-dimethoxybenzyl- or trityl-; LG is defined as a leaving group, such as a halogen or tert-butylcarbonate.

The reaction involves capping of the pyrazole NH with a protecting group. It will be appreciated by the skilled person, that many protecting groups can be used for this purpose (see Greene, Theodora W. and Wuts, Peter G M. Greene's Protective Groups in Organic Synthesis. 4th Ed. (2006)). The skilled person will also appreciate that it is possible to introduce the protecting group either at N1 or N2, and the ratio may change depending on the nature of PG or the precise reaction conditions deployed. The reaction conditions will depend on the nature of the protecting group.

Typical conditions (PG=4-methoxybenzyl): 1 eq of 4-methoxybenxyl chloride; 1 eq of formula B, 2 eq of potassium hydroxide is stirred in DMF at room temperature overnight.

Step 3

Step 3 describes the conversion of formula C into formula D, wherein X is a halogen, The group R1 can optionally contain a functional group which can be manipulated at later stages in the synthetic process using standard conditions known to the skilled person.

The reaction involves nucleophlic displacement of the chloro group in formula C with an amino group in a suitable solvent, optionally in the presence a Bronsted acid. This reaction generally requires heating, either thermally or with the use of microwave irradiation.

Typical conditions: 2.5 eq. of amine, 1 eq. of formula C in n-butanol, heated to 180° C. in a sealed bomb for 5 h.

Step 4

Step 4 involves the conversion of formula D to formula E. X is a halogen, but preferably an iodine. The reaction involves a cross coupling of a substituted vinyl ester with formula D in the presence of a suitable transition metal catalyst and a suitable base, preferably triethylamine and optionally additional additives, such as tetrabutyl ammonium iodide. This type of transformation is often known as a "Heck Reaction" to those skilled in the art.

Typical conditions: 1 eq. of formula D, 10 eq. of vinyl ester, 2 eq. of tetrabutylammonium iodide, 0.2 eq. of Pd(dppf)Cl2 in DMF; Water:triethylamine (6.25:1:1) is heated to 70° C. overnight.

Step 5

Step 5 involves the conversion of formula E into formula F. The reaction involves hydrogenation of the double bond to the corresponding saturated compound with a hydrogen source in the presence of a suitable transition metal catalyst in a suitable solvent. It may be necessary or desirable to add a Bronsted acid (such as HCl, or acetic acid) to facilitate this reaction. The person skilled in the art will appreciate that a number of different metal catalysts can be used for this type of reaction and that it may be necessary or desirable to carry out these reactions under pressure.

Typical conditions: formula E is treated with palladium on carbon under an atmosphere of hydrogen.

Step 6

Step 6 involves the conversion of formula F into formula G The reaction involves hydrolysis of the ester to the corresponding carboxylic acid with water in the presence of a suitable base such as sodium hydroxide in a suitable solvent.

Typical conditions: formula F is treated with aqueous sodium hydroxide in methanol.

Step 7

Step 7 involves the conversion of formula G into formula H. The reaction involves intramolecular cyclization to form a lactam under amide bond forming reaction conditions. The person skilled in the art will appreciate that a number of different amide bond forming reaction conditions can be used for this type of reaction.

Typical conditions: Formula G is treated with HATU in the presence of triethylamine in dichloromethane.

Step 8

Step 8 involves the conversion of formula H into formula I. The reaction involved removal of the protecting group from the pyrazole and the precise conditions will vary depending the nature of the protecting group (Greene, Theodora W. and Wuts, Peter G M. Greene's Protective Groups in Organic Synthesis. 4th Ed. (2006).

Typical conditions (PG is 4-methoxybenzyl): Formula H is treated with trifluoroacetic acid at 70° C. overnight.

Step 9

Step 9 involves the conversion of formula H into formula J. The reaction involves reduction of the amide to the corresponding amine with a reducing agent such as borane. The person skilled in the art will appreciate that a number of different reducing agents can be used for this type of reaction.

Step 10

Step 10 involves the conversion of formula J to formula K. The reaction involves removal of the protecting group from the pyrazole, and the precise conditions will depend on the nature of the protecting group (Greene, Theodora W. and Wuts, Peter G M. Greene's Protective Groups in Organic Synthesis. 4th Ed. (2006).

Typical conditions (PG is 4-methoxybenzyl): Formula J is treated with trifluoroacetic acid at 70° C. overnight.

Scheme 2

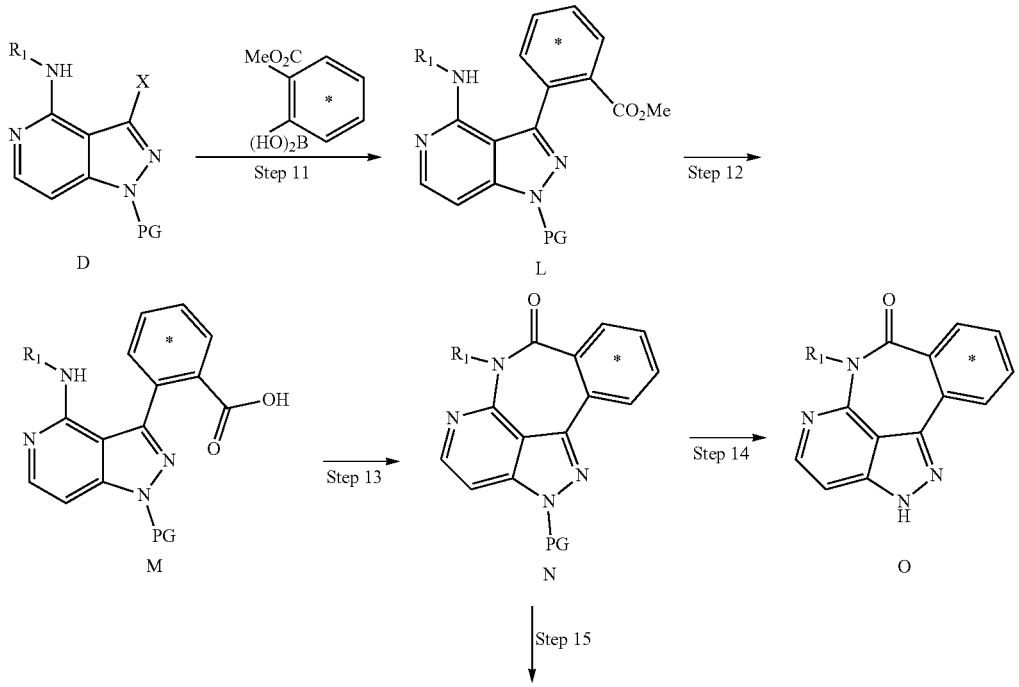

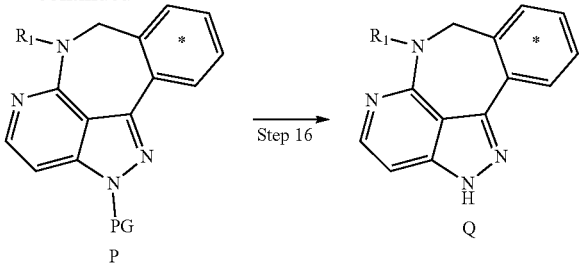

*: the benzene ring may be replaced by an aryl or heteroaryl ring.

Step 11

Step 11 describes the conversion of formula D into formula L wherein X and PG are as defined previously. The reaction involves cross-coupling of the halide in formula D with an aryl or heteroaryl boronic acid or ester in the presence of a transition metal catalyst in a suitable solvent. The reactions are typically carried out at elevated temperatures with either thermal or microwave heating. An inorganic base (such as sodium carbonate) is generally added to the reaction mixture. Transformations of this type are known as "Suzuki Couplings" to those skilled in the art.

Typical conditions: 1 eq. of formula D, 0.09 eq. of Pd(dppf)2Cl2, 1.5 eq. of the boronic acid (or boronic ester), 3.5 eq. of 2M aqueous sodium carbonate in dioxane at 90° C. for 18 h.

Step 12

Step 12 involves the conversion of formula L into formula M. The reaction involves hydrolysis of the ester to the corresponding carboxylic acid with water in the presence of a suitable base such as sodium hydroxide in a suitable solvent.

Typical conditions: formula L is treated with aqueous sodium hydroxide in methanol.

Step 13

Step 13 involves the conversion of formula M into formula N. The reaction involves intramolecular cyclization to form a lactam under amide bond forming reaction conditions. The person skilled in the art will appreciate that a number of different amide bond forming reaction conditions can be used for this type of reaction.

Typical conditions: Formula M is treated with HATU in the presence of triethylamine in dichloromethane.

Step 14

Step 14 involves the conversion of formula N into formula O. The reaction involved removal of the protecting group from the pyrazole and the precise conditions will vary depending the nature of the protecting group (Greene, Theodora W. and Wuts, Peter G M. Greene's Protective Groups in Organic Synthesis. 4th Ed. (2006).

Typical conditions (PG is 4-methoxybenzyl): Formula N is treated with trifluoroacetic acid at 70° C. overnight.

Step 15

Step 15 involves the conversion of formula N into formula P. The reaction involves reduction of the amide to the corresponding amine with a reducing agent such as borane. The person skilled in the art will appreciate that a number of different reducing agents can be used for this type of reaction.

Step 16

Step 16 involves the conversion of formula P to formula Q. The reaction involves removal of the protecting group from the pyrazole, and the precise conditions will depend on the nature of the protecting group (Greene, Theodora W. and Wuts, Peter G M. Greene's Protective Groups in Organic Synthesis. 4th Ed. (2006).

Typical conditions (PG is 4-methoxybenzyl): Formula P is treated with trifluoroacetic acid at 70° C. overnight.

The invention is further described by way of the following non-limiting examples.

EXAMPLES

General Procedures for Synthesis of Compounds
Chromatography

High pressure liquid chromatography was carried out using apparatus made by Agela Technologies and monitored by a multi-wavelength UV detector. Typical mobile phase for the separation process was PE/EA, DCM/MeOH or water/MeCN. It will be appreciated by those skilled in the art that it may be necessary or desirable to modify the conditions for each specific compound, for example by changing the solvent composition at the start or at the end, modifying the solvents or buffers, changing the run time, changing the flow rate and/or the chromatography column.

Analytical Methods $^1$H Nuclear magnetic resonance (NMR) spectroscopy was carried out using a Bruker AV 400 spectrometer in the stated solvent at room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; br, broad. Mass spectra were recorded using an Agilent 1290 Infinity/6460 triple Quad LCMS. Where thin layer chromatography (TLC) has been used it refers to silica gel TLC.

Compound Preparation

Where the preparation of starting materials is not described, these are commercially available, known in the literature, or readily obtainable by those skilled in the art using standard procedures. Where it is stated that compounds were prepared analogously to earlier examples or intermediates, it will be appreciated by the skilled person that the reaction time, number of equivalents of reagents and temperature can be modified for each specific reaction and that it may be necessary or desirable to employ different work-up or purification techniques.

Example 1

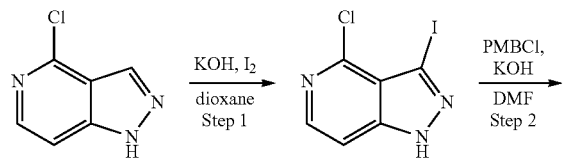

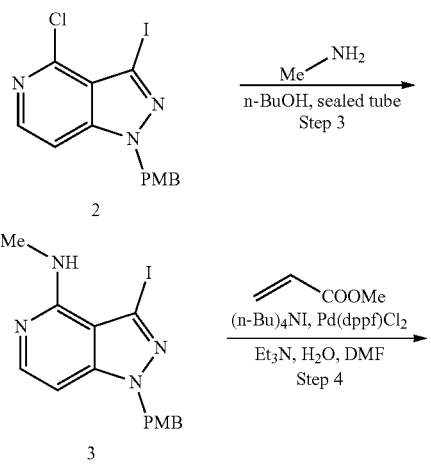

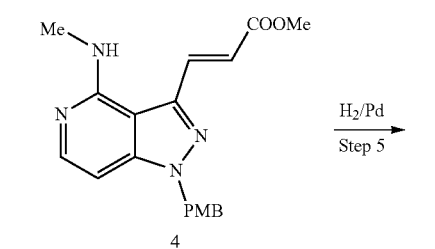

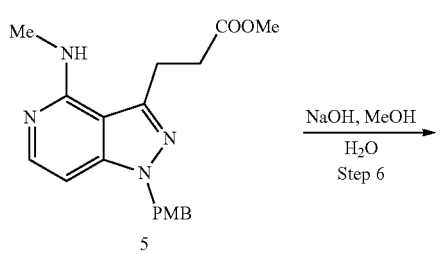

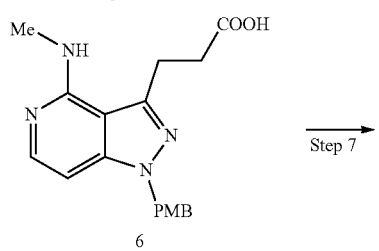

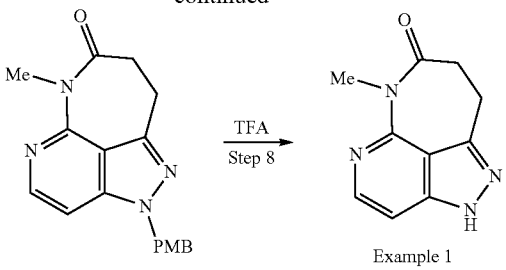

Step 1 Synthesis of 4-Chloro-3-iodo-1H-pyrazolo[4,3-c]pyridine (Intermediate 1)

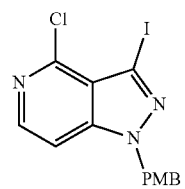

To a mixture of 4-chloro-1H-pyrazolo[4,3-c]pyridine (5.8 g, 38 mmol, synthesized according to WO 2010106333A1 and WO 2012038743A1) and KOH (8 g, 142 mmol) in dioxane (100 mL) at room temperature was added iodine (19 g, 76 mmol). The reaction mixture was stirred at 75° C. for 4 h and then allowed to cool to room temperature. The solution was diluted with saturated $Na_2S_2O_3$ (aq) and the resulting precipitate was filtered and dried to give a yellow solid (4.1 g). The filtrate was left standing for 3 days and filtration of the resulting precipitate yielded a further 3.55 g of the product. Combined yield (7.65 g, 72%). $^1$H NMR (400 MHz, CDCl$_3$) δ ppm 7.65 (d, J=6.0 Hz, 1H), 8.13 (d, J=6.0 Hz, 1H), 14.22 (s, 1H). m/z (ESI)$^+$: 280 [M+H]$^+$ Step 2 Synthesis of 1-(4-methoxybenzyl)-4-chloro-3-iodo-1H-pyrazolo[4,3-c]pyridine (Intermediate 2)

To a mixture of intermediate 1 (1 g, 3.6 mmol) and KOH (0.3 g, 5.4 mmol) in DMF (10 mL) at room temperature was added 4-methoxybenzyl chloride (0.5 mL, 3.6 mmol). The resulting mixture was stirred at room temperature for 2.5 h and then evaporated to dryness. The crude residue was dissolved in EtOAc and washed with water. The organic phase was dried and concentrated to dryness. The residue was purified with flash chromatography, eluting with 0 to 30% EtOAc/PE gradient, to give a 9:1 mixture of N1:N2 regioisomers as a solid (1.3 g, 93%). Major regioisomer: $^1$H NMR (400 MHz, DMSO-d$_6$) δ ppm 3.70 (s, 3H), 5.57 (s, 2H), 6.87 (d, J=8.8 Hz, 2H), 7.22 (d, J=8.4 Hz, 2H), 7.80 (d, J=4.8 Hz, 1H), 8.17 (d, J=4.4 Hz, 1H). m/z (ESI)$^+$: 400 [M+H]$^+$.

Step 3 Synthesis of 1-(4-methoxybenzyl)-3-iodo-N-methyl-1H-pyrazolo[4,3-c]pyridin-4-amine (Intermediate 3)

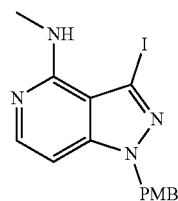

To a solution of intermediate 2 (1.0 g, 2.50 mmol) in n-BuOH (6 mL) was added methanamine (6 mL, 40% aq). The mixture was stirred at 170° C. in a sealed bomb for 5 h, then evaporated and the residue was purified with flash chromatography, eluting with 0-50% EtOAc/DCM, to give a white solid (0.84 g, 85%). $^1$H NMR (400 MHz, DMSO-$d_6$) δ ppm 1.71 (m, 2H), 2.24 (m, 4H), 4.43 (s, 2H), 4.94 (m, 1H), 6.80 (d, J=6.0 Hz, 1H), 7.41 (m, 2H), 7.59 (d, J=6.8 Hz, 1H), 7.78 (d, J=6.0 Hz, 1H), 7.98 (d, J=7.2 Hz, 1H), 13.28 (s, 1H); m/z (ESI)$^+$: 395 [M+H]$^+$.

Step 4 Synthesis of methyl (E)-3-(4-(methylamino)-1-(4-methoxybenzyl)-1H-pyrazolo[4,3-c]pyridin-3-yl)acrylate (Intermediate 4)

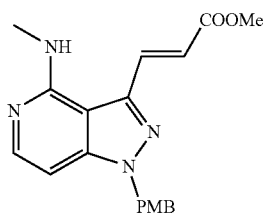

To a mixture of intermediate 3 (595 mg, 1.51 mmol) and tetrabutylammonium iodide (1.11 g, 3.02 mmol) in DMF/water/triethylamine (26 mL/2.8 mL/2.8 mL) at room temperature under Argon was added methyl acrylate (1.30 g, 15.08 mmol) and Pd(dppf)Cl$_2$ (220 mg, 0.3 mmol). The resulting mixture was heated at 70° C. in a sealed bomb overnight and then evaporated to dryness. The crude residue was dissolved in EtOAc and washed with water and brine. The organic phase was dried with Na$_2$SO$_4$, filtered, evaporated to dryness and purified with flash chromatography, eluting with 0 to 60% ethyl acetate/petroleum ether gradient, to give a brown gum (80%). $^1$H NMR (400 MHz, DMSO-$d_6$) δ ppm 2.93 (d, J=4.4 Hz, 3H), 3.69 (s, 3H), 3.75 (s, 3H), 5.49 (s, 2H), 6.72 (m, 2H), 6.87 (d, J=8.4 Hz, 2H), 6.92 (d, J=6.0 Hz, 1H), 7.22 (d, J=8.0 HZ, 2H), 7.83 (d, J=6.0 Hz, 1H), 8.11 (d, J=17.6 Hz, 1H); m/z (ESI)$^+$: 353 [M+H]$^+$.

Step 5 Synthesis of methyl 3-(4-(methylamino)-1-(4-methoxybenzyl)-1H-pyrazolo[4,3-c]pyridin-3-yl)propanoate (Intermediate 5)

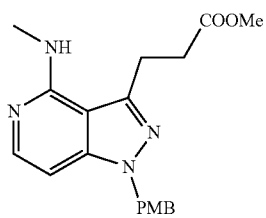

To a solution of intermediate 4 (317 mg, 0.90 mmol) in ethyl acetate (10 ml) and methanol (10 mL) was added 10% Pd/C (0.1 g) and acetic acid (2 mL). The resulting mixture was stirred under H$_2$ atmosphere at room temperature overnight and then filtered through Celite. The filter cake was washed with EtOAc twice and the combined filtrates were evaporated to afford a white solid in 90% yield. The residue was used for the next step without further purification. m/z (ESI)$^+$: 355 [M+H]$^+$.

Step 6 Synthesis of 3-(4-(methylamino)-1-(4-methoxybenzyl)-1H-pyrazolo[4,3-c]pyridin-3-yl)-propanoic Acid (Intermediate 6)

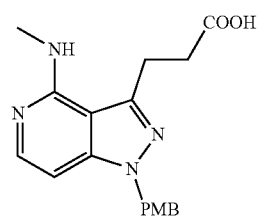

To a solution of Intermediate 5 (283 mg, 0.80 mmol) in methanol (15 mL) and water (3 mL) at room temperature was added NaOH (160 mg, 4.0 mmol). The resulting mixture was stirred for 4 h at 40° C. and then adjusted to pH 4 with acetic acid. After evaporating, the residue was purified with flash chromatography, eluting with 0 to 30% methanol/DCM gradient, to give a yellow solid (68%). $^1$H NMR (400 MHz, DMSO-$d_6$) δ ppm: 2.68 (d, J=7.2 Hz, 2H), 2.91 (d, J=4.4 Hz, 3H), 3.21 (t, J=7.2 Hz, 2H), 3.70 (d, J=6.0 Hz, 3H), 5.33 (d, J=8.4 Hz, 2H), 6.33 (d, J=6.8 Hz, 1H), 6.74 (d, J=10.4 Hz, 1H), 6.86 (d, J=10.0 Hz, 2H), 7.13 (d, J=8.4 Hz, 2H), 7.72 (d, J=10.0 Hz, 1H), 12.20 (br s, 1H); m/z (ESI)$^+$: 341 [M+H]$^+$.

Step 7 Synthesis of 6-methyl-2-(4-methoxybenzyl)-2,6,8,9-tetrahydro-7H-1,2,5,6-tetraazabenzo[cd]azulen-7-one (Intermediate 7)

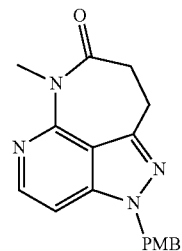

To a solution of intermediate 6 (4.31 g, 12.67 mmol) in dry THF (250 mL) was added HOBt (2.06 g, 15.21 mmol) and DIPEA (1.97 g, 15.21 mmol) under Argon. The mixture was cooled to 0° C. and then EDCI (2.92 g, 15.21 mmol) was added. After stirring for 0.5 h at 0° C., the reaction mixture was warmed up to room temperature and stirred overnight and then quenched with water (100 mL). Most of THF was evaporated and the residue was partitioned between EtOAc and water. The organic layer was washed with brine (100 mL), dried with Na$_2$SO$_4$ and concentrated under vacuum. The residue was purified with flash chromatography (EtOAc/PE gradient) to gave a white solid (75%). $^{1}$H NMR (400 MHz, DMSO-$d_6$) δ ppm: 2.94 (m, 2H), 3.12 (m, 2H), 3.52 (s, 3H), 3.70 (s, 3H), 5.50 (s, 2H), 6.87 (d, J=8.8 Hz, 2H), 7.23 (d, J=8.4 Hz, 2H), 7.43 (d, J=6.0 Hz, 1H), 8.16 (d, J=6.0 Hz, 1H); m/z (ESI)$^{+}$: 323 [M+H]$^{+}$.

Step 8 Synthesis of 6-methyl-2,6,8,9-tetrahydro-7H-1,2,5,6-tetraazabenzo[cd]azulen-7-one (Example 1)

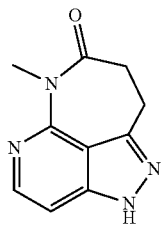

A solution of intermediate 7 in TFA (150 mg in 5 mL) was stirred at 90° C. in a sealed bomb overnight. After cooling to room temperature, the mixture was concentrated under vacuum, redissolved in DCM/MeOH (1:1, v/v, 10 mL), neutralized with $K_2CO_3$, filtered, washed and concentrated to dryness. The residue was subsequently purified with flash chromatography, eluting with 0 to 30% methanol/DCM gradient, and then purified with a reversed-phase C-18 column, eluting with 5 to 60% MeCN/water gradient, to give the product as a white solid (75%). $^{1}$H NMR (400 MHz, DMSO-$d_6$) δ ppm 2.94 (s, 2H), 3.13 (s, 2H), 3.49 (s, 3H), 7.18 (s, 1H), 8.14 (s, 1H), 13.30 (br s, 1H); m/z (ESI)$^{+}$: 203 [M+H]$^{+}$.

Examples 2-14

Examples 2-14 were prepared similarly to Example 1 replacing methanamine with the appropriate amine in Step 3.

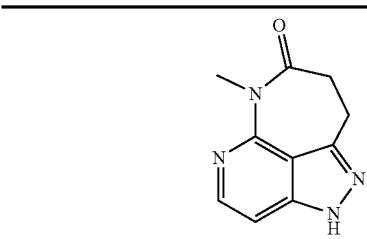

| Example | R | Name | m/z (ESI)$^{+}$ [M + H]$^{+}$ |
|---|---|---|---|
| 2 | C$_2$H$_5$ | 6-ethyl-2,6,8,9-tetrahydro-7H-1,2-5,6-tetraazabenzo[cd]azulen-7-one | 217 |
| 3 | cyclopropyl | 6-cyclopropyl-2,6,8,9-tetrahydro-7H-1,2,5,6-tetraazabenzo[cd]azulen-7-one | 229 |
| 4 | isopropyl | 6-isopropyl-2,6,8,9-tetrahydro-7H-1,2,5,6-tetraazabenzo[cd]azulen-7-one | 231 |
| 5 | isobutyl | 6-isobutyl-2,6,8,9-tetrahydro-7H-1,2,5,6-tetraazabenzo[cd]azulen-7-one | 245 |
| 6 | sec-butyl | 6-(sec-butyl)-2,6,8,9-tetrahydro-7H-1,2,5,6-tetraazabenzo[cd]azulen-7-one | 245 |
| 7 | cyclobutyl | 6-cyclobutyl-2,6,8,9-tetrahydro-7H-1,2,5,6-tetraazabenzo[cd]azulen-7-one | 243 |
| 8 | cyclopentyl | 6-cyclopentyl-2,6,8,9-tetrahydro-7H-1,2,5,6-tetraazabenzo[cd]azulen-7-one | 257 |
| 9 | phenyl | 6-phenyl-2,6,8,9-tetrahydro-7H-1,2,5,6-tetraazabenzo[cd]azulen-7-one | 265 |
| 10 | Bn | 6-benzyl-2,6,8,9-tetrahydro-7H-1,2,5,6-tetraazabenzo[cd]azulen-7-one | 279 |
| 11 | 1-methylpiperidin-4-yl | 6-(1-methylpiperidin-4-yl)-2,6,8,9-tetrahydro-7H-1,2,5,6-tetraazabenzo[cd]azulen-7-one | 286 |
| 12 | 1-isopropylpiperidin-4-yl | 6-(isopropylpiperidin-4-yl)-2,6,8,9-tetrahydro-7H-1,2,5,6-tetraazabenzo[cd]azulen-7-one | 314 |
| 13 | CH$_2$CH$_2$OH | 6-(2-hydroxyethyl)-2,6,8,9-tetrahydro-7H-1,2,5,6-tetraazabenzo[cd]azulen-7-one | 233 |
| 14 | tetrahydro-2H-pyran-4-yl | 6-(tetrahydro-2H-pyran-4-yl)-2,6,8,9-tetrahydro-7H-1,2,5,6-tetraazabenzo[cd]azulen-7-one | 273 |

Example 15

Example 15 was prepared similarly to Example 14 replacing methyl acrylate with methyl methacrylate in Step 4.

| Example | Structure | Name | m/z (ESI)+ [M + H]+ |
|---|---|---|---|
| 15 | 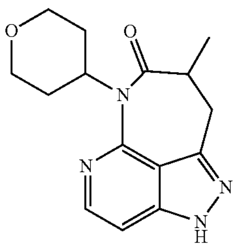 [SMILES: CC1Cc2n[nH]c3ccnc(c23)N(C2CCOCC2)C1=O] | 8-methyl-6-(tetrahydro-2H-pyran-4-yl)-2,6,8,9-tetrahydro-7H-1,2,5,6-tetraazabenzo[cd]azulen-7-one | 287 |

Example 16

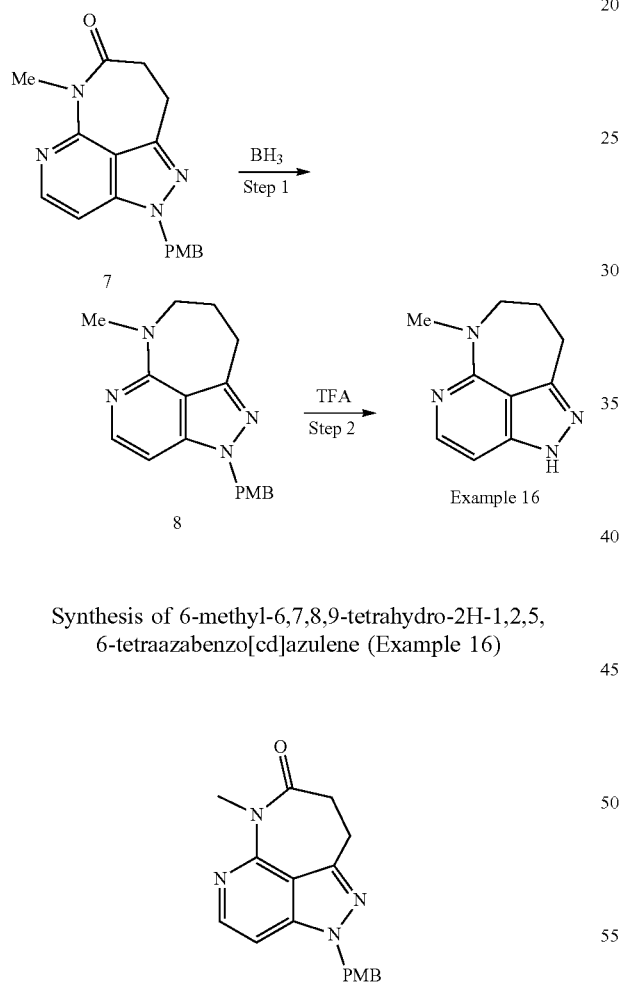

Synthesis of 6-methyl-6,7,8,9-tetrahydro-2H-1,2,5,6-tetraazabenzo[cd]azulene (Example 16)

To a solution of intermediate 7 (328 mg in 10 mL dry THF, 1.02 mmol) in example 1 was added BH$_3$ (1 M in THF, 5 mL,) at 0° C. After stirring at room temperature for 16 h under Argon, the reaction mixture was quenched with the addition of methanol (10 mL) and concentrated under vacuum. The crude intermediate product 8 was dissolved in TFA (5 mL) and stirred at 90° C. in a sealed bomb overnight. After cooling to room temperature, the mixture was concentrated under vacuum and dissolved in DCM/MeOH (1:1, v/v, 10 mL), neutralized with K$_2$CO$_3$, filtered and concentrated to dryness. The residue was subsequently purified with flash chromatography, eluting with 0 to 30% methanol/DCM gradient, and then purified with a reversed-phase C-18 column, eluting with 5 to 60% MeCN/water gradient, to give a yellow solid (15% for two steps). $^1$H NMR (400 MHz, DMSO-d$_6$) δ ppm 2.05 (m, 2H), 2.98 (m, 2H), 3.33 (s, 3H), 3.66 (m, 2H), 6.74 (d, J=6.0 Hz, 1H), 7.70 (d, J=6.0 Hz, 1H), 13.07 (br s, 1H); m/z (ESI)$^+$: 189 [M+H]$^+$.

Examples 17-29

Examples 17-29 were prepared similarly to example 16 replacing intermediate 7 with the appropriate intermediate which in turn was prepared by replacing methanamine with the appropriate amine in Step 3, example 1 as shown below.

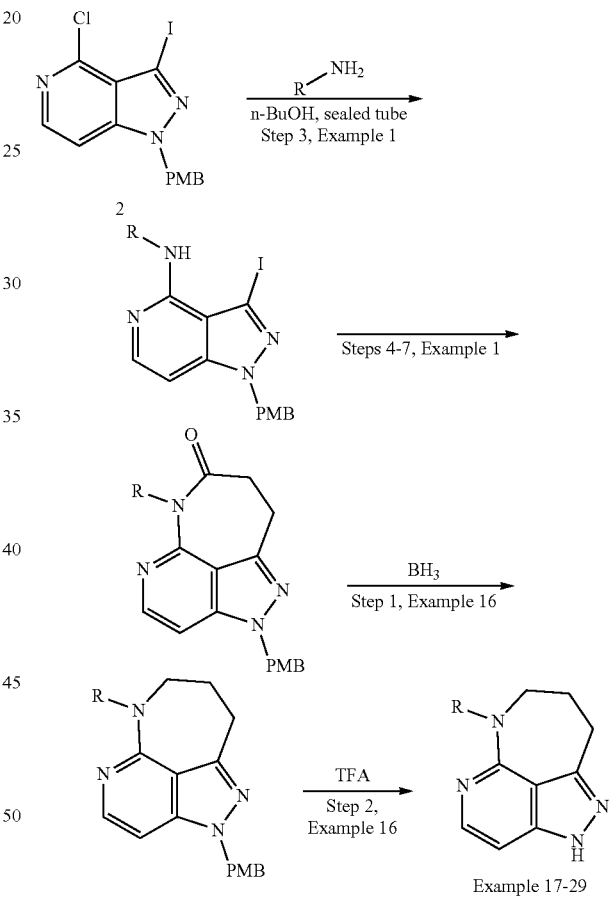

| Example | R | Name | m/z (ESI)+ [M + H]+ |
|---|---|---|---|
| 17 | —C$_2$H$_5$ | 6-ethyl-6,7,8,9-tetrahydro-2H-1,2,5,6-tetraazabenzo[cd]azulene | 203 |
| 18 | cyclopropyl | 6-cyclopropyl-6,7,8,9-tetrahydro-2H-1,2,5,6-tetraazabenzo[cd]azulene | 215 |

-continued

| Example | R | Name | m/z (ESI)+ [M + H]+ |
|---|---|---|---|
| 19 | isopropyl | 6-isopropyl-6,7,8,9-tetrahydro-2H-1,2,5,6-tetraazabenzo[cd]azulene | 217 |
| 20 | isobutyl | 6-isobutyl-6,7,8,9-tetrahydro-2H-1,2,5,6-tetraazabenzo[cd]azulene | 231 |
| 21 | sec-butyl | 6-(sec-butyl)-6,7,8,9-tetrahydro-2H-1,2,5,6-tetraazabenzo[cd]azulene | 231 |
| 22 | cyclobutyl | 6-cyclobutyl-6,7,8,9-tetrahydro-2H-1,2,5,6-tetraazabenzo[cd]azulene | 229 |
| 23 | cyclopentyl | 6-cyclopentyl-6,7,8,9-tetrahydro-2H-1,2,5,6-tetraazabenzo[cd]azulene | 243 |
| 24 | phenyl | 6-phenyl-6,7,8,9-tetrahydro-2H-1,2,5,6-tetraazabenzo[cd]azulene | 251 |
| 25 | Bn | 6-benzyl-6,7,8,9-tetrahydro-2H-1,2,5,6-tetraazabenzo[cd]azulene | 265 |
| 26 | 1-methylpiperidin-4-yl | 6-(1-methylpiperidin-4-yl)-6,7,8,9-tetrahydro-2H-1,2,5,6-tetraazabenzo[cd]azulene | 272 |
| 27 | 1-isopropylpiperidin-4-yl | 6-(1-isopropylpiperidin-4-yl)-6,7,8,9-tetrahydro-2H-1,2,5,6-tetraazabenzo[cd]azulene | 300 |
| 28 | CH2CH2OH | 2-(2,7,8,9-tetrahydro-6H-1,2,5,6-tetraazabenzo[cd]azulen-6-yl)ethan-1-ol | 219 |
| 29 | tetrahydro-2H-pyran-4-yl | 6-(tetrahydro-2H-pyran-4-yl)-6,7,8,9-tetrahydro-2H-1,2,5,6-tetraazabenzo[cd]azulene | 259 |

Example 30

Examples 30 was prepared similarly to Example 16 replacing intermediate 7 with the appropriate intermediate which in turn was prepared by replacing methanamine with the appropriate amine in Step 3, Example 1 and replacing methyl acrylate with methyl methacrylate in Step 4, Example 1 as shown below.

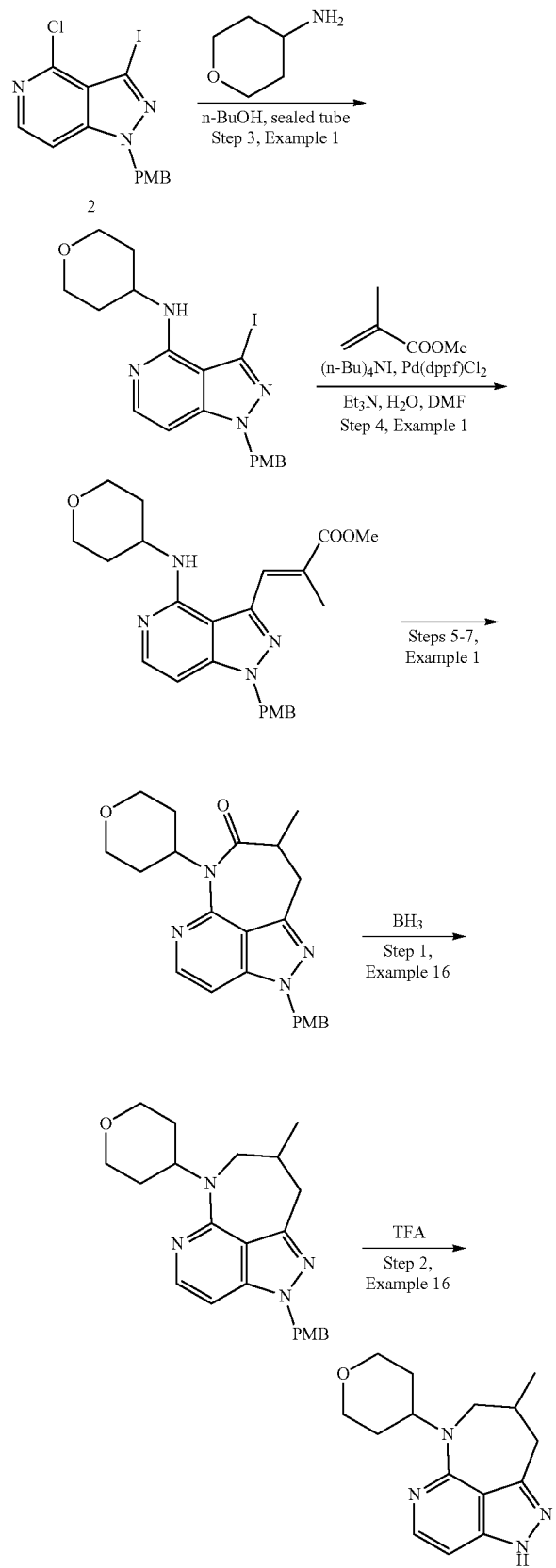

Example 30

| Example | Structure | Name | m/z (ESI)+ [M + H] |
|---|---|---|---|
| 30 | 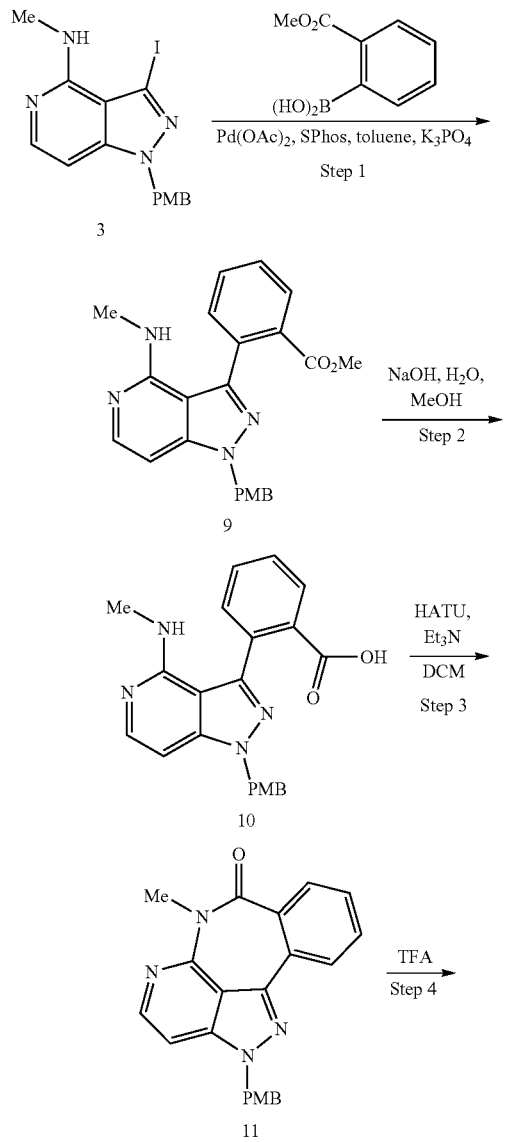 | 8-methyl-6-(tetrahydro-2H-pyran-4-yl)-6,7,8,9-tetrahydro-2H-1,2,5,6-tetraazabenzo[cd]azulene | 273 |

Example 31

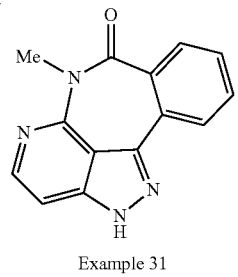

Example 31

Step 1 Synthesis of methyl 2-(4-(methylamino)-1-(4-methoxybenzyl)-1H-pyrazolo[4,3-c]pyridin-3-yl) benzoate (Intermediate 9)

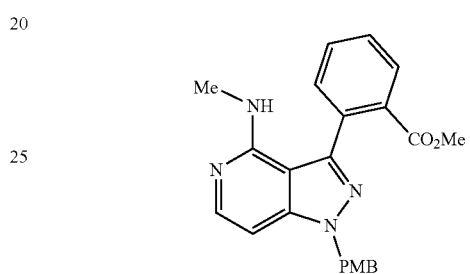

A mixture of intermediate 3 (1.8 g, 4.56 mmol), (2-(methoxycarbonyl)phenyl)boronic acid (1.23 g, 6.85 mmmol) and K$_3$PO$_4$ (1.94 g, 9.13 mmol) in toluene (50 mL) was degassed with Argon and then Pd(OAc)$_2$ (103 mg, 0.46 mmol) was added. The mixture was transferred to a sealed bomb and heated to 95° C. for 16 h. After concentration, the residue was partitioned between EtOAc (300 mL) and water (150 mL). The organic layer was washed with water (100 mL×2), dried with anhydrous Na$_2$SO$_4$, filtered and concentrated to dryness. The residue was purified with flash chromatography, eluting with 0 to 65% EtOAc/PE gradient, to give a light yellow foam (1.44 g, 78%). $^1$H NMR (400 MHz, DMSO-d$_6$) δ ppm 2.80 (d, J=8.8 Hz, 3H), 3.44 (s, 3H), 3.70 (s, 3H), 5.11 (m, 1H), 5.46 (s, 2H), 6.90 (m, 3H), 7.18 (d, J=8.8 Hz, 2H), 7.55 (d, J=7.6 Hz, 1H), 7.62 (t, J=7.6 Hz, 1H), 7.71 (t, J=7.6 Hz, 1H), 7.81 (d, J=6.0 Hz, 1H), 7.88 (d, J=7.6 Hz, 1H); m/z (ESI)$^+$: 403[M+H]$^+$.

Step 2 Synthesis of 2-(4-(ethylamino)-1-(4-methoxybenzyl)-1H-pyrazolo[4,3-c]pyridin-3-yl) Benzoic Acid (Intermediate 10)

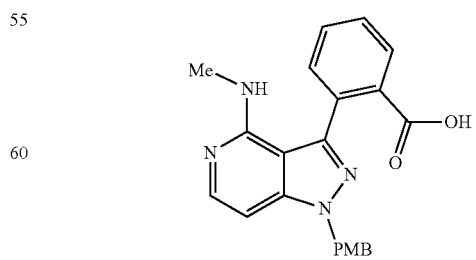

To a solution of intermediate 9 (1.438 g, 3.55 mmol) in methanol (20 mL) and water (5 mL) at room temperature was added NaOH (700 mg, 17.78 mmol). The resulting mixture was stirred at 45° C. for 4 h and the pH value of the mixture was adjusted to 4 with acetic acid. After evaporating, the residue was purified with flash chromatography, eluting with 0 to 30% methanol/DCM gradient, to give a white solid (1.3 g, 93%). $^1$H NMR (400 MHz, DMSO-$d_6$) δ ppm 3.00 (d, J=4.8 Hz, 3H), 3.71 (s, 3H), 5.62 (s, 2H), 6.89 (d, J=8.4 Hz, 2H), 7.22 (d, J=8.4 Hz, 3H), 7.38 (d, J=7.2 Hz, 1H), 7.48 (d, J=7.2 Hz, 1H), 7.69 (m, 3H), 8.02 (d, J=6.8 Hz, 1H), 13.20 (br s, 1H); m/z (ESI)$^+$: 389 [M+H]$^+$.

Step 3 Synthesis of 11-(4-methoxybenzyl)-4-methyl-4,11-dihydro-5H-3,4,10,11-tetraazadibenzo[cd,h]azulen-5-one (Intermediate 11)

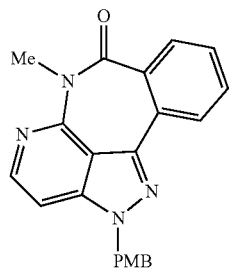

To a mixture of intermediate 10 (1.3 g, 3.34 mmol) and HATU (1.9 g, 5.02 mmol) in dry DCM (40 mL) under Argon, was added Et$_3$N (1.02 g, 10.05 mmol). After stirring at room temperature for 16 h, the reaction mixture was evaporated and the residue was purified with flash chromatography, eluting with 0 to 30% EtOAc/PE gradient, to give a white solid (1.11 g, 90%). $^1$H NMR (400 MHz, DMSO-$d_6$) δ ppm 3.64 (s, 3H), 3.70 (s, 3H), 5.61 (s, 2H), 6.89 (d, J=8.4 Hz, 2H), 7.29 (d, J=8.4 Hz, 2H), 7.39 (d, J=6.0 Hz, 1H), 7.51 (t, J=7.6 Hz, 1H), 7.67 (t, J=7.4 Hz, 1H), 8.10 (d, J=6.0 Hz, 1H), 8.31 (m, 2H); m/z (ESI)$^+$: 371 [M+H]$^+$.

Step 4 Synthesis of 4-methyl-4,11-dihydro-5H-3,4,10,11-tetraazadibenzo[cd,h]azulen-5-one (Example 31)

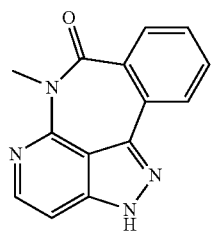 [SMILES: CN1C(=O)c2ccccc2-c2n[nH]c3ccnc1c23]

The solution of intermediate 11 (50 mg, 0.135 mmol) in TFA (3 mL) was heated to 90° C. for 6 h, and then evaporated under vacuum and purified with a flash chromatography, eluting with 0 to 30% methanol/DCM gradient, to give a white solid (45%). $^1$H NMR (400 MHz, DMSO-$d_6$) δ ppm 3.66 (s, 3H), 7.16 (d, J=6.0 Hz, 1H), 7.52 (t, J=5.6 Hz, 1H), 7.69 (t, J=5.2 Hz, 1H), 8.08 (d, J=6.4 Hz, 1H), 8.35 (m, 2H), 13.73 (s, 1H). m/z (ESI)$^+$: 251 [M+H]$^+$.

Examples 32-44

Examples 32-44 were prepared similarly to Example 31 replacing intermediate 3 with the appropriate intermediates which in turn were prepared by replacing methanamine with the appropriate amine in Step 3, Example 1 as shown below.

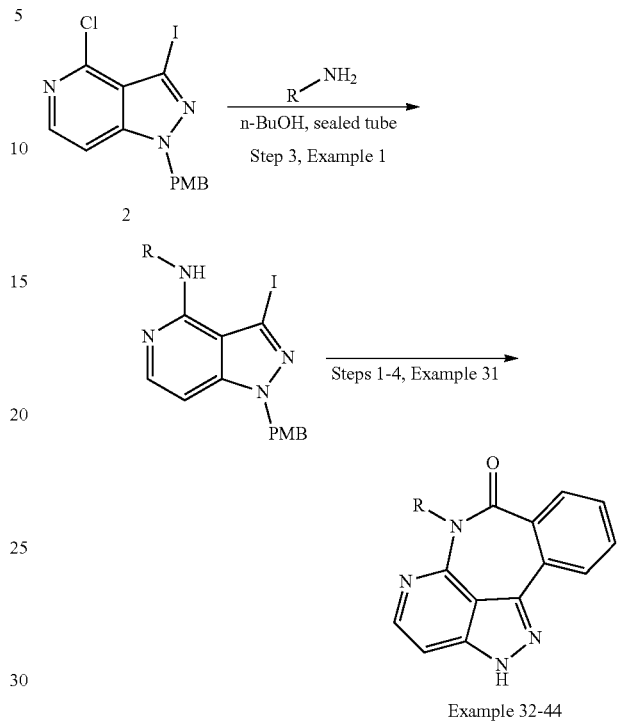

| Example | R | Name | m/z (ESI)$^+$ [M + H] |
|---|---|---|---|
| 32 | C$_2$H$_5$ | 4-ethyl-4,11-dihydro-5H-3,4,10,11-tetraazadibenzo[cd,h]azulen-5-one | 265 |
| 33 | cyclopropyl | 4-cyclopropyl-4,11-dihydro-5H-3,4,10,11-tetraazadibenzo[cd,h]azulen-5-one | 277 |
| 34 | isopropyl | 4-isopropyl-4,11-dihydro-5H-3,4,10,11-tetraazadibenzo[cd,h]azulen-5-one | 279 |
| 35 | isobutyl | 4-isopropyl-4,11-dihydro-5H-3,4,10,11-tetraazadibenzo[cd,h]azulen-5-one | 293 |
| 36 | sec-butyl | 4-(sec-butyl)-4,11-dihydro-5H-3,4,10,11-tetraazadibenzo[cd,h]azulen-5-one | 293 |
| 37 | cyclobutyl | 4-cyclobutyl-4,11-dihydro-5H-3,4,10,11-tetraazadibenzo[cd,h]azulen-5-one | 291 |
| 38 | cyclopentyl | 4-cyclopentyl-4,11-dihydro-5H-3,4,10,11-tetraazadibenzo[cd,h]azulen-5-one | 305 |

-continued

| Example | R | Name | m/z (ESI)+ [M + H] |
|---|---|---|---|
| 39 | 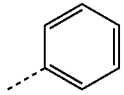 | 4-phenyl-4,11-dihydro-5H-3,4,10,11-tetraazadibenzo[cd,h]azulen-5-one | 313 |
| 40 | Bn | 4-benzyl-4,11-dihydro-5H-3,4,10,11-tetraazadibenzo[cd,h]azulen-5-one | 327 |
| 41 |  | 4-(1-methylpiperidin-4-yl)-4,11-dihydro-5H-3,4,10,11-tetraazadibenzo[cd,h]azulen-5-one | 334 |
| 42 | 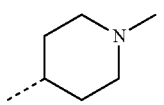 | 4-(1-isopropylpiperidin-4-yl)-4,11-dihydro-5H-3,4,10,11-tetraazadibenzo[cd,h]azulen-5-one | 362 |
| 43 | 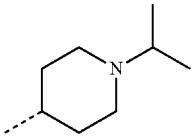 OH | 4-(2-hydroxyethyl)-4,11-dihydro-5H-3,4,10,11-tetraazadibenzo[cd,h]azulen-5-one | 281 |
| 44 | 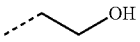 | 4-(tetrahydro-2H-pyran-4-yl)-4,11-dihydro-5H-3,4,10,11-tetraazadibenzo[cd,h]azulen-5-one | 321 |

Example 45

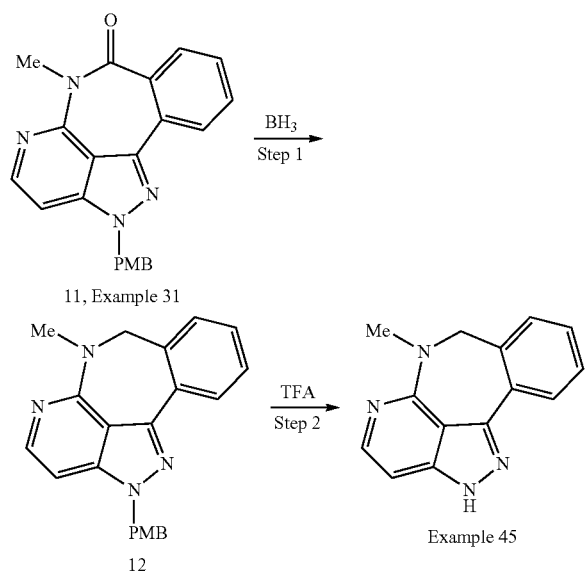

Synthesis of 4-methyl-5,11-dihydro-4H-3,4,10,11-tetraazadibenzo[cd,h]azulene (Example 45)

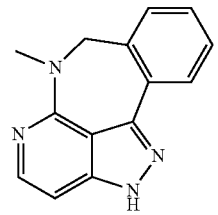 [SMILES: CN1Cc2ccccc2-c2n[nH]c3ccnc1c23]

To a solution of intermediate 11 (260 mg, 0.70 mmol) in example 31 in dry THF (15 mL) under Argon, was added BH$_3$ (1.6 M in THF, 4 mL) at 0° C. The mixture was left to stir at room temperature for 3 h, and then quenched with the addition of methanol (6 mL) and concentrated to dryness. The crude product 12 was dissolved in TFA (5 mL) and stirred at 90° C. in a sealed bomb overnight. After cooling to room temperature, the mixture was concentrated under vacuum and the residue was dissolved in DCM/MeOH (1:1, v/v, 10 mL), neutralized with K$_2$CO$_3$, filtered and concentrated. The residue was purified with flash chromatography, eluting with 0 to 35% methanol/DCM gradient, and then purified with a reversed-phase C-18 column, eluting with 5 to 70% MeCN/water gradient, to give an off-white solid (36% for two steps). $^1$H NMR (400 MHz, DMSO-d$_6$) δ ppm 3.33 (s, 3H), 4.86 (s, 2H), 7.06 (s, 1H), 7.50 (m, 2H), 7.62 (d, J=6.8 Hz, 1H), 7.73 (d, J=6.4 Hz, 1H), 8.02 (d, J=7.2 Hz, 1H), 12.68 (br s, 1H); m/z (ESI)$^+$: 237 [M+H]$^+$.

Examples 46-58

Examples 46-58 were prepared similarly to Example 45 according to the scheme below.

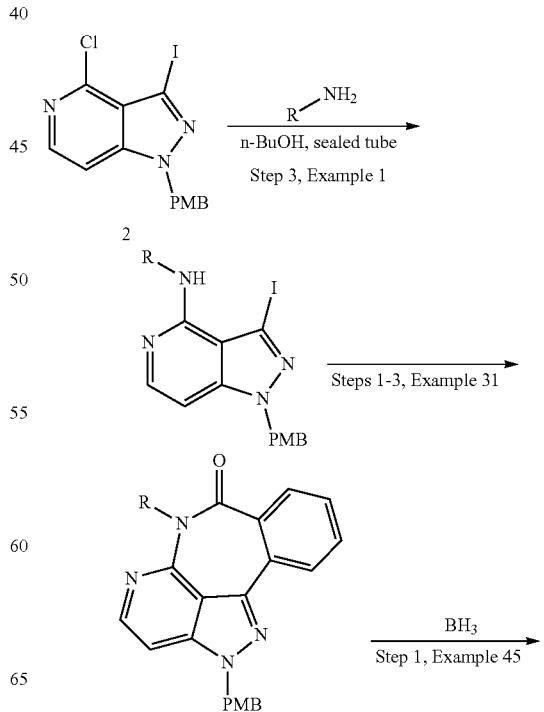

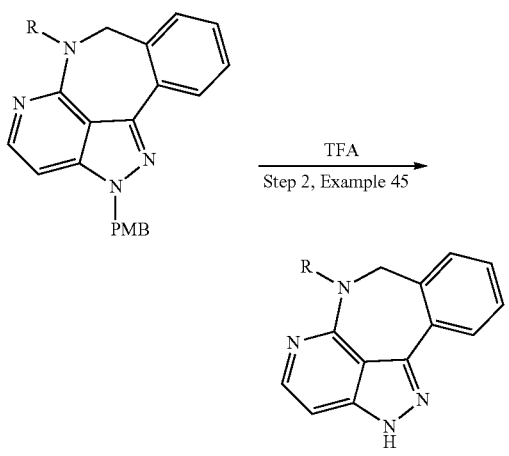

Examples 46-58

| Example | R | Name | m/z (ESI)+ [M + H] |
|---|---|---|---|
| 46 | C₂H₅ | 4-ethyl-5,11-dihydro-4H-3,4,10,11-tetraazadibenzo[cd,h]azulene | 251 |
| 47 | cyclopropyl | 4-cyclopropyl-5,11-dihydro-4H-3,4,10,11-tetraazadibenzo[cd,h]azulene | 263 |
| 48 | isopropyl | 4-isopropyl-5,11-dihydro-4H-3,4,10,11-tetraazadibenzo[cd,h]azulene | 265 |
| 49 | isobutyl | 4-isobutyl-5,11-dihydro-4H-3,4,10,11-tetraazadibenzo[cd,h]azulene | 279 |
| 50 | sec-butyl | 4-(sec-butyl)-5,11-dihydro-4H-3,4,10,11-tetraazadibenzo[cd,h]azulene | 279 |
| 51 | cyclobutyl | 4-cyclobutyl-5,11-dihydro-4H-3,4,10,11-tetraazadibenzo[cd,h]azulene | 277 |
| 52 | cyclopentyl | 4-cyclopentyl-5,11-dihydro-4H-3,4,10,11-tetraazadibenzo[cd,h]azulene | 291 |
| 53 | phenyl | 4-phenyl-5,11-dihydro-4H-3,4,10,11-tetraazadibenzo[cd,h]azulene | 299 |
| 54 | Bn | 4-benzyl-5,11-dihydro-4H-3,4,10,11-tetraazadibenzo[cd,h]azulene | 313 |
| 55 | 1-methylpiperidin-4-yl | 4-(1-methylpiperidin-4-yl)-5,11-dihydro-4H-3,4,10,11-tetraazadibenzo[cd,h]azulene | 320 |
| 56 | 1-isopropylpiperidin-4-yl | 4-(1-isopropylpiperidin-4-yl)-5,11-dihydro-4H-3,4,10,11-tetraazadibenzo[cd,h]azulene | 348 |
| 57 | (CH₂)₂OH | 2-(5,11-dihydro-4H-3,4,10,11-tetraazadibenzo[cd,h]azulen-4-yl)ethan-1-ol | 267 |
| 58 | tetrahydro-2H-pyran-4-yl | 4-(tetrahydro-2H-pyran-4-yl)-5,11-dihydro-4H-3,4,10,11-tetraazadibenzo[cd,h]azulene | 307 |

Examples 59, 60

Examples 59, 60 were prepared similarly to Example 44, according to the following scheme, replacing 2-(methoxycarbonyl)phenylboronic acid with the appropriate phenylboronic acid at Step 1, Example 31 and replacing methanamine with tetrahydro-2H-pyran-4-amine in Step 3, Example 1.

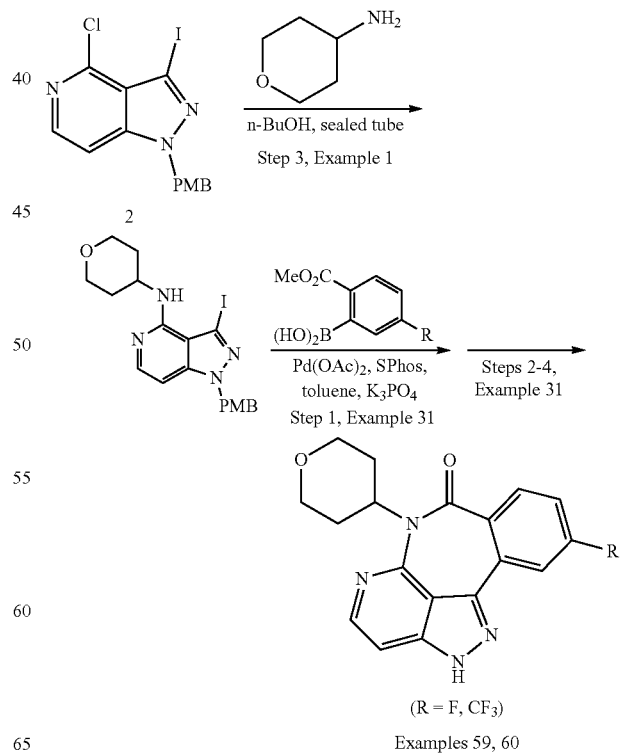

(R = F, CF₃)

Examples 59, 60

| Example | Structure | Name | m/z (ESI)+ [M + H] |
|---|---|---|---|
| 59 | 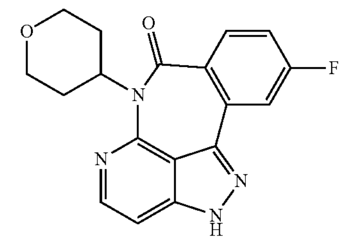 [SMILES: O=C1c2ccc(F)cc2-c2n[nH]c3ccnc(c23)N1C1CCOCC1] | 8-fluoro-4-(tetrahydro-2H-pyran-4-yl)-4,11-dihydro-5H-3,4,10,11-tetraazadibenzo[cd,h]azulen-5-one | 339 |
| 60 | 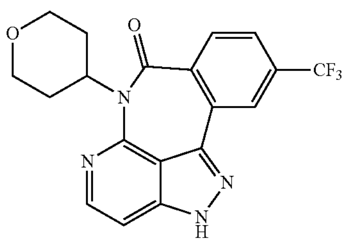 [SMILES: O=C1c2ccc(C(F)(F)F)cc2-c2n[nH]c3ccnc(c23)N1C1CCOCC1] | 4-(tetrahydro-2H-pyran-4-yl)-8-(trifluoromethyl)-4,11-dihydro-5H-3,4,10,11-tetraazadibenzo[cd,h]azulen-5-one | 389 |

Examples 61, 62

Examples 61, 62 were prepared similarly to Example 58 according to the scheme below, replacing intermediate 11, Example 45, with the appropriate intermediates which was made in turn by replacing 2-(methoxycarbonyl)phenylboronic acid with the appropriate phenyl boric acid at Step 1, Example 31 and replacing methanamine with tetrahydro-2H-pyran-4-amine in Step 3, Example 1.

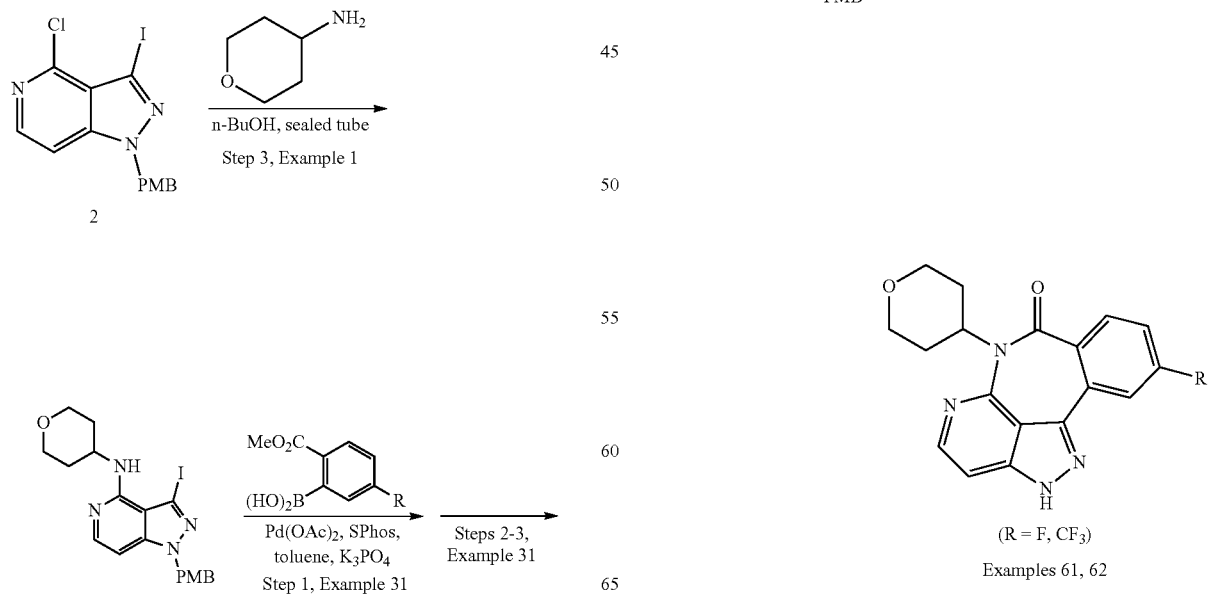

| Example | Structure | Name | m/z (ESI)+ [M + H] |
|---|---|---|---|
| 61 | 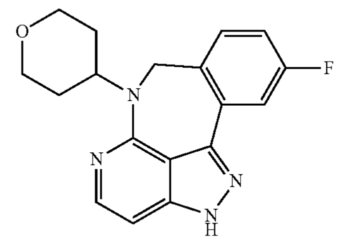 [SMILES: Fc1ccc2c(c1)-c1n[nH]c3ccnc(c13)N(C1CCOCC1)C2] | 8-fluoro-4-(tetrahydro-2H-pyran-4-yl)-5,11-dihydro-4H-3,4,10,11-tetraazadibenzo[cd,h]azulene | 325 |
| 62 | 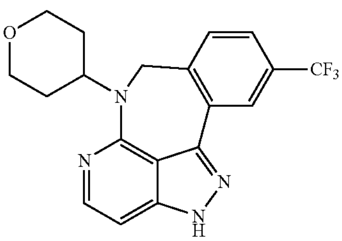 [SMILES: FC(F)(F)c1ccc2c(c1)-c1n[nH]c3ccnc(c13)N(C1CCOCC1)C2] | 4-(tetrahydro-2H-pyran-4-yl)-8-(trifluoromethyl)-5,11-dihydro-4H-3,4,10,11-tetraazadibenzo[cd,h]azulene | 375 |
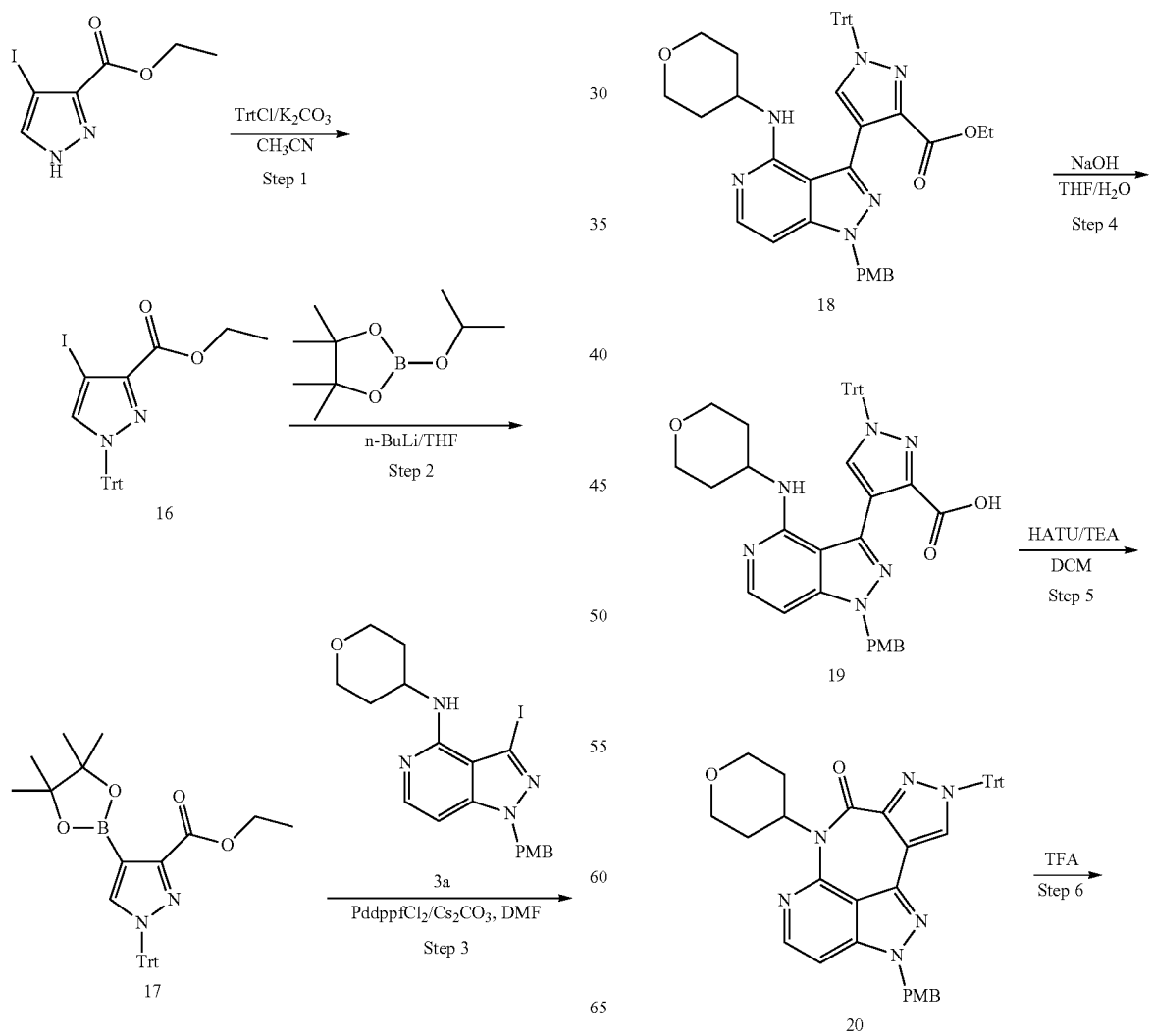

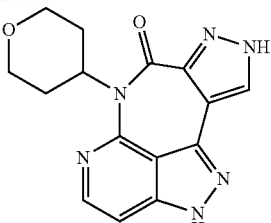

Example 65

Step 1 Synthesis of ethyl
4-iodo-1-trityl-1H-pyrazole-3-carboxylate
(Intermediate 16)

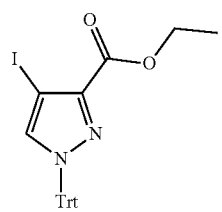

A mixture of ethyl 4-iodo-1H-pyrazole-3-carboxylate (8.0 g, 30.0 mmol), K₂CO₃ (12.42 g, 90.0 mmol) and TrtCl (10.06 g, 36.0 mmol) in MeCN (200 mL) was heated to 90° C. for 15 h. After cooling to room temperature, the solid in the mixture was filtered out and the filtered cake was washed with ethyl acetate (100 mL). The combined solutions were evaporated under vacuum and the residue was purified with flash chromatography, eluting with 0 to 15% EtOAc/PE gradient, to give white crystals (10.0 g, 67%). ¹H NMR (400 MHz, DMSO-d₆) δ ppm 1.28 (t, J=7.2 Hz, 3H), 4.27 (m, J=7.2 Hz, 2H), 7.02 (m, 6H), 7.29-7.50 (m, 9H), 7.56 (s, 1H).

Step 2 Synthesis of ethyl 4-(4,4,5,5-tetramethyl-1,3,2-dioxaborolan-2-yl)-1-trityl-1H-pyrazole-3-carboxylate (Intermediate 17)

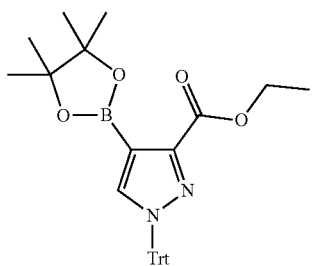

A solution of intermediate 16 (2.1 g, 4.13 mmol) and 2-isopropoxy-4,4,5,5-tetramethyl-1,3,2-dioxaborolane (2.31 g, 12.40 mmol) in dry THF (20 mL) was cooled to −75° C. under Argon, then n-BuLi (7.75 mL, 12.40 mmol, 1.6 M in hexane) was added dropwise to keep the temperature of the mixture below −70° C. After stirring at −75° C. for 1 h, the reaction mixture was quenched with the addition of water and then the mixture was partitioned between water and EtOAc. The organic layer was washed with NH₄Cl (saturated, 100 mL), water (100 mL) and brine (100 mL), dried (Na₂SO₄) and evaporated to dryness. The residue was purified with flash chromatography, eluting with 0 to 30% EtOAc/PE gradient, to give white crystals (0.5 g, 24%). ¹H NMR (400 MHz, DMSO-d₆) δ ppm: 1.23 (s, 12H), 1.28 (t, J=5.2 Hz, 3H), 4.24 (q, J=5.2 Hz, 2H), 7.04 (m, 6H), 7.39 (m, 9H), 7.47 (s, 1H).

Step 3 Synthesis of ethyl 4-(1-(4-methoxybenzyl)-4-(tetrahydro-2H-pyran-4-ylamino)-1H-pyrazolo[4,3-c]pyridin-3-yl)-1-trityl-1H-pyrazole-3-carboxylate (Intermediate 18)

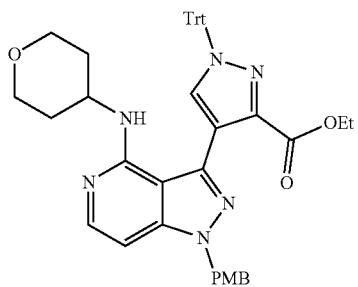

A mixture of intermediate 3a (3.25 g, 7.0 mmol, prepared similarly to intermediate 3 in example 1 by replacing methanamine with tetrahydro-2H-pyran-4-amine in Step 3) and intermediate 17 (3.92 g, 7.7 mmol), Cs₂CO₃ (6.85 g, 21 mmol), Pd(dppf)Cl₂ in dry DMF (20 mL) was sealed in a bomb under Argon. The mixture was stirred at 90° C. for 16 h and cooled to room temperature and NH₄Cl solution (saturated, 200 mL) was added to the reaction mixture. After extracting with ethyl acetate (3×150 mL), the combined organic layers were washed with NH₄Cl solution (saturated, 150 mL), dried (Na₂SO₄) and concentrated to dryness. The residue was purified with flash chromatography, eluting with 0% to 80% EtOAc/PE gradient, to give a white solid (3.0 g, 60%). ¹H NMR (400 MHz, DMSO-d₆) δ ppm 0.67 (t, J=6.8 Hz, 3H), 1.15 (m, 2H), 1.80 (m, 2H), 3.40 (m, 2H), 3.72 (m, 5H), 3.95 (m, 2H), 4.06 (m, 1H), 4.72 (d, J=7.6 Hz, 2H), 5.46 (s, 2H), 6.86 (m, 3H), 7.16 (m, 8H), 7.42 (m, 10H), 7.75 (m, 2H). m/z (ESI)⁺: 719 [M+H]⁺.

Step 4 Synthesis of 4-(1-(4-methoxybenzyl)-4-(tetrahydro-2H-pyran-4-ylamino)-1H-pyrazolo[4,3-c]pyridin-3-yl)-1-trityl-1H-pyrazole-3-carboxylic Acid (Intermediate 19)

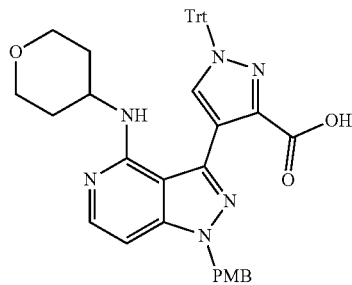

A mixture of intermediate 18 (3.0 g, 4.34 mmol) and NaOH (0.87 g, 21.71 mmol) in THF/H₂O (1:1, v/v, 16 mL) was stirred at 50° C. for 60 h and cooled to room temperature. The THF in the mixture was removed under vacuum and the pH value of the mixture was adjusted to 3 with HCl (1 N). The mixture was extracted with DCM (100 mL×3) and the organic layers were combined, dried (Na₂SO₄) and concentrated to give a crude product (2.5 g), which was applied to the next step directly with no further purification. m/z (ESI)⁺: 691 [M+H]⁺.

Step 5 Synthesis of 5-(4-methoxybenzyl)-9-(tetra-hydro-2H-pyran-4-yl)-2-trityl-5,9-dihydro-1,2,4,5,8,9-hexaazabenzo[cd]cyclopenta[h]azulen-10(2H)-one (Intermediate 20)

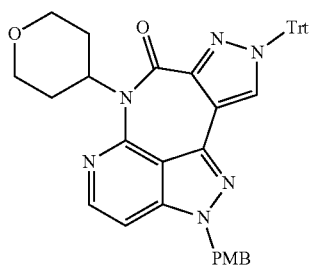

A mixture of intermediate 19 (2.5 g, 3.26 mmol), HATU (2.06 g, 5.43 mmol) and TEA in CH₂Cl₂ (50 mL) was stirred at rt for 16 h and then the mixture was concentrated to dryness and the residue was purified with flash chromatography, eluting with 0% to 80% EtOAc/PE gradient, to give a white solid (3.0 g, 60%). ¹H NMR (400 MHz, DMSO-d₆) δ ppm 1.60 (d, J=10.4 Hz, 2H), 2.80 (m, 2H), 3.40 (m, 2H), 3.69 (s, 3H), 3.97 (m, 2H), 5.51 (s, 2H), 5.67 (m, 1H), 6.86 (d, J=8.8 Hz, 2H), 7.18 (m, 8H), 7.41 (m, 10H), 7.75 (s, 1H), 8.15 (d, J=6.0 Hz, 1H). m/z (ESI)⁺: 673 [M+H]⁺.

Step 6 Synthesis of 9-(tetrahydro-2H-pyran-4-yl)-5,9-dihydro-1,2,4,5,8,9-hexaazabenzo[cd]cyclopenta[h]azulen-10(2H)-one (Example 65)

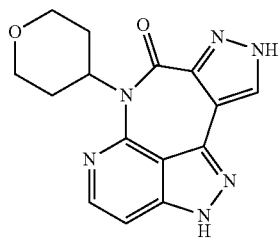 [SMILES: O=C1c2n[nH]cc2-c2n[nH]c3ccnc(c23)N1C1CCOCC1]

A mixture of intermediate 20 (50 mg, 0.080 mmol), TFA (3 mL) in a sealed bomb was stirred at 90° C. for 16 h. The mixture was concentrated under vacuum and the residue was purified with flash chromatography, using a reversed-phase C-18 column and eluting with 5% to 60% acetonitrile/water gradient, to give a white solid (12 mg, 60%). ¹H NMR (400 MHz, DMSO-d₆) δ ppm 1.62 (m, 2H), 2.84 (m, 2H), 3.76 (m, 2H), 3.98 (m, 2H), 5.81 (m, 1H), 7.15 (d, J=5.6 Hz, 1H), 8.05 (s, 1H), 8.09 (d, J=5.6 Hz, 1H), 13.41 (s, 1H), 14.01 (s, 1H). m/z (ESI)⁺: 311 [M+H]⁺.

Examples 66 and 67

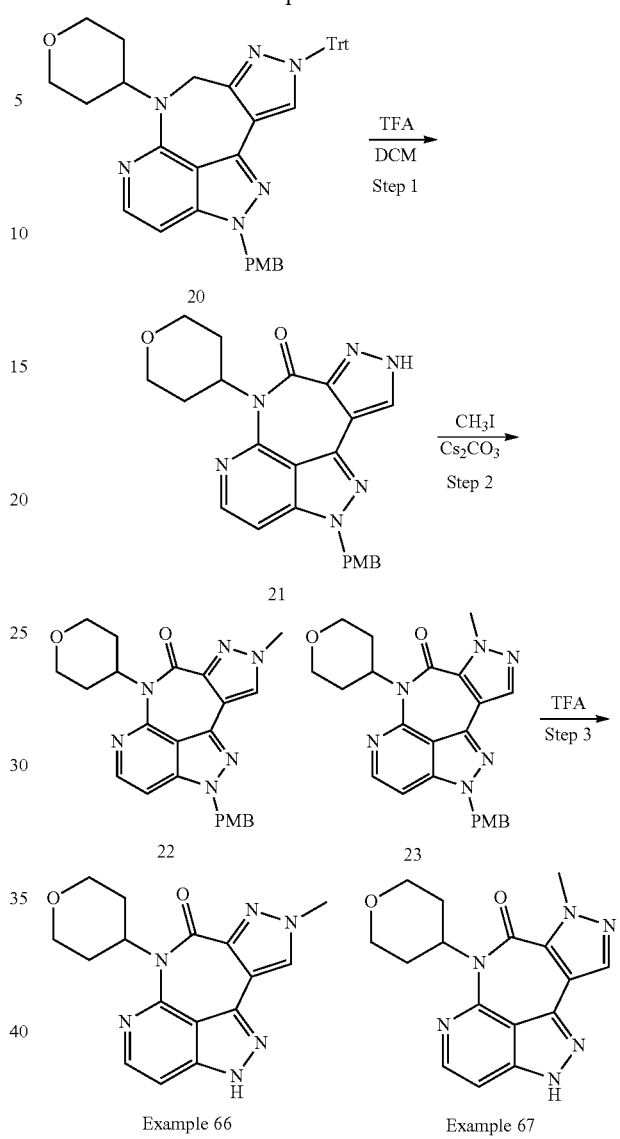

Step 1

Synthesis of 5-(4-methoxybenzyl)-9-(tetrahydro-2H-pyran-4-yl)-2-trityl-5,9-dihydro-1,2,4,5,8,9-hexaazabenzo[cd]cyclopenta[h]azulen-10(2H)-one (Intermediate 21)

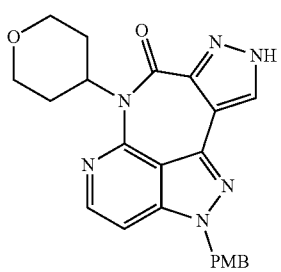

A solution of intermediate 20 (1.0 g, 1.49 mmol) in example 65 in CH$_2$Cl$_2$/TFA (22 mL, 10:1, v/v) was stirred at room temperature for 3 h. The reaction mixture was quenched with Na$_2$CO$_3$ solution (saturated, 50 mL) and CH$_2$Cl$_2$ in the mixture was evaporated under vacuum. The solid in the mixture was collected by filtration and washed with water (20 mL×3) to give a white solid (0.42 g, 66%), which was applied to the next step directly with no further purification. m/z (ESI)$^+$: 431 [M+H]$^+$.

Step 2

Synthesis of 5-(4-methoxybenzyl)-2-methyl-9-(tetrahydro-2H-pyran-4-yl)-5,9-dihydro-1,2,4,5,8,9-hexaazabenzo[cd]cyclopenta[h]azulen-10(2H)-one (Intermediate 22) and 5-(4-methoxybenzyl)-1-methyl-9-(tetrahydro-2H-pyran-4-yl)-5,9-dihydro-1,2,4,5,8,9-hexaazabenzo[cd]cyclopenta[h]azulen-10(1H)-one (Intermediate 23)

22

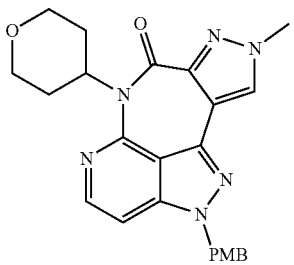

23

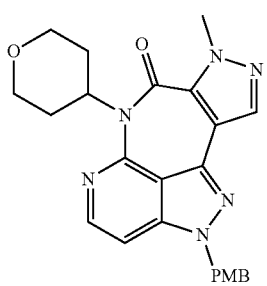

To a mixture of intermediate 21 (220 mg, 0.51 mmol) and Cs$_2$CO$_3$ (333 mg, 1.02 mmol) in dry DMF (5 mL) was added CH$_3$I (145 mg, 1.02 mmol) at room temperature in a sealed bomb. After stirring at 60° C. for 5 h, the mixture was cooled to room temperature and poured into aqueous NH$_4$Cl (saturated, 20 mL), and then extracted with EA (30 mL×3). The combined organic layers were washed with brine (20 mL×3), dried with anhydrous Na$_2$SO$_4$, and concentrated to dryness. The crude product (200 mg, white solid) as a mixture of intermediate 22 and 23 was applied to the next step directly with no further purification. m/z (ESI)$^+$: 445 [M+H]$^+$.

Step 3

Synthesis of 2-methyl-9-(tetrahydro-2H-pyran-4-yl)-5,9-dihydro-1,2,4,5,8,9-hexaazabenzo[cd]cyclopenta[h]azulen-10(2H)-one (Example 66) and 1-methyl-9-(tetrahydro-2H-pyran-4-yl)-5,9-dihydro-1,2,4,5,8,9-hexaazabenzo[cd]cyclopenta[h]azulen-10(1H)-one (Example 67)

Example 66

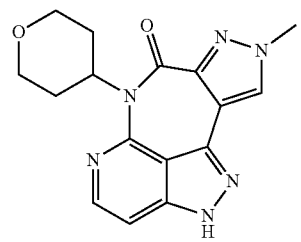

Example 67

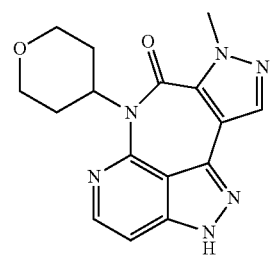

A mixture of intermediates 22 and 23 (200 mg, 0.45 mmol) and TFA (5 mL) in a sealed bomb was stirred at 90° C. for 16 h. The mixture was concentrated under vacuum and the residue was purified with flash chromatography using a reverse-phase C-18 column and eluting with 5% to 50% acetonitrile/water gradient to give 20 mg of example 66 and 42 mg of example 67.

Compound 66: $^1$H NMR (400 MHz, DMSO-d$_6$) δ ppm 1.63 (m, 2H), 2.80 (m, 2H), 3.46 (m, 2H), 3.94 (m, 2H), 4.13 (s, 3H), 5.71 (m, 1H), 7.10 (d, J=5.6 Hz, 1H), 7.97 (s, 1H), 8.06 (d, J=5.6 Hz, 1H), 13.41 (s, 1H). m/z (ESI)$^+$: 325 [M+H]$^+$.

Compound 67: $^1$H NMR (400 MHz, DMSO-d$_6$) δ ppm 1.61 (m, 2H), 2.80 (m, 2H), 3.45 (m, 2H), 3.95 (m, 5H), 5.63 (m, 1H), 7.11 (d, J=5.6 Hz, 1H), 8.07 (d, J=5.6 Hz, 1H), 8.35 (s, 1H), 13.37 (s, 1H). m/z (ESI)$^+$: 325 [M+H]$^+$.

Example 68

Synthesis of Pyrazole Boron Esters:

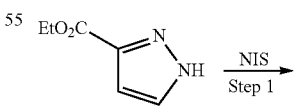

24

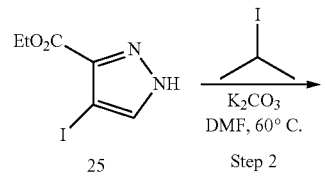

25

Step 2

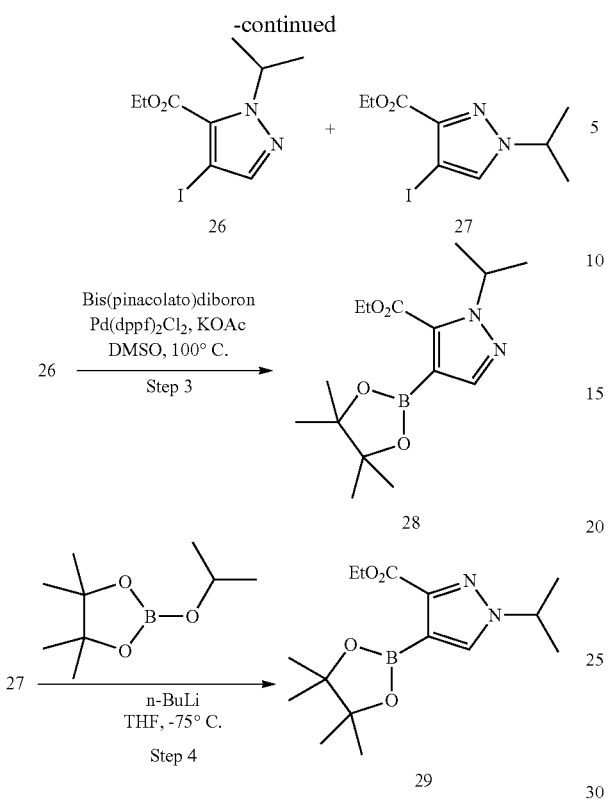

Step 1

Synthesis of ethyl 4-iodo-1H-pyrazole-3-carboxylate (25)

To a solution of ethyl 1H-pyrazole-3-carboxylate (10.0 g, 71.4 mmol) in DCM (30 mL) was added NIS (22.5 g, 100 mmol) at room temperature. The mixture was stirred for 24 hours. Then the reaction was quenched with $H_2O$ (50 mL) and the mixture was extracted with EtOAc (60 mL×3). The combined organic phase was washed with brine (50 mL×3) and dried over $Na_2SO_4$. After filtration, the filtrate was concentrated in vacuo. The residue was purified by chromatography (PE:EtOAc=1:5, v/v) to give the product ethyl 4-iodo-1H-pyrazole-3-carboxylate (15.5 g, 82%). m/z (ESI)$^+$: 267 [M+H]$^+$.

Step 2

Synthesis of ethyl 4-iodo-1-isopropyl-1H-pyrazole-5-carboxylate (26) and ethyl 4-iodo-1-isopropyl-1H-pyrazole-3-carboxylate (27)

To a solution of ethyl 4-iodo-1H-pyrazole-3-carboxylate (15.53 g, 58.4 mmol) in DMF (150 mL) was added 2-iodopropane (12.9 g, 75.9 mmol) and $K_2CO_3$ (16.0 g, 116 mmol). The mixture was heated to 60° C. for 3 hours. Then the reaction was quenched with water (300 mL) and the mixture was extracted with EtOAc (200 mL×3). The combined organic was washed with brine (200 mL×3) and dried over $Na_2SO_4$. After filtration, the organic phase was concentrated in vacuo. The residue was purified by chromatography (PE:EtOAc=10:1, v/v) to give the intermediate 26 ethyl 4-iodo-1-isopropyl-1H-pyrazole-5-carboxylate (9.4 g, 52%), m/z (ESI)$^+$: 309 [M+H]$^+$, and with PE:EtOAc=8:1 (v/v) to give the intermediate 27 ethyl 4-iodo-1-isopropyl-1H-pyrazole-3-carboxylate (6.1 g, 33%). m/z (ESI)$^+$: 309 [M+H]$^+$.

Step 3

Synthesis of ethyl 1-isopropyl-4-(4,4,5,5-tetramethyl-1,3,2-dioxaborolan-2-yl)-1H-pyrazole-5-carboxylate (28)

To a solution of ethyl 4-iodo-1-isopropyl-1H-pyrazole-5-carboxylate (2.14 g, 6.95 mmol) in DMSO (20 mL) was added 4,4,4',4',5,5,5',5'-octamethyl-2,2'-bi(1,3,2-dioxaborolane) (3.56 g, 14.0 mmol), KOAc (2.7 g, 27.5 mmol) and Pd(dppf)$_2$Cl$_2$ (300 mg). The mixture was heated to 100° C. for 2 hours. Then the reaction was quenched with $H_2O$ (40 mL) and extracted with EtOAc (40 mL×3). Then the combined organic phase was washed with brine (40 mL×3) and dried over $Na_2SO_4$. After filtration, the filtrate was concentrated in vacuo. The residue was purified by chromatography (PE:EtOAc=10:1, v/v) to give the product ethyl 1-isopropyl-4-(4,4,5,5-tetramethyl-1,3,2-dioxaborolan-2-yl)-1H-pyrazole-5-carboxylate (1.0 g, 93%). m/z (ESI)$^+$: 309 [M+H]$^+$.

Step 4

Synthesis of ethyl 1-isopropyl-4-(4,4,5,5-tetramethyl-1,3,2-dioxaborolan-2-yl)-1H-pyrazole-3-carboxylate (29)

A solution of ethyl 4-iodo-1-isopropyl-1H-pyrazole-3-carboxylate (4.5 g, 14.6 mmol) and 2-isopropoxy-4,4,5,5-tetramethyl-1,3,2-dioxaborolane (8.15 g, 43.8 mmol) in dry THF (50 mL) was cooled to −75° C., then n-BuLi (17.5 mL, 1.6 N in hexane, 43.8 mmol) was added dropwise and the mixture was stirred at −75° C. for 2 h, following by the addition of NH$_4$Cl (aq., saturated, 200 mL). The mixture was extracted with ethyl acetate (100 mL×3) and the combined organic layer was washed with brine (50 mL×1), dried (Na$_2$SO$_4$) and evaporated. The crude yellow oil was purified with flash chromatography, eluting with 0 to 40% EtOAc/PE gradient to give a light yellow oil (2.0 g, 44%). $^1$H NMR (400 MHz, DMSO-d$_6$) δ ppm 1.20-1.50 (m, 21H), 4.25 (q, J=7.2 Hz, 2H), 4.51-4.65 (m, 1H), 8.18 (s, 1H); m/z (ESI)$^+$: 309 [M+H]$^+$.

The following pyrazole boron esters can be made similarly as for 28 and 29 using methyl iodide or ethyl iodide in Step 2:

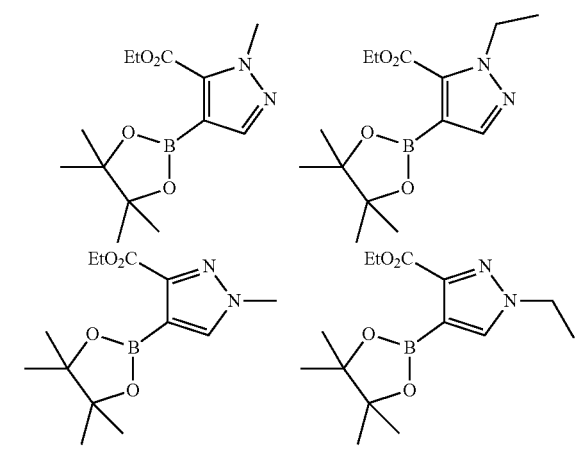

Synthesis of Example 68

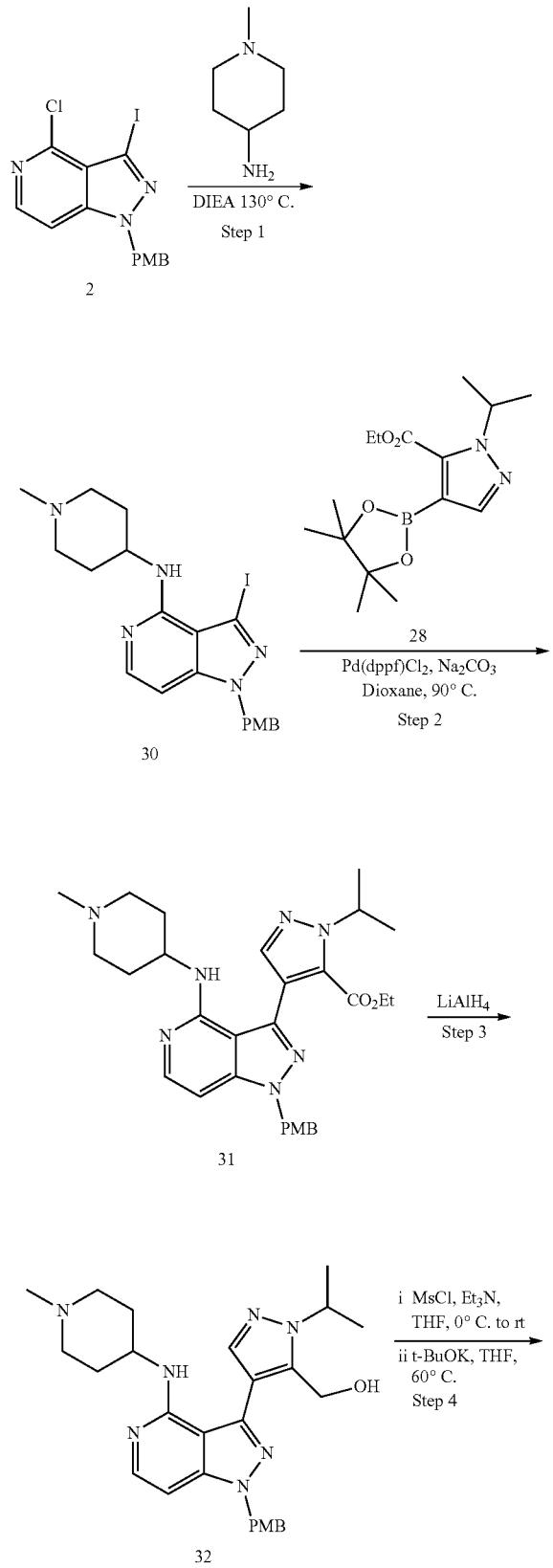

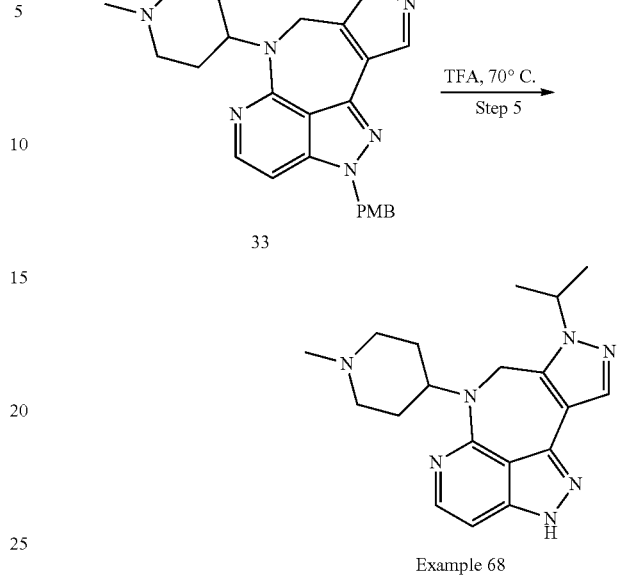

Example 68

Step 1

Synthesis of 3-iodo-1-(4-methoxybenzyl)-N-(1-methylpiperidin-4-yl)-1H-pyrazolo[4,3-c]pyridin-4-amine (30)

Into a 50 mL round-bottom flask, a mixture of 4-chloro-3-iodo-1-(4-methoxybenzyl)-1H-pyrazolo[4,3-c]pyridine (3.0 g, 7.5 mmol), 1-methylpiperidin-4-amine (2.57 g, 22.5 mmol) and DIEA (3.87 g, 30 mmol) was stirred at 130° C. overnight. Then the reaction was concentrated in vacuo and the residue was purified with silica gel chromatography eluting with DCM/MeOH gradient to give the 3-iodo-1-(4-methoxybenzyl)-N-(1-methylpiperidin-4-yl)-1H-pyrazolo[4,3-c]pyridin-4-amine (2.7 g, 75%) as a brown solid. m/z (ESI)$^+$: 478 [M+H]$^+$.

Step 2

Synthesis of ethyl 1-isopropyl-4-(1-(4-methoxybenzyl)-4-((1-methylpiperidin-4-yl)amino)-1H-pyrazolo[4,3-c]pyridin-3-yl)-1H-pyrazole-5-carboxylate (31)

A mixture of 3-iodo-1-(4-methoxybenzyl)-N-(1-methylpiperidin-4-yl)-1H-pyrazolo[4,3-c]pyridin-4-amine (464 mg, 0.97 mmol), ethyl 1-isopropyl-4-(4,4,5,5-tetramethyl-1,3,2-dioxaborolan-2-yl)-1H-pyrazole-5-carboxylate (300 mg, 0.97 mmol), Pd(dppf)Cl$_2$ (80 mg, 0.097 mmol) and 2 N Na$_2$CO$_3$ (1 mL, 2 mmol) in dioxane (20 mL) was stirred at 90° C. under N$_2$ overnight. Then the mixture was diluted with EtOAc (100 mL), washed with water (30 mL×2), brine (30 mL) and dried over Na$_2$SO$_4$. The organic phase was filtered and the filtrate was concentrated to give a residue which was purified by silica gel chromatography eluting with DCM/MeOH=10/1 (v/v) to give ethyl 1-isopropyl-4-(1-(4-methoxybenzyl)-4-((1-methylpiperidin-4-yl)amino)-1H-pyrazolo[4,3-c]pyridin-3-yl)-1H-pyrazole-5-carboxylate (300 mg, 58%) as a yellow oil. m/z (ESI)$^+$: 532 [M+H]$^+$.

Step 3

Synthesis of (1-isopropyl-4-(1-(4-methoxybenzyl)-4-((1-methylpiperidin-4-yl)amino)-1H-pyrazolo[4,3-c]pyridin-3-yl)-1H-pyrazol-5-yl)methanol (32)

To a solution of ethyl 1-isopropyl-4-(1-(4-methoxybenzyl)-4-((1-methylpiperidin-4-yl)amino)-1H-pyrazolo[4,3-c]pyridin-3-yl)-1H-pyrazole-5-carboxylate (510 mg, 0.96 mmol) in dry THF (20 mL) was added LiAlH$_4$ (182 mg, 4.79 mmol) in portions at 0° C. The mixture was stirred at room temperature for 1 hour. Then the reaction was quenched with water (5 mL) and EtOAc (100 mL). The suspension was filtered and the organic phase was separated and washed with brine (15 mL), then dried over Na$_2$SO$_4$. The organic phase was filtered and the filtrate was concentrated in vacuo. The residue was purified by silica gel chromatography eluting with DCM/MeOH=6/1 (v/v) to give (1-isopropyl-4-(1-(4-methoxybenzyl)-4-((1-methylpiperidin-4-yl)amino)-1H-pyrazolo[4,3-c]pyridin-3-yl)-1H-pyrazol-5-yl)methanol (300 mg, 64%) as a white solid. m/z (ESI)$^+$: 490 [M+H]$^+$.

Step 4

Synthesis of 1-isopropyl-5-(4-methoxybenzyl)-9-(1-methylpiperidin-4-yl)-1,5,9,10-tetrahydro-1,2,4,5,8,9-hexaazabenzo[cd]cyclopenta[h]azulene (33)

To a solution of (1-isopropyl-4-(1-(4-methoxybenzyl)-4-((1-methylpiperidin-4-yl)amino)-1H-pyrazolo[4,3-c]pyridin-3-yl)-1H-pyrazol-5-yl)methanol (300 mg, 0.61 mmol) and Et$_3$N (185 mg, 1.84 mmol) in THF (50 mL) was added methanesulfonyl chloride (144 mg, 1.22 mmol) dropwise at 0° C. under N$_2$. Then the reaction was stirred at room temperature for 0.5 hour. TLC showed starting material disappeared. Then t-BuOK (206 mg, 1.84 mmol) was added. The reaction was stirred at 60° C. under N$_2$ for 1 hour. Then the reaction was quenched with water (10 mL) and extracted with EtOAc (100 mL), the organic phase was washed with brine (30 mL), and dried over Na$_2$SO$_4$. The organic phase was filtered and the filtrate was concentrated to give the residue which was purified by silica gel chromatography eluting with DCM/MeOH=6/1 (v/v) to give 1-isopropyl-5-(4-methoxybenzyl)-9-(1-methylpiperidin-4-yl)-1,5,9,10-tetrahydro-1,2,4,5,8,9-hexaazabenzo[cd]cyclopenta[h]azulene (200 mg, 69%) as a colorless oil. m/z (ESI)$^+$: 472 [M+H]$^+$.

Step 5

Synthesis of 1-isopropyl-9-(1-methylpiperidin-4-yl)-1,5,9,10-tetrahydro-1,2,4,5,8,9-hexaazabenzo[cd]cyclopenta[h]azulene (Example 68)

A mixture of 1-isopropyl-5-(4-methoxybenzyl)-9-(1-methylpiperidin-4-yl)-1,5,9,10-tetrahydro-1,2,4,5,8,9-hexaazabenzo[cd]cyclopenta[h]azulene (200 mg, 0.42 mmol) in TFA (5 mL) was stirred at 70° C. overnight. The solvent was removed under reduced pressure. The resultant residue was purified by prep-HPLC. The collected fractions were combined and adjusted to pH=8 with saturated aq. NaHCO$_3$ and extracted with EtOAc (10 mL×3). The organic phase was dried over Na$_2$SO$_4$ and filtered. The filtrate was concentrated in vacuo to give the 1-isopropyl-9-(1-methylpiperidin-4-yl)-1,5,9,10-tetrahydro-1,2,4,5,8,9-hexaazabenzo[cd]cyclopenta[h]azulene (110 mg, 74%) as a white solid. $^1$H NMR (400 MHz, DMSO-d$_6$) δ ppm 1.44 (d, J=6.0 Hz, 6H), 1.63-1.71 (m, 2H), 1.91-2.12 (m, 4H), 2.22-2.32 (m, 3H), 2.92 (s, 2H), 4.47 (s, 2H), 4.62 (m, 1H), 4.93-4.96 (m, 1H), 6.79 (d, J=6.0 Hz, 1H), 7.78-7.81 (m, 2H), 12.95 (br s, 1H); m/z (ESI)$^+$: 352 [M+H]$^+$.

Examples 69-88

Examples 69-88 were prepared similarly to Example 68 using appropriate amines in Step 1 and appropriate pyrazole boron esters in Step 2. For Examples 69 and 76, the appropriate pyrazole boron ester is intermediate 17 in Example 65, Step 2.

| Example | Structure | Name | m/z (ESI)$^+$ [M + H] |
|---|---|---|---|
| 69 | 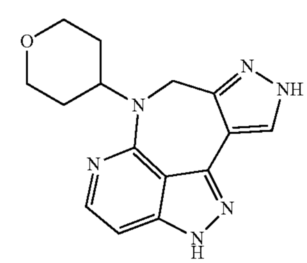 [SMILES: c1cc2[nH]nc3c2c(n1)N(C1CCOCC1)Cc1n[nH]cc1-3] | 9-(tetrahydro-2H-pyran-4-yl)-2,5,9,10-tetrahydro-1,2,4,5,8,9-hexaazabenzo[cd]cyclopenta[h]azulene | 297 |
| 70 | 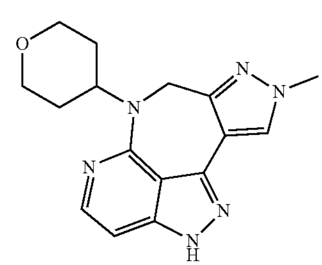 [SMILES: Cn1cc2c(n1)CN(C1CCOCC1)c1nccc3[nH]nc-2c13] | 2-methyl-9-(tetrahydro-2H-pyran-4-yl)-2,5,9,10-tetrahydro-1,2,4,5,8,9-hexaazabenzo[cd]cyclopenta[h]azulene | 311 |

-continued

| Example | Structure | Name | m/z (ESI)+ [M + H] |
|---|---|---|---|
| 71 | 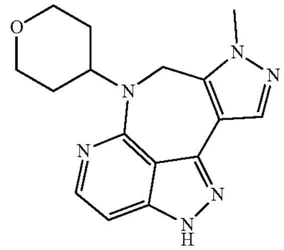 [SMILES: Cn1ncc2c1CN(C1CCOCC1)c1nccc3[nH]nc-2c13] | 1-methyl-9-(tetrahydro-2H-pyran-4-yl)-1,5,9,10-tetrahydro-1,2,4,5,8,9-hexaazabenzo[cd]cyclopenta[h]azulene | 311 |
| 72 | 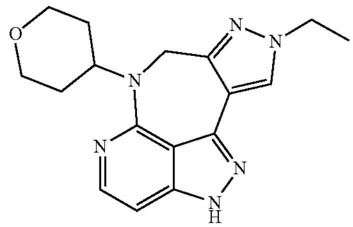 [SMILES: CCn1cc2c(n1)CN(C1CCOCC1)c1nccc3[nH]nc-2c13] | 2-ethyl-9-(tetrahydro-2H-pyran-4-yl)-2,5,9,10-tetrahydro-1,2,4,5,8,9-hexaazabenzo[cd]cyclopenta[h]azulene | 325 |
| 73 | 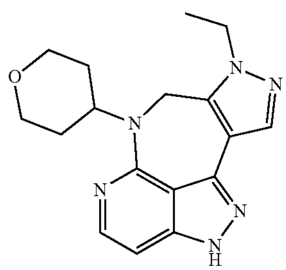 [SMILES: CCn1ncc2c1CN(C1CCOCC1)c1nccc3[nH]nc-2c13] | 1-ethyl-9-(tetrahydro-2H-pyran-4-yl)-1,5,9,10-tetrahydro-1,2,4,5,8,9-hexaazabenzo[cd]cyclopenta[h]azulene | 325 |
| 74 | 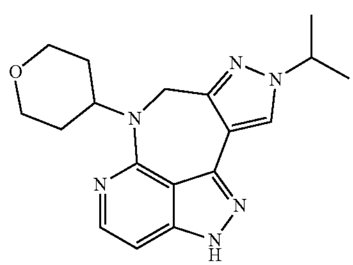 [SMILES: CC(C)n1cc2c(n1)CN(C1CCOCC1)c1nccc3[nH]nc-2c13] | 2-isopropyl-9-(tetrahydro-2H-pyran-4-yl)-2,5,9,10-tetrahydro-1,2,4,5,8,9-hexaazabenzo[cd]cyclopenta[h]azulene | 339 |
| 75 | 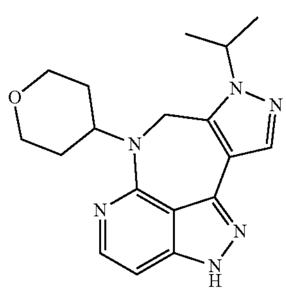 [SMILES: CC(C)n1ncc2c1CN(C1CCOCC1)c1nccc3[nH]nc-2c13] | 1-isopropyl-9-(tetrahydro-2H-pyran-4-yl)-1,5,9,10-tetrahydro-1,2,4,5,8,9-hexaazabenzo[cd]cyclopenta[h]azulene | 339 |
| 76 | 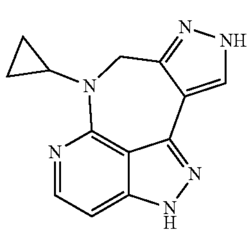 [SMILES: c1cc2[nH]nc3c2c(n1)N(C1CC1)Cc1n[nH]cc1-3] | 8-cyclopropyl-2,5,9,10-tetrahydro-1,2,4,5,8,9-hexaazabenzo[cd]cyclopenta[h]azulene | 253 |

-continued

| Example | Structure | Name | m/z (ESI)+ [M + H] |
|---|---|---|---|
| 77 | 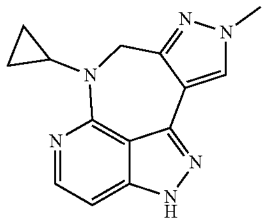 [SMILES: Cn1cc2c(n1)CN(C1CC1)c1nccc3[nH]nc-2c13] | 9-cyclopropyl-2-methyl-2,5,9,10-tetrahydro-1,2,4,5,8,9-hexaazabenzo[cd]cyclopenta[h]azulene | 267 |
| 78 | 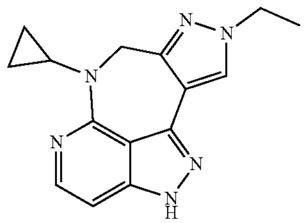 [SMILES: CCn1cc2c(n1)CN(C1CC1)c1nccc3[nH]nc-2c13] | 9-cyclopropyl-2-ethyl-2,5,9,10-tetrahydro-1,2,4,5,8,9-hexaazabenzo[cd]cyclopenta[h]azulene | 281 |
| 79 | 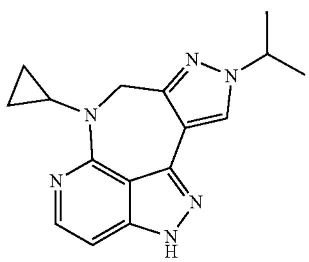 [SMILES: CC(C)n1cc2c(n1)CN(C1CC1)c1nccc3[nH]nc-2c13] | 9-cyclopropyl-2-isopropyl-2,5,9,10-tetrahydro-1,2,4,5,8,9-hexaazabenzo[cd]cyclopenta[h]azulene | 295 |
| 80 | 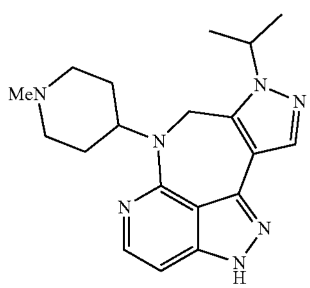 [SMILES: CC(C)n1ncc2c1CN(C1CCN(C)CC1)c1nccc3[nH]nc-2c13] | 1-isopropyl-9-(1-methylpiperidin-4-yl)-1,5,9,10-tetrahydro-1,2,4,5,8,9-hexaazabenzo[cd]cyclopenta[h]azulene | 352 |
| 81 | 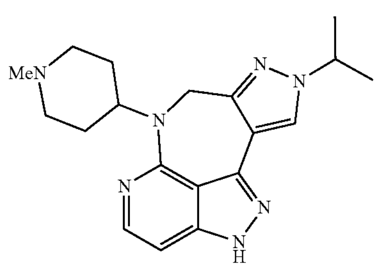 [SMILES: CC(C)n1cc2c(n1)CN(C1CCN(C)CC1)c1nccc3[nH]nc-2c13] | 2-isopropyl-9-(1-methylpiperidin-4-yl)-2,5,9,10-tetrahydro-1,2,4,5,8,9-hexaazabenzo[cd]cyclopenta[h]azulene | 352 |
| 82 | 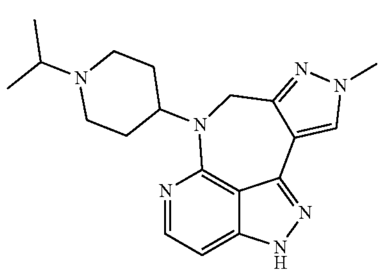 [SMILES: CC(C)N1CCC(N2Cc3nn(C)cc3-c3n[nH]c4ccnc2c34)CC1] | 9-(1-isopropylpiperidin-4-yl)-2-methyl-2,5,9,10-tetrahydro-1,2,4,5,8,9-hexaazabenzo[cd]cyclopenta[h]azulene | 352 |

-continued

| Example | Structure | Name | m/z (ESI)+ [M + H] |
|---|---|---|---|
| 83 | 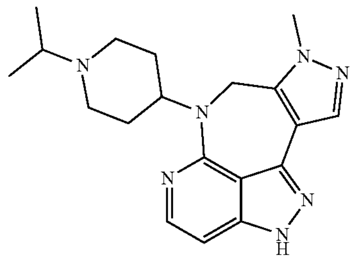 [SMILES: CC(C)N1CCC(N2Cc3c(cnn3C)-c3n[nH]c4ccnc2c34)CC1] | 9-(1-isopropylpiperidin-4-yl)-1-methyl-1,5,9,10-tetrahydro-1,2,4,5,8,9-hexaazabenzo[cd]cyclopenta[h]azulene | 352 |
| 84 | 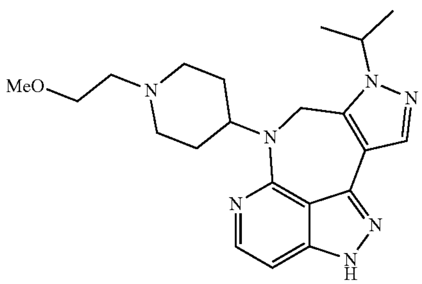 [SMILES: COCCN1CCC(N2Cc3c(cnn3C(C)C)-c3n[nH]c4ccnc2c34)CC1] | 1-isopropyl-9-(1-(2-methoxyethyl)piperidin-4-yl)-1,5,9,10-tetrahydro-1,2,4,5,8,9-hexaazabenzo[cd]cyclopenta[h]azulene | 396 |
| 85 | 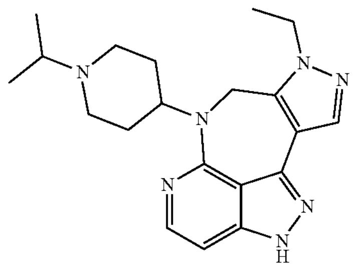 [SMILES: CCn1ncc2c1CN(C1CCN(C(C)C)CC1)c1nccc3[nH]nc-2c13] | 1-ethyl-9-(1-isopropylpiperidin-4-yl)-1,5,9,10-tetrahydro-1,2,4,5,8,9-hexaazabenzo[cd]cyclopenta[h]azulene | 366 |
| 86 | 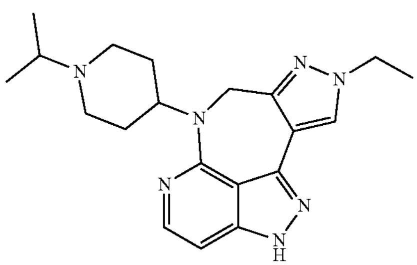 [SMILES: CCn1cc2c(n1)CN(C1CCN(C(C)C)CC1)c1nccc3[nH]nc-2c13] | 2-ethyl-9-(1-isopropylpiperidin-4-yl)-2,5,9,10-tetrahydro-1,2,4,5,8,9-hexaazabenzo[cd]cyclopenta[h]azulene | 366 |
| 87 | 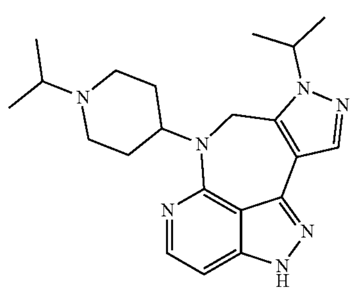 [SMILES: CC(C)N1CCC(N2Cc3c(cnn3C(C)C)-c3n[nH]c4ccnc2c34)CC1] | 1-isopropyl-9-(1-isopropylpiperidin-4-yl)-1,5,9,10-tetrahydro-1,2,4,5,8,9-hexaazabenzo[cd]cyclopenta[h]azulene | 380 |

-continued
| Example | Structure | Name | m/z (ESI)+ [M + H] |
|---|---|---|---|
| 88 | 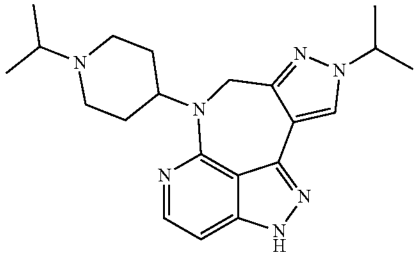 [SMILES: CC(C)N1CCC(N2Cc3nn(C(C)C)cc3-c3n[nH]c4ccnc2c34)CC1] | 2-isopropyl-9-(1-isopropylpiperidin-4-yl)-2,5,9,10-tetrahydro-1,2,4,5,8,9-hexaazabenzo[cd]cyclopenta[h]azulene | 380 |
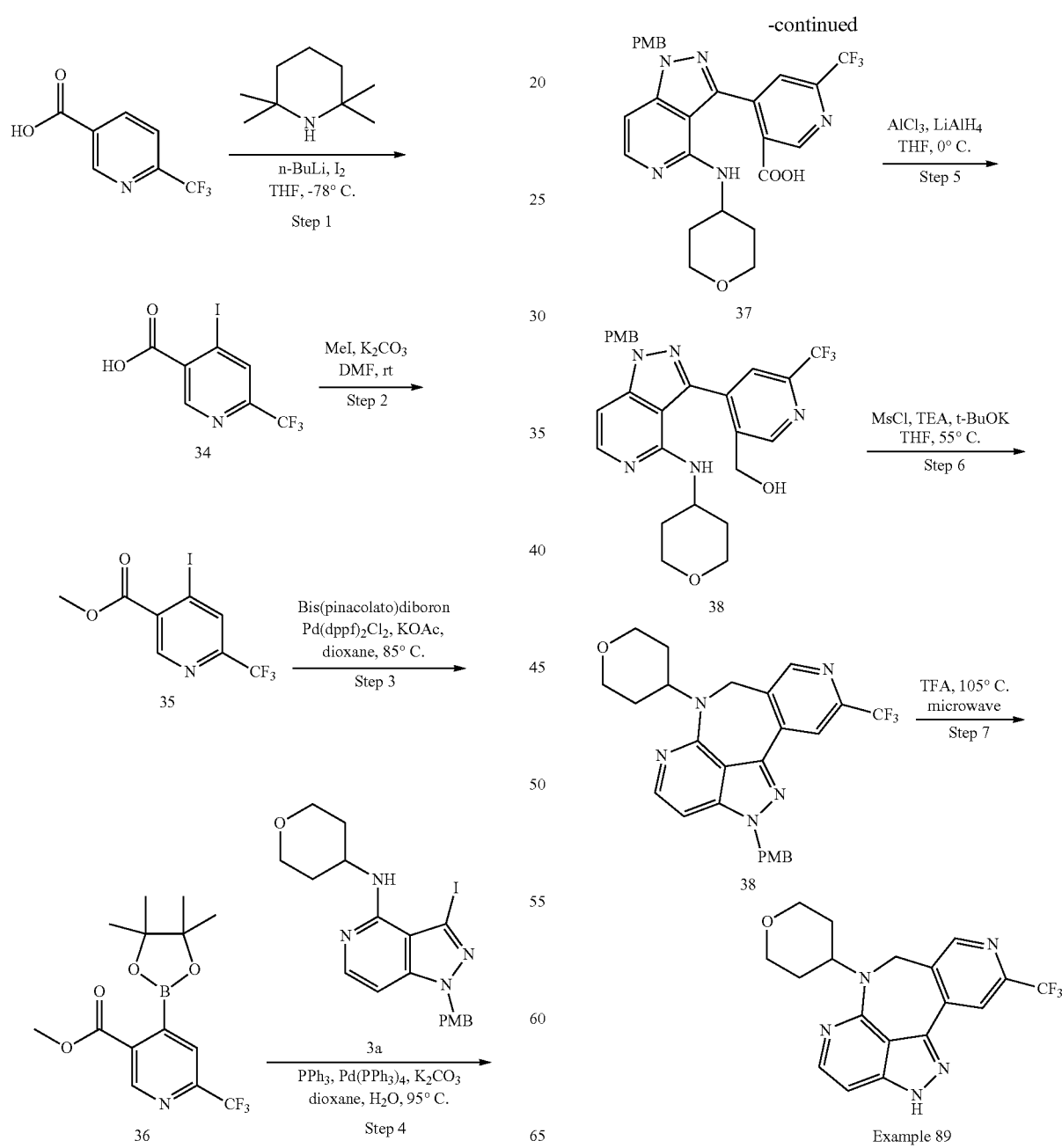

Step 1

Synthesis of 4-iodo-6-(trifluoromethyl)nicotinic Acid (34)

In a 3-neck 3000 mL round-bottom flask, 2,2,6,6-tetramethylpiperidine (34.5 g, 141 mmol) in dry THF (600 mL) under nitrogen atmosphere was stirred at −78° C. n-BuLi (98 mL, 2.4 M solution in hexane) was added to this solution and stirred for 0.5 h. To this solution, 6-(trifluoromethyl)nicotinic acid (15 g, 78 mmol) in dry THF (50 mL) was added dropwise and the mixture was stirred at −78° C. for 2.5 h. Then $I_2$ (29.3 g, 117 mmol) in dry THF (50 mL) was added slowly, and then the reaction solution was stirred for 1 h at −78° C. Then saturated $NH_4Cl$ (aq., 100 mL) was added to the above solution to quench the reaction. The pH value of the mixture was adjust to 4-5 with the addition of 1 N HCl and then the mixture was extracted with DCM (400 mL×3), dried over $Na_2SO_4$, filtrated and evaporated to give a residue, which was purified by chromatography on silica gel (PE/EA/AcOH, 1:10:0.01, v/v/v) to give compound 34 as a yellow solid (10 g, 40%). m/z (ESI)$^-$: 316 [M−H]$^-$.

Step 2

Synthesis of methyl 4-iodo-6-(trifluoromethyl)nicotinate (35)

A mixture of intermediate 34 (10 g, 31 mmol), $K_2CO_3$ (8.7 g, 63 mmol) and MeI (5.37 g, 37.9 mmol) in DMF (25 mL) was stirred at rt for overnight. Then $H_2O$ (300 mL) was added to the reaction mixture. The mixture was filtered and the cake was washed with water (20 mL) and dried in air to give compound 35 as a yellow solid (10 g, crude). m/z (ESI)$^+$: 332 [M+H]$^+$.

Step 3

Synthesis of methyl 4-(4,4,5,5-tetramethyl-1,3,2-dioxaborolan-2-yl)-6-(trifluoromethyl) nicotinate (36)

A mixture of intermediate 35 (10.0 g, 30.0 mmol), Bis(pinacolato)diboron (11.5 g, 45.3 mmol), KOAc (5.9 g, 60.4 mmol) and Pd(dppf)$_2$Cl$_2$ (3.31 g, 4.53 mmol) in dioxane (100 mL) was stirred at 95° C. under $N_2$ for 18 h. After concentration, the residue was partitioned between EtOAc (300 mL) and water (80 mL). The organic layer was washed with water (200 mL×2), dried with anhydrous $Na_2SO_4$, filtered and concentrated to dryness. The residue was purified with flash chromatography on silica gel (PE/EA, v/v, 20:1 to 10:1 gradient) to give the crude product as a yellow solid (2.2 g). m/z (ESI)$^+$: 250 [M+H]$^+$.

Step 4

Synthesis of 4-(1-(4-methoxybenzyl)-4-((tetrahydro-2H-pyran-4-yl)amino)-1H-pyrazolo[4,3-c]pyridin-3-yl)-6-(trifluoromethyl)nicotinic Acid (37)

A solution of compound 3a (1.23 g, 2.66 mmol), intermediate 36 (2.2 g, 6.6 mmol) and $K_2CO_3$ (733 mg, 5.32 mmol) in dioxane/$H_2O$ (4:1, v/v, 20 mL) was degassed with $N_2$. Afterwards, PPh$_3$ (175 mg, 0.67 mmol) and Pd(PPh$_3$)$_4$ (185 mg) were added to the above solution. The mixture was stirred at 100° C. for 18 h under nitrogen atmosphere. The reaction mixture was concentrated in vacuum to give a residue, which was purified by column chromatography on silica gel (DCM/MeOH, v/v, 5:1 to 2:1 gradient) to give compound 37 as a yellow solid (1.0 g, 69%). m/z (ESI)$^+$: 528 [M+H]$^+$.

Step 5

Synthesis of (4-(1-(4-methoxybenzyl)-4-((tetrahydro-2H-pyran-4-yl)amino)-1H-pyrazolo[4,3-c]pyridin-3-yl)-6-(trifluoromethyl)pyridin-3-yl)methanol (38)

A mixture of intermediate 37 (1 g, 1.9 mmol), AlCl$_3$ (234 mg, 1.9 mmol) and LiAlH$_4$ (261 mg, 7.86 mmol) in dry THF (40 mL) was stirred at 0° C. for 1 h. $H_2O$ (0.26 mL), 15% NaOH (aq., 0.26 mL) and $H_2O$ (0.8 mL) were added to the mixture subsequently. The mixture was filtered and the filtrate was concentrated in vacuum to give a residue, which was purified by column chromatography on silica gel (PE/EA, v/v, 5:1 to 2:1 gradient) to give the product as a yellow oil (240 mg, 24.6%). m/z (ESI)$^+$: 514 [M+H]$^+$.

Step 6

Synthesis of 11-(4-methoxybenzyl)-4-(tetrahydro-2H-pyran-4-yl)-8-(trifluoromethyl)-5,11-dihydro-4H-3,4,7,10,11-pentaazadibenzo[cd,h]azulene (39)

To a stirred solution of intermediate 38 (250 mg, 0.49 mmol) and TEA (198 mg, 1.95 mmol) in dry THF (20 mL) was added MsCl (112 mg, 0.97 mmol) dropwise at 0° C. After stirring at 0° C. for 0.5 h, t-BuOK (219 mg, 1.95 mmol) was added. Then the reaction mixture was stirred at 55° C. for 1.5 h and concentrated in vacuum to give a residue, which was purified by column chromatography on silica gel (PE/EA, 1:1, v/v) to give compound 39 as a yellow solid (230 mg, 95%). m/z (ESI)$^+$: 496 [M+H]$^+$.

Step 7

Synthesis of 4-(tetrahydro-2H-pyran-4-yl)-8-(trifluoromethyl)-5,11-dihydro-4H-3,4,7,10,11-pentaazadibenzo[cd,h]azulene (Example 89)

A solution of compound 39 (230 mg, 0.46 mmol) in TFA (3 mL) was stirred at 105° C. in a sealed tube under microwave for 1 h. The reaction mixture was concentrated in vacuum to give a residue, which was purified by prep-HPLC to give the final product as a white solid (55 mg, 33.1%). $^1$H-NMR (400 MHz, DMSO-d$_6$) δ ppm 1.76 (d, J=10.6 Hz, 2H), 2.18 (dt, J=11.5, 7.7 Hz, 2H), 3.47 (t, J=11.4 Hz, 2H), 4.04 (dd, J=11.1, 3.6 Hz, 2H), 4.41 (t, J=10.2 Hz, 1H), 4.89 (s, 2H), 7.24 (d, J=6.8 Hz, 1H), 7.86 (d, J=6.9 Hz, 1H), 8.27 (s, 1H), 9.19 (s, 1H), 14.70 (s, 1H); $^{19}$F-NMR (376 MHz, DMSO-d$_6$) δ ppm −66.72, −74.41; m/z (ESI)$^+$: 376 [M+H]$^+$.

Examples 90-92

Examples 90-92 were prepared similarly to Example 89 using appropriate pyridines in Step 1.

| Example | Structure | Name | m/z (ESI)+ [M + H] |
|---|---|---|---|
| 90 | 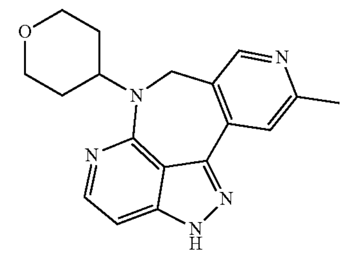 [SMILES: Cc1cc2c(cn1)CN(C1CCOCC1)c1nccc3[nH]nc-2c13] | 8-methyl-4-(tetrahydro-2H-pyran-4-yl)-5,11-dihydro-4H-3,4,7,10,11-pentaazadibenzo[cd,h]azulene | 322 |
| 91 | 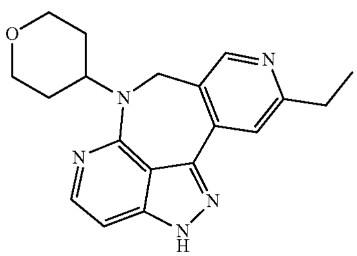 [SMILES: CCc1cc2c(cn1)CN(C1CCOCC1)c1nccc3[nH]nc-2c13] | 8-ethyl-4-(tetrahydro-2H-pyran-4-yl)-5,11-dihydro-4H-3,4,7,10,11-pentaazadibenzo[cd,h]azulene | 336 |
| 92 | 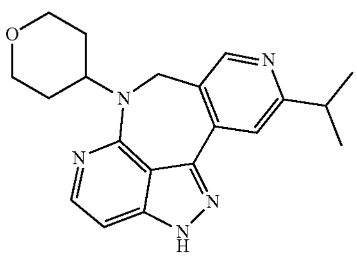 [SMILES: CC(C)c1cc2c(cn1)CN(C1CCOCC1)c1nccc3[nH]nc-2c13] | 8-isopropyl-4-(tetrahydro-2H-pyran-4-yl)-5,11-dihydro-4H-3,4,7,10,11-pentaazadibenzo[cd,h]azulene | 350 |
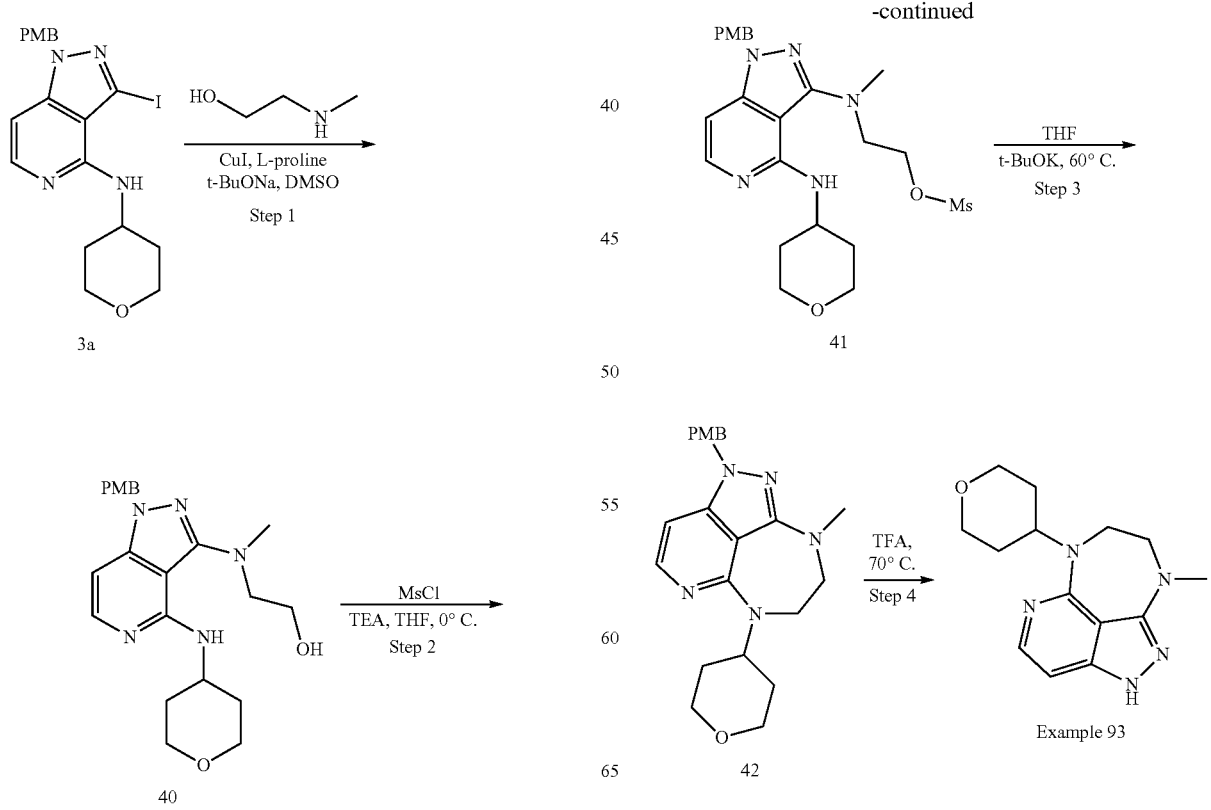

Step 1

Synthesis of 2-((1-(4-methoxybenzyl)-4-((tetrahydro-2H-pyran-4-yl)amino)-1H-pyrazolo[4,3-c]pyridin-3-yl)(methyl)amino)ethanol (40)

A mixture of 3-iodo-1-(4-methoxybenzyl)-N-(tetrahydro-2H-pyran-4-yl)-1H-pyrazolo[4,3-c]pyridin-4-amine (1.5 g, 3.23 mmol), 2-(methylamino)ethanol (1.98 g, 32.3 mmol), copper (I) iodide (123 mg, 0.65 mmol), L-proline (150 mg, 1.3 mmol) and t-BuOK (621 mg, 6.46 mmol) in DMSO (15 mL) was stirred at 100° C. overnight. Then the mixture was diluted with EtOAc (100 mL), washed with water (30 mL×2), brine (30 mL×1) and dried over $Na_2SO_4$. The mixture was filtered and the filtrate was concentrated. The residue was purified with silica gel chromatography, eluting with PE/EtOAc=2/1 (v/v) to give the 2-((1-(4-methoxybenzyl)-4-((tetrahydro-2H-pyran-4-yl)amino)-1H-pyrazolo[4,3-c]pyridin-3-yl)(methyl)amino)ethanol (760 mg, 57%) as colorless oil. m/z $(ESI)^+$: 412 $[M+H]^+$.

Step 2

Synthesis of 2-((1-(4-methoxybenzyl)-4-((tetrahydro-2H-pyran-4-yl)amino)-1H-pyrazolo[4,3-c]pyridin-3-yl)(methyl)amino)ethyl methanesulfonate (41)

To a solution of 2-((1-(4-methoxybenzyl)-4-((tetrahydro-2H-pyran-4-yl)amino)-1H-pyrazolo[4,3-c]pyridin-3-yl)(methyl)amino)ethanol (760 mg, 1.85 mmol) and $Et_3N$ (560 mg, 5.55 mmol) in THF (76 mL) was added methanesulfonyl chloride (429 mg, 3.7 mmol) dropwise at 0° C. under $N_2$, then the mixture was stirred at rt for 0.5 h. The reaction was quenched with water (10 mL) and extracted with EtOAc (20 mL×2). The combined organic phase was washed with brine (20 mL×1) and dried over $Na_2SO_4$. The organic phase was filtered and the filtrate was concentrated. The residue was purified by silica gel chromatography eluting with PE/EtOAc=3:1 (v/v) to give the 2-((1-(4-methoxybenzyl)-4-((tetrahydro-2H-pyran-4-yl)amino)-1H-pyrazolo[4,3-c]pyridin-3-yl) (methyl)amino)ethyl methanesulfonate (489 mg, 54%) as an colorless oil. m/z $(ESI)^+$: 490 $[M+H]^+$.

Step 3

Synthesis of 2-(4-methoxybenzyl)-9-methyl-6-(tetrahydro-2H-pyran-4-yl)-6,7,8,9-tetrahydro-2H-1,2,5,6,9-pentaazabenzo[cd]azulene (42)

To a solution of 2-((1-(4-methoxybenzyl)-4-((tetrahydro-2H-pyran-4-yl)amino)-1H-pyrazolo[4,3-c]pyridin-3-yl)(methyl)amino)ethyl methanesulfonate (455 mg, 0.93 mmol) in dry THF (50 mL) was added t-BuOK (312 mg, 2.79 mmol). The reaction was heated to 60° C. under $N_2$ for 1 h. Then the reaction was quenched with water (10 mL) and extracted with EtOAc (100 mL), the organic phase was washed with brine (30 mL), and dried over $Na_2SO_4$. The organic phase was filtered and the filtrate was concentrated under reduced pressure. The residue was purified by silica gel chromatography eluting with PE/EtOAc=1/1 (v/v) to give 2-(4-methoxybenzyl)-9-methyl-6-(tetrahydro-2H-pyran-4-yl)-6,7,8,9-tetrahydro-2H-1,2,5,6,9-pentaazabenzo[cd]azulene (167 mg, 46%) as an oil. $^1$H-NMR (400 MHz, $CDCl_3$) ppm 1.57-1.66 (m, 2H), 1.79 (m, 2H), 3.06 (s, 3H), 3.37 (m, 2H), 3.60 (m, 4H), 3.77 (s, 3H), 4.04 (m, 2H), 5.24 (m, 3H), 6.37 (d, J=6.0 Hz, 1H), 6.82 (d, J=8.0 Hz, 2H), 7.16 (d, J=8.0 Hz, 2H), 7.78 (d, J=6.0 Hz, 1H); m/z $(ESI)^+$: 394 $[M+H]^+$.

Step 4

Synthesis of 9-methyl-6-(tetrahydro-2H-pyran-4-yl)-6,7,8,9-tetrahydro-2H-1,2,5,6,9-pentaazabenzo[cd]azulene (Example 93)

A solution of 2-(4-methoxybenzyl)-9-methyl-6-(tetrahydro-2H-pyran-4-yl)-6,7,8,9-tetrahydro-2H-1,2,5,6,9-pentaazabenzo[cd]azulene (150 mg, 0.38 mmol) in TFA (7.5 mL) was heated to 70° C. under $N_2$ for 8 hours. Then the reaction was cooled and TFA was removed under reduced pressure. The residue was dissolved in EtOAc (150 mL), washed with $NaHCO_3$ (20 mL×2), brine (20 mL×1), and dried over $Na_2SO_4$. The organic phase was filtered and the filtrate was concentrated. The residue was purified by Prep-TLC (DCM/MeOH=11/1, v/v) to give the 9-methyl-6-(tetrahydro-2H-pyran-4-yl)-6,7,8,9-tetrahydro-2H-1,2,5,6,9-pentaazabenzo[cd]azulene (75 mg, 72%) as a white solid. $^1$H-NMR (400 MHz, DMSO-$d_6$) ppm 1.71 (m, 2H), 1.87 (m, 2H), 3.02 (s, 3H), 3.44 (m, 4H), 3.78 (m, 2H), 3.98 (m, 2H), 4.33 (m, 1H), 6.84 (s, 1H), 7.55 (s, 1H), 12.35 (br s, 1H), 12.98 (br s, 1H); $^{19}$F-NMR (376 MHz, DMSO-$d_6$) ppm −74.41; m/z $(ESI)^+$: 274 $[M+H]^+$.

Example 94

Example 94 was prepared similarly to Example 93 using 2-(ethylamino)ethanol in place of 2-(methylamino)ethanol in Step 1.

| Example | Structure | Name | m/z $(ESI)^+$ [M + H] |
|---|---|---|---|
| 94 | 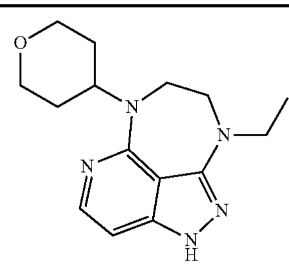 | 9-ethyl-6-(tetrahydro-2H-pyran-4-yl)-6,7,8,9-tetrahydro-2H-1,2,5,6,9-pentaazabenzo[cd]azulene | 288 |

Examples were assayed for inhibition of LRRK2 and selectivity over other kinases such as JAK2 using the following methods.

Materials and Methods

Materials

In Adapta™ Kinase Assay (LRRK2_$IC_{50}$ assay): the Kinase Reaction Buffer contained 5× Kinase Buffer S (Life Technologies, PV5213) and 2 mM DTT (Life Technologies, P2325). Kinase LRRK2 G2019S protein (PV4881) and ERM (LRRKtide, PV5093) were sourced from Life Technologies. The Adapta™ Universal Kinase Assay Kit (Life Technologies, PV5099) contained the following components: Adapta™ Eu-anti-ADP Antibody (PV5097; 4 μg); 10 μM Alexa Fluor® 647 ADP Tracer (PV5098; 200 pmol); TR-FRET Dilution Buffer (PV3574; 100 ml); Kinase Quench Buffer (P2825; 1 ml); 10 mM ATP (PV3227; 500 μl); and 10 mM ADP (PV5096; 500 μl). LRRK2-IN-1 (1234480-84-2, HY-10875) was sourced from MedChem Express.

In LANCE® Kinase Assay (JAK2_IC$_{50}$ selectivity assay): JAK2 (Invitrogen, Cat. No PV4288), ATP (Sigma, Cat. No. A7699-1G), DMSO (Sigma, Cat. No. D2650), DTT (Sigma, Cat. No. 43815), LANCE Ultra ULight™-JAK-1 peptide (Perkin Elmer, Cat. No. TRF0121), LANCE Eu-W1024 Anti-phosphotyrosine (PT66) (Perkin Elmer, Cat. No. AD0069), LANCE™ Detection Buffer (Perkin Elmer, Cat. No. CR97-100), Tofacitinib (PharmaBlock Sciences(Nanjing), Inc, Cat. No. PBN2011586-01); Equipments: Envision (Perkin Elmer), Bravo (Agilent); Consumables: 384 well Intermediate plate (Greiner, Cat. No. 781280), 384 well assay plate (Perkin Elmer, Cat. No. 6007299), In *Drosophila* model: anti-LRRK (phospho S935) Antibody [UDD2 10(12)] (ab133450) was sourced from Abcam. The ddc-GAL4 was sourced from Soochow University Medical Department.

Methods of Adapta™ Kinase Assay

The Adapta® universal kinase assay is a homogenous, fluorescent based immunoassay for the detection of ADP. In contrast to ATP depletion assays, the Adapta® assay is extremely sensitive to ADP formation such that a majority of the signal change occurs in the first 10-20% conversion of ATP to ADP. This makes the Adapta® universal kinase assay ideally suited for use with low activity kinases.

All assays were carried out at room temperature (~21° C.) and were linear with respect to time and enzyme concentration under the conditions used. Prepare a 1× solution of kinase reaction buffer from the 5× Kinase Buffer S stock (listed above) by adding 2 ml of 5× stock to 8 ml of H$_2$O to make 10 ml of 1× kinase reaction buffer. To this, add 20 µl of 1 M DTT.

Kinase reactions are performed in a 10 µl volume in low-volume 384-well plates. Typically, Greiner (Catalog #3674#, low-volume, white wall, 784075) plates are used. Other non—treated assay plates, while not tested, may also be suitable. The concentration of substrate in the assay is 100 µM, and the 1× kinase reaction buffer consists of 50 mM Tris-HCl pH8.5, 10 mM MgCl$_2$, 1 mM EGTA, 0.01% Brij-35, and 2 mM DTT, plus any additional additives that may be required for a specific kinase. Kinase reactions are allowed to proceed for 1 hour at room temperature before a 5 µl preparation of Kinase Quench Buffer (EDTA; 30 mM), Eu-labeled antibody (6 nM), and Tracer (18.9 nM) in TR-FRET dilution buffer is added. The final concentration of antibody in the assay well is 2 nM, 6.3 nM for the tracer, and 10 mM for EDTA. The plate is allowed to equilibrate at room temperature for at least 30 minutes before being read on a plate reader configured for Adapta™ TR-FRET.

The data presented in this document were generated using a BMG LABTECH PHERAstar plate reader using the appropriate filters and instrument settings for Adapta™. The Test Compounds are screened in 1% DMSO (final) in the well. For 8 point titrations, 5-fold serial dilutions are conducted from the starting concentration.

Methods of LANCE® Kinase Selectivity Assay

The assay involves two steps, the enzymatic step and the detection step with HTRF reagents. Step 1: During the enzymatic step the substrate-biotin is incubated with the kinase of interest. ATP is added to start the reaction. Step 2: The detection reagent catches the phosphorylated substrate and the resulting TR-FRET is proportional to the phosphorylation level.

Compound Preparation: Dissolve the test compounds into 30 mM DMSO solution and put them in nitrogen hood at room temperature for long term storage; Dilute the 30 mM compound in DMSO with 3-fold factor, total 11 concentrations; Aspirate 1 µl compound and then dilute them in 25 folds with kinase buffer. Mix well and balance 30 minutes at room temperature.

Kinase Reaction: Transfer 2.5 µl compounds in kinase buffer (4×) into assay plate by Agilent Bravo. Spin the plate; Transfer 5 µl enzyme mixture into the assay plate by using Eppendorf electronic multi-channel pipette. Spin the plate; Incubate the assay plate for 20 minutes at room temperature (23° C.); Add 2.5 µl kinase buffer with ATP into the assay plate by using Multidrop. Spin and seal the plate; Incubate the assay plate for 90 minutes at room temperature (23° C.).

Stop Reaction: Transfer 10 µl detection reagent (2 nM LANCE Eu-W1024 Anti-phosphotyrosine) into the assay plate by using Eppendorf electronic multi-channel pipette. Spin and seal the plate; Incubate the assay plate at room temperature (23° C.) for 60 minutes.

Detection and Read: The excitation wavelength is 340 nm, the primary emission wavelength is 615 nm and the secondary emission wavelength is 665 nm (for Cryptate and Ulight, respectively). Read the plate with EnVision to get the readout of both wavelengths; Calculate the ratio of 665 nm/615 nm.

IC$_{50}$ estimates were obtained using the software XLfit (IDBS Inc.).

Methods for Screening in *Drosophila* Model

*Drosophila* model was used to evaluate Examples in vivo. The GAL4/UAS system developed by Andrea Brand and Norbert Perrimon in 1993 [45] was used to generate transgenic *Drosophila* expressing LRRK2-G2019S in dopamine (DA) neurons. The system has two parts: the GAL4 gene, encoding the yeast transcription activator protein GAL4, and the UAS (Upstream Activation Sequence), an enhancer to which GAL4 specifically binds to activate gene transcription. This system takes advantage of the yeast GAL4 transcription factor, which binds specifically to the UAS.

To express LRRK2-G2019S in DA neurons, the UAS-Wild Type-LRRK2 and UAS-G2019S-LRRK2 transgenes were combined with the dopa decarboxylase (ddc)-GAL4 driver [46]. The 10 µM GW5074 was used for the positive control. The negative control group was DMSO control (all compounds were dissolved in DMSO with 1:1000 dillution). The *Drosophila* were maintained at 25° C. on a 12 hour light-12 hour dark cycle. GW5074 was used as positive control [47].

Survival Rate

Twenty newly enclosed female *Drosophila* were collected and placed in a food vial. The *Drosophila* were moved to fresh food vials every other day at which time deaths were scored.

Based on *Drosophila*' survival curve, the 50% survival time parameter indicates the time at which half of the *Drosophila* remained alive and was used to compare the survival ratio between the different groups. The mean 50% survival times and the standard errors were calculated based on 4 separate experiments for each group. The data were analysed by GraphPad PRISM® 6.0 software.

Climbing Assay

The negative geotaxis assay was used to analyse the locomotors ability of the *Drosophila*. Twenty *Drosophila* from each vial and 4 vials for each group were performed the climbing assay weekly.

The tested *Drosophila* were transferred into a vertical plastic tube (15 cm tall, 1.5 cm in diameter). After 30 min of rest at room temperature, the *Drosophila* were gently tapped to the bottom of the tube, the numbers of *Drosophila* that could climb to or above the test line within 10 seconds were counted and the percent were calculated.

The climbing abilities were analysed based on three separate experiments for each vial and the data were analysed by GraphPad PRISM® 6.0 software.

Kinase Assays at Week 6

The adult *Drosophila* heads were homogenized on ice, and the brain lysates were performed kinase reaction in kinase reaction buffer with ATP and DTT.

Then the lysates were electrophoresed through 12% SDS-PAGE gels and transferred to PVDF membranes (Millipore). The membranes were blocked in TBST with 5% skimmed milk for 1 hour at room temperature and then incubated in anti-LRRK2 pSer935 antibody (Abcam, ab133450) and anti-Flag antibody overnight at 4° C.

The proteins were detected with HRP-conjugated secondary antibodies and ECL detection reagents. The optical density of immunoblotting was analysed by Image J software and the ratio of phosphate LRRK2 protein compare to Flag protein were calculated and the data were analysed by GraphPad PRISM® 6.0 software.

Kinase Selectivity Assay Methods

1. MKK1 Assay

This is a two-step assay where inactive MAPK (0.06 mg/ml) is activated by MKK1 (diluted in 25 mM Tris, 0.1 mM EGTA, 0.1% b-mercaptoethanol, 0.01% Brij35, 1 mg/ml BSA) in 25.5 µl containing 25 mM Tris, 0.1 mM EGTA, 0.01% Brij35, 10 mM magnesium acetate and 0.005 mM ATP. After incubating at room temperature for 30 min, 5 µl from the first reaction is pipetted into 20 µl of the second reaction mix containing (final concentration) 25 mM Tris pH 7.5, 0.1 mM EGTA, 0.1 mM Na3VO4, 0.66 mg/ml myelin basic protein (MBP), 10 mM magnesium acetate and 0.05 mM [33P-g-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

2. MAPK2/ERK2 Assay.

MAPK/ERK2 (5-20 mU diluted in 50 mM Tris pH 7.5, 0.1 mM EGTA, 0.1 mM Na3VO4, 0.1% b-mercaptoethanol, 1 mg/ml BSA) is assayed against MBP in a final volume of 25.5 µl in 25 mM Tris pH 7.5, 0.1 mM EGTA, 0.33 mg/ml MBP, 10 mM magnesium acetate and 0.05 mM [33P-g-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

3. JNK1a1/SAPK1c Assay.

JNK1a1/SAPK1c (5-20 mU diluted in 50 mM Tris pH 7.5, 0.1 mM EGTA, 1 mg/ml BSA, 0.1% b-mercaptoethanol) is assayed against ATF2 (activating transcription factor in a final volume of 25.5 µl in 50 mM Tris pH 7.5, 0.1 mM EGTA, 0.1% b-Mercaptoethanol, ATF2 (3 µM), 10 mM magnesium acetate and 0.02 mM [33P-g-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

4. SAPK 2a/p38 Assay.

SAPK 2a/p38 (5-20 mU diluted in 50 mM Tris pH 7.5, 0.1 mM EGTA, 0.1 mM Na3VO4, 0.1% b-mercaptoethanol, 1 mg/ml BSA) is assayed against MBP in a final volume of 25.5 µl containing 25 mM Tris pH 7.5, 0.1 mM EGTA, 0.33 mg/ml MBP, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

5. SAPK 2b/p38ß2 Assay.

SAPK 2b/p38ß2 (5-20 mU diluted in 50 mM Tris pH 7.5, 0.1 mM EGTA, 0.1 mM Na3VO4, 0.1% b-mercaptoethanol, 1 mg/ml BSA) is assayed against MBP in a final volume of 25.51 µl containing 25 mM Tris pH 7.5, 0.1 mM EGTA, 0.33 mg/ml MBP, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

6. SAPK 3/p38g Assay.

SAPK 3/p38g (5-20 mU diluted in 50 mM Tris pH 7.5, 0.1 mM EGTA, 0.1 mM Na3VO4, 0.1% b-mercaptoethanol, 1 mg/ml BSA) is assayed against MBP in a final volume of 25.5 µl containing 25 mM Tris pH 7.5, 0.1 mM EGTA, 0.33 mg/ml MBP, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

7. SAPK4/p38∂ Assay.

SAPK 4/p38d (5-20 mU diluted in 50 mM Tris pH 7.5, 0.1 mM EGTA, 0.1 mM Na3VO4, 0.1% b-mercaptoethanol, 1 mg/ml BSA) is assayed against MBP in a final volume of 25.5 µl containing 25 mM Tris pH 7.5, 0.1 mM EGTA, 0.33 mg/ml MBP, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

8. MAPKAP-K1a Assay.

MAPKAP-K1a (5-20 mU diluted in 20 mM MOPS pH 7.5, 1 mM EDTA, 0.01% Brij35, 5% glycerol, 0.1% b-mercaptoethanol, 1 mg/ml BSA) is assayed against KKLNRTLSVA in a final volume of 25.5 µl containing 50 mM Na-b-glycerophosphate pH 7.5, 0.5 mM EDTA, 30 µM substrate peptide, 10 mM magnesium acetate and 0.05 mM [33P-g-ATP] (50-1000 cpm/pmole) and incubated for 40 min at room temperature. Assays are stopped by addition of 5 µl of 0.5 M (3%) orthophosphoric acid and then harvested onto P81 Unifilter plates with a wash buffer of 50 mM orthophosphoric acid.

9. MAPKAP-K2 Assay.

MAPKAP-K2 (5-20 mU diluted in 20 mM MOPS pH 7.5, 1 mM EDTA, 0.01% Brij35, 5% glycerol, 0.1% b-mercaptoethanol, 1 mg/ml BSA) is assayed against KKLNRTLSVA in a final volume of 25.51 containing 50 mM Na-b-glycerophosphate pH 7.5, 0.5 mM EDTA, 30 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

10. MSK1 Assay.

MSK1 (5-20 mU diluted in 20 mM MOPS pH 7.5, 1 mM EDTA, 0.01% Brij35, 0.1% b-mercaptoethanol, 1 mg/ml BSA) is assayed against a modified Crosstide peptide GRPRTSSFAEGKK in a final volume of 25.5 µl containing 8 mM MOPS pH7.0, 0.2 mM EDTA, 30 µM substrate peptide, 10 mM magnesium acetate and 0.02 mM [33P-g-

ATP](50-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

11. PRAK Assay.

PRAK (5-20 mU diluted in 50 mM Na-b-glycerophosphate pH 7.5, 0.1 mM EGTA, 0.1% b-mercaptoethanol, 1 mg/ml BSA) is assayed against KKLRRTLSVA in a final volume of 25.5 µl containing 50 mM Na-b-glycerophosphate pH 7.5, 0.1 mM EGTA, 30 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

12. PKA Assay.

PKA (5-20 mU diluted in 20 mM MOPS pH 7.5, 1 mM EDTA, 0.01% Brij35, 0.1% b-mercaptoethanol, 1 mg/ml BSA) is assayed against Kemptide (LRRASLG) in a final volume of 25.5 µl containing 8 mM MOPS pH 7.5, 0.2 mM EDTA, 30 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

13. PKCa Assay.

PKCa (5-20 mU diluted in 20 mM Hepes pH 7.4, 0.03% Triton X-100) is assayed against Histone H1 in the presence of PtdSerine and DAG (0.1 mg/ml. and 10 µg/ml) and 0.1 mM CaCl2. The assay is carried out in a final volume of 25.5 µl containing 20 mM Hepes pH 7.4, 0.03% Triton X-100, 0.1 mg/ml Histone H1, 10 mM magnesium acetate and 0.02 mM[33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

PtdSer/DAG preparation:—PtdSer stock=10 mg/ml in MeOH/Chloroform (1:2). Dry down required amount. Resuspend in appropriate volume of 10 mM Hepes pH 7.4. Vortex and briefly sonicate. (2×10-15 seconds at 10-15 seconds apart). DAG stock=10 mg/ml in MeOH/chloroform (1:2). Dry down required amount. Add sonicated PtdSer solution. Vortex and sonicate.

14. PDK1 Assay.

PDK1 (5-20 mU diluted in 50 mM Tris pH 7.5, 0.05% b-mercaptoethanol, 1 mg/ml BSA) is assayed against PDKtide (KTFCGTPEYLAPEVRREPRILSEEEQ-EMFRDFDYIADWC) in a final volume of 25.5 µl containing 50 mM Tris pH 7.5, 0.05% b-mercaptoethanol, 100 µM substrate peptide, 10 mM magnesium acetate and 0.02 mM [33P-g-ATP](50-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

15. ΔPH-PKBa-S473D Assay.

ΔPH-PKBa-S473D (5-20 mU diluted in 50 mM Tris pH 7.5, 0.1 mM EGTA, 0.1% b-mercaptoethanol, 1 mg/ml BSA) is assayed against a modified Crosstide peptide GRPRTSSFAEGKK in a final volume of 25.5 µl containing 50 mM Tris pH 7.5, 0.05% b-mercaptoethanol, 30 µM substrate peptide, 10 mM magnesium acetate and 0.005 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

16. SGK Assay.

SGK (5-20 mU diluted in 20 mM MOPS pH 7.5, 1 mM EDTA, 0.01% Brij35, 5% glycerol, 0.1% b-mercaptoethanol, 1 mg/ml BSA) is assayed against a modified Crosstide peptide GRPRTSSFAEGKK in a final volume of 25.5 µl containing 8 mM MOPS pH 7.0, 0.2 mM EDTA, 30 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

17. S6K1/P70 S6K Assay.

S6K1/P70 S6K (5-20 mU diluted in 20 mM MOPS pH 7.5, 1 mM EDTA, 0.01% Brij35, 5% glycerol, 0.1% b-mercaptoethanol, 1 mg/ml BSA) is assayed against substrate peptide (KKRNRTLTV) in a final volume of 25.5 µl containing 8 mM MOPS pH 7.0, 0.2 mM EDTA, 0.1 mM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

18. GSK3b Assay.

GSK3b (5-20 mU diluted in 20 mM MOPS pH 7.5, 1 mM EDTA, 0.01% Brij35, 5% glycerol, 0.1% b-mercaptoethanol, 1 mg/ml BSA) is assayed against Phospho-GS2 peptide (YRRAAVPPSPSLSRHSSPHQS(PO4)EDEEE) in a final volume of 25.5 µl containing 8 mM MOPS pH 7.0, 0.2 mM EDTA, 20 µM Phospho GS2 peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

19. ROCK-II (ROKa) Assay.

ROCK-II (ROKa) (5-20 mU diluted in 50 mM Tris pH 7.5, 0.1 mM EGTA, 0.1% b-mercaptoethanol, 1 mg/ml BSA) is assayed against Long S6 substrate peptide (KEAKEKRQEQIAKRRRLSSLRASTSKSGGSQK) in a final volume of 25.5 µl containing 50 mM Tris pH 7.5, 0.1 mM EGTA, 30 µM Long S6 substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

20. AMPK Assay.

AMPK (5-20 mU diluted in 50 mM Hepes pH 7.5, 1 mM DTT, 0.02% Brij35) is assayed against SAMS substrate peptide (HMRSAMSGLHLVKRR) in a final volume of 25.5 µl containing 50 mM Hepes pH 7.5, 1 mM DTT, 0.02% Brij35, 0.4 mM SAMS peptide, 0.196 mM AMP, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

21. CHK1 Assay.

CHK1 (5-20 mU diluted in 20 mM MOPS pH 7.5, 1 mM EDTA, 0.1% b-mercaptoethanol, 0.01% Brij-35, 5% glycerol, 1 mg/ml BSA) is assayed against CHKtide substrate peptide (KKKVSRSGLYRSPSMPENLNRPR) in a final volume of 25.5 µl containing 8 mM MOPS pH 7.0, 0.2 mM EDTA, 200 µM CHKtide, 10 mM magnesium acetate and 0.02 mM [33P-g-ATP](50-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

22. CK2 Assay.

CK2 (5-20 mU diluted in 20 mM Hepes pH7.5, 0.15 M NaCl, 0.1 mM EGTA, 0.1% Triton X-100, 5 mM DTT, 50% glycerol) is assayed against CKII peptide (RRRDDDSDDD) in a final volume of 25.5 µl containing 20 mM Hepes pH 7.5, 0.15 M NaCl, 0.1 mM EDTA, 5 mM DTT, 0.1% Triton-X 100, CKII peptide (0.165 mM), 10 mM magnesium acetate and 0.005 mM [33P-g-ATP](500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

23. PBK Assay.

PBK (5-20 mU diluted in 50 mM Na-b-glycerophosphate pH 7.0, 0.1% b-mercaptoethanol) is assayed against phosphorylase b peptide (KRKQISVRGL) in a final volume of 25.5 µl containing 50 mM Tris pH 8.6, 50 mM Na-b-glycerophosphate, 0.04 mM CaCl2, phosphorylase b peptide (0.196 mM), 10 mM magnesium acetate, 0.02 mM [33P-g-ATP] (500-1000 cpm/pmole) then incubated for 15 min at room temperature. Assays are stopped by addition of 5 µl of 0.5 M (3%) orthophosphoric acid and then harvested onto P81 Unifilter plates with a wash buffer of 50 mM orthophosphoric acid.

24. LCK Assay.

LCK (5-20 mU diluted in 20 mM MOPS pH 7.5, 1 mM EDTA, 0.01% Brij35, 5% glycerol, 0.1% b-mercaptoethanol, 1 mg/ml BSA) is assayed against Cdc2 peptide (KVEKIGEGTYGVVYK) in a final volume of 25.5 µl containing 50 mM Tris pH 7.5, 0.1 mM EGTA, 0.1 mM Na3Vo4, Cdc2 peptide (0.25 mM), 10 mM magnesium acetate and 0.05 mM [33P-g-ATP](500-1000 cpm/pmole) and incubated for 15 min at room temperature Assays are stopped by addition of 5 µl of 0.5 M (3%) orthophosphoric acid and then harvested onto P81 Unifilter plates with a wash buffer of 50 mM orthophosphoric acid.

25. CSK Assay.

CSK (5-20 mU diluted in 20 mM MOPS pH7.5, 1 mM EDTA, 0.01% Brij35, 5% glycerol, 0.1% b-mercaptoethanol, 1 mg/ml BSA) is assayed against Cdc2 peptide (KVEKIGEGTYGVVYK) in a final volume of 25.5 µl containing 8 mM MOPS pH7.0, 0.2 mM EDTA, Cdc2 peptide (0.25 mM), 10 mM magnesium acetate and 0.02 mM [33P-g-ATP](500-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

26. CDK2/Cyclin A Assay.

CDK2/cyclin A (5-20 mU diluted in 50 mM Hepes pH 7.5, 1 mM DTT, 0.02% Brij35, 100 mM NaCl) is assayed against Histone H1 in a final volume of 25.5 µl containing 50 mM Hepes pH7.5, 1 mM DTT, 0.02% Brij35, 100 mM NaCl, Histone H1 (1 mg/ml), 10 mM magnesium acetate and 0.02 mM [33P-g-ATP](500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

27. DYRK 1A Assay.

DYRK 1A (5-20 mU of diluted in 50 mM Tris pH7.5, 0.1 mM EGTA) is assayed against Woodtide (KKISGRL-SPIMTEQ) in a final volume of 25.5 µl containing 50 mM Tris pH 7.5, 0.1 mM EGTA, 350 µM substrate peptide, 10 mM Magnesium acetate and 0.05 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

28. CK1 Assay.

CK1 (5-20 mU diluted in 20 mM Hepes pH7.5, 0.15 M NaCl, 0.1 mM EGTA, 0.1% Triton X-100, 5 mM DTT, 50% glycerol) is assayed against CKI peptide (RRKDLHD-DEEDEAMSITA) in a final volume of 25.5 µl containing 20 mM Hepes pH 7.5, 0.15 M NaCl, 0.1 mM EDTA, 5 mM DTT, 0.1% Triton-X 100, CKI peptide (0.5 mM), 10 mM magnesium acetate and 0.02 mM [33P-g-ATP](500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

29. NEK6 Assay.

NEK6 (5-20 mU diluted in 50 mM Tris (pH 7.5), 0.1 mM EGTA, 1 mg/ml BSA, 0.1%, b-Mercaptoethanol) is assayed against NEK6 peptide (FLAKSFGSPNRAYKK) in a final volume of 25.5 µl containing 50 mM Tris (pH 7.5), 0.1 mM EGTA, 0.01% Brij, 0.1%, b-Mercaptoethanol, NEK6 peptide (0.3 mM), 10 mM magnesium acetate and 0.05 mM [33P-g-ATP](500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

30. NEK2a Assay.

5-20 mU of NEK2a (diluted in 50 mM Tris (pH 7.5), 0.1 mM EGTA, 1 mg/ml BSA, 0.1%, b-Mercaptoethanol) is assayed against NEK2a peptide (RFRRSRRMI) in a final volume of 25.5 µl containing 50 mM Tris (pH 7.5), 0.1 mM EGTA, 0.01% Brij, 0.1%, b-Mercaptoethanol, 300 µM NEK2a peptide, 10 mM magnesium acetate and 0.05 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

31. MAPKAP-K1b/RSK2 assay.

MAPKAP-K1b (5-20 mU diluted in 20 mM MOPS pH 7.5, 1 mM EDTA, 0.01% Brij35, 5% glycerol, 0.1% b-mercaptoethanol, 1 mg/ml BSA) is assayed against substrate peptide (KKLNRTLSVA) in a final volume of 25.51 containing 50 mM Na-b-glycerophosphate (pH 7.5), 0.5 mM EDTA, 30 µM substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

32. IKKb Assay.

5-20 mU of IKKb (diluted in 50 mM Tris (pH 7.5), 0.1 mM EGTA, 1 mg/ml BSA, 0.1%, b-Mercaptoethanol) is assayed against substrate peptide (LDDRHDSGLDSMKDEEY) in a final volume of 25.51 µl containing 50 mM Tris (pH 7.5), 0.1 mM EGTA, 0.1%, b-Mercaptoethanol, 300 µM substrate peptide, 10 mM magnesium acetate and 0.005 mM [33P-g-ATP](500-1000 cpm/ pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

33. smMLCK Assay 5-20 mU of smMLCK (diluted in 50 mM Hepes (pH 7.5), 0.1 mM EGTA, 1 mg/ml BSA, 0.1%, b-Mercaptoethanol) is assayed against substrate peptide (KKRPQRATSNVFA) in a final volume of 25.5 µl containing 50 mM Hepes (pH 7.5), 0.1 mM EGTA, 5 mM CaCl2, 10 M Calmodulin, 300 µM substrate peptide, 10 mM magnesium acetate and 0.05 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

34. PRK2 Assay 5-20 mU of PRK2 (diluted in 50 mM Tris (pH 7.5), 0.1 mM EGTA, 1 mg/ml BSA, 0.1%, b-Mercaptoethanol) is assayed against Long S6 peptide (KEAKEKRQEQIAKRRRLSSLRASTSKSGGSQK) in a final volume of 25.5 µl containing 50 mM Tris (pH 7.5), 0.1 mM EGTA, 0.1%, b-Mercaptoethanol, 30 µM Long S6 peptide, 10 mM magnesium acetate and 0.005 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

35. MNK2 Alpha Assay 5-20 mU of MNK2 (diluted in 50 mM Tris (pH 7.5), 0.1 mM EGTA, 1 mg/ml BSA, 0.1%, b-Mercaptoethanol) is assayed against substrate peptide (eIF4E) in a final volume of 25.5 µl containing 50 mM Tris (pH 7.5), 0.1 mM EGTA, 0.1%, b-Mercaptoethanol, 0.5 mg/ml substrate peptide, 10 mM magnesium acetate and 0.05 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

36. CAMK-1 Assay 5-20 mU of CAMK-1 (diluted in 50 mM Tris (pH 7.5), 0.1 mM EGTA, 1 mg/ml BSA, 0.1%, b-Mercaptoethanol) is assayed against substrate peptide (YLRRRLSDSNF) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.05 mM [33P-g-ATP](500-1000 cpm/pmole) and incubated for 30 mins at room temperature. Assays are stopped by addition of 5l1 of 0.5M (3%) orthophosphoric acid. Assays are harvested onto P81 Unifilter plates using a wash buffer of 50 mM orthophosphoric acid.

37. PIM2 Assay 5-20 mU of PIM2 (diluted in 50 mM Tris (pH 7.5), 0.1 mM EGTA, 1 mg/ml BSA, 0.1%, b-Mercaptoethanol) is assayed against substrate peptide (RSRHSSYPAGT) in a final volume of 25.5p1 containing 50 mM Tris (pH 7.5), 0.1 mM EGTA, 0.5 mM CaCl2, 0.3 µM calmodulin, 0.1%, b-Mercaptoethanol, 300 M substrate peptide, 10 mM magnesium acetate and 0.005 mM [33P-g-ATP](500-1000 cpm/pmole) and incubated for 30 mins at room temperature. Assays are stopped by addition of 5p1 of 0.5M (3%) orthophosphoric acid. Assays are harvested onto P81 Unifilter plates using a wash buffer of 50 mM orthophosphoric acid.

38. NEK7 Assay

NEK7 (5-20 mU diluted in 50 mM Tris (pH 7.5), 0.1 mM EGTA, 1 mg/ml BSA, 0.1%, b-Mercaptoethanol) is assayed against substrate peptide (FLAKSFGSPNRAYKK) in a final volume of 25.5 µl containing 50 mM Tris (pH 7.5), 0.1 mM EGTA, 0.01% Brij, 0.1%, b-Mercaptoethanol, substrate peptide (0.3 mM), 10 mM magnesium acetate and 0.02 mM [33P-g-ATP](500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

39. JNK3 Alpha 1 Assay

JNK3 alpha 1(5-20 mU diluted in 50 mM Tris (pH 7.5), 0.1 mM EGTA, 1 mg/ml BSA, 0.1% b-mercaptoethanol) is assayed against ATF2 (activating transcription factor in a final volume of 25.5 µl in 50 mM Tris pH 7.5, 0.1 mM EGTA, 0.1% b-Mercaptoethanol, ATF2 (3 µM), 10 mM magnesium acetate and 0.05 mM [33P-g-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

40. MAPKAP-K3 Assay 5-20 mU of MAPKAP-K3 (diluted in 50 mM Tris (pH 7.5), 0.1 mM EGTA, 1 mg/ml BSA, 0.1%, b-Mercaptoethanol) is assayed against substrate peptide (KKLNRTLSVA) in a final volume of 25.5 µl containing 50 mM Tris (pH 7.5), 0.1 mM EGTA, 0.1%, b-Mercaptoethanol, 30 µM substrate peptide, 10 mM magnesium acetate and 0.02 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

41. ERK8 Assay 5-20 mU of ERK8 (diluted in 50 mM Tris (pH 7.5), 0.1 mM EGTA, 1 mg/ml BSA, 0.1%, b-Mercaptoethanol) is assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

42. MNK1 Assay 5-20 mU of MNK1 (diluted in 50 mM Tris (pH 7.5), 0.1 mM EGTA, 1 mg/ml BSA, 0.1%, b-Mercaptoethanol) is assayed against substrate peptide (eIF4E) in a final volume of 25.5p1 containing 50 mM Tris (pH 7.5), 0.1 mM EGTA, 0.1%, b-Mercaptoethanol, 0.5 mg/ml substrate peptide, 10 mM magnesium acetate and 0.05 mM [33P-g-ATP](500-1000 cpm/pmole) and incubated for 30 mins at room temperature. Assays are stopped by addition of 5p1 of 0.5M (3%) orthophosphoric acid. Assays are harvested onto P81 Unifilter plates using a wash buffer of 50 mM orthophosphoric acid.

43. SRPK1 Assay 5-20 mU of SRPK1 (diluted in 50 mM Tris (pH 7.5), 0.1 mM EGTA, 1 mg/ml BSA, 0.1%, b-Mercaptoethanol) is assayed against substrate peptide (RSRSRSRSRSRSRSR) in a final volume of 25.5l µl containing 50 mM Tris (pH 7.5), 0.1 mM EGTA, 0.1%, b-Mercaptoethanol, 300 µM substrate peptide, 10 mM magnesium acetate and 0.05 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

44. ΔPH-PKBbeta (S474D) Assay

ΔPH-PKBbeta-S474D (5-20 mU diluted in 50 mM Tris pH 7.5, 0.1 mM EGTA, 0.1% b-mercaptoethanol, 1 mg/ml BSA) is assayed against a modified Crosstide peptide (GR-PRTSSFAEGKK) in a final volume of 25.5 µl containing 50 mM Tris pH 7.5, 0.05% b-mercaptoethanol, 30 µM substrate peptide, 10 mM magnesium acetate and 0.05 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

45. Aurora B Assay

Aurora B (5-20 mU diluted in 50 mM Tris pH 7.5, 0.1 mM EGTA, 0.1% b-mercaptoethanol, 1 mg/ml BSA) is assayed against a substrate peptide (LRRLSLGLRRLSLGLRRLSLGLRRLSLG) in a final volume of 25.5 µl containing 50 mM Tris pH 7.5, 0.05% b-mercaptoethanol, 300 µM substrate peptide, 10 mM magnesium acetate and 0.02 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

46. CHK2 Assay

CHK2 (5-20 mU diluted in 20 mM MOPS pH 7.5, 1 mM EDTA, 0.1% b-mercaptoethanol, 0.01% Brij-35, 5% glycerol, 1 mg/ml BSA) is assayed against CHKtide substrate peptide (KKKVSRSGLYRSPSMPENLNRPR) in a final volume of 25.5 µl containing 8 mM MOPS pH 7.0, 0.2 mM EDTA, 200 µM CHKtide, 10 mM magnesium acetate and 0.02 mM [33P-g-ATP](50-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

47. Src Assay

Src (5-20 mU diluted in 50 mM Tris pH 7.5, 0.1 mM EGTA, 0.1% b-mercaptoethanol, 1 mg/ml BSA) is assayed against a substrate peptide (KVEKIGEGTYGVVYK) in a final volume of 25.5 µl containing 50 mM Tris pH 7.5, 0.05% b-mercaptoethanol, 300 µM substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

48. EF2K Assay

EF2K (5-20 mU diluted in 50 mM Hepes pH 6.6, 0.1% b-mercaptoethanol, 1 mg/ml BSA) is assayed against a substrate peptide (RKKFGESKTKTKEFL) in a final volume of 25.5 µl containing 50 mM Hepes pH 6.6, 0.2 mM CaCl2, 0.3 µM Calmodulin, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

49. MARK3 Assay

MARK3 (5-20 mU diluted in 50 mM Tris pH 7.5, 0.1 mM EGTA, 0.1% b-mercaptoethanol, 1 mg/ml BSA) is assayed against CHKtide substrate (KKKVSRSGLYR-SPSMPENLNRPR) in a final volume of 25.5 µl containing 50 mM Tris pH 7.5, 0.05% b-mercaptoethanol, 300 µM substrate peptide, 10 mM magnesium acetate and 0.005 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

50. MST2 Assay

MST2 (5-20 mU diluted in 50 mM Tris pH 7.5, 0.1 mM EGTA, 0.1% b-mercaptoethanol, 100 M Vanadate) is assayed against MBP in a final volume of 25.5 µl containing 50 mM Tris pH 7.5, 0.05% b-mercaptoethanol, 0.33 mg/ml MBP, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

51. PKD1 Assay

PKD1 (5-20 mU diluted in 50 mM Tris pH 7.5, 0.1 mM EGTA, 0.1% b-mercaptoethanol, 1 mg/ml BSA) is assayed substrate peptide (KKLNRTLSVA) in a final volume of 25.5 µl containing 50 mM Tris pH 7.5, 0.05% b-mercaptoethanol, 30 µM substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

52. PLK1 Assay

PLK1 (5-20 mU diluted in 50 mM Tris pH 7.5, 0.1 mM EGTA, 0.1% b-mercaptoethanol, 1 mg/ml BSA, 100 µM Vanadate) is assayed against a substrate peptide (ISDELM-DATFADQEAKKK) in a final volume of 25.5 µl containing 50 mM Tris pH 7.5, 0.05% b-mercaptoethanol, 10 µM Vanadate, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

53. DYRK2 Assay

DYRK2 (5-20 mU of diluted in 50 mM Tris pH7.5, 0.1 mM EGTA) is assayed against Woodtide (KKISGRL-SPIMTEQ) in a final volume of 25.5 µl containing 50 mM Tris pH 7.5, 0.1 mM EGTA, 350 µM substrate peptide, 10 mM Magnesium acetate and 0.05 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

54. JNK2 Assay

JNK2 1(5-20 mU diluted in 50 mM Tris (pH 7.5), 0.1 mM EGTA, 1 mg/ml BSA, 0.1% b-mercaptoethanol) is assayed against ATF2 (activating transcription factor in a final volume of 25.5 µl in 50 mM Tris pH 7.5, 0.1 mM EGTA, 0.1% b-Mercaptoethanol, ATF2 (3 µM), 10 mM magnesium acetate and 0.02 mM [33P-g-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

55. DYRK3 Assay

DYRK3 (5-20 mU of diluted in 50 mM Tris pH7.5, 0.1 mM EGTA) is assayed against Woodtide (KKISGRL-SPIMTEQ) in a final volume of 25.5 µl containing 50 mM Tris pH 7.5, 0.1 mM EGTA, 350 µM substrate peptide, 10 mM Magnesium acetate and 0.005 mM [33P-g-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

56. HIPK2 Assay 5-20 mU of HIPK2 (diluted in 50 mM Tris (pH 7.5), 0. mM EGTA, 1 mg/ml BSA, 0.1%, b-Mercaptoethanol) is assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

57. HIPK3 Assay 5-20 mU of HIPK3 (diluted in 50 mM Tris (pH 7.5), 0. mM EGTA, 1 mg/ml BSA, 0.1%, b-Mercaptoethanol) is assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.02 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

58. PAK4 Assay

PAK4 (5-20 mU diluted in 50 mM Tris pH 7.5, 0.1 mM EGTA, 0.1% b-mercaptoethanol, 1 mg/ml BSA) is assayed against a substrate peptide (RRRLSFAEPG) in a final volume of 25.5 µl containing 50 mM Tris pH 7.5, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

59. PAK5 (PAK7) Assay

PAK5 (PAK7)(5-20 mU diluted in 50 mM Tris pH 7.5, 0.1 mM EGTA, 0.1% b-mercaptoethanol, 1 mg/ml BSA) is assayed against a substrate peptide (RRRLSFAEPG) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

60. PAK6 Assay

PAK6 (5-20 mU diluted in 50 mM Tris pH 7.5, 0.1 mM EGTA, 0.1% b-mercaptoethanol, 1 mg/ml BSA) is assayed against a substrate peptide (RRRLSFAEPG) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

61. CAMKKa Assay 5-20 mU of CAMKKa (diluted in 50 mM Tris (pH 7.5), 0.1 mM EGTA, 1 mg/ml BSA, 0.1%, b-Mercaptoethanol) is assayed against substrate peptide (AK-PKGNKDYHLQTCCGSLAYRRR) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.02 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

62. CAMKKb Assay 5-20 mU of CAMKKb (diluted in 50 mM Tris (pH 7.5), 0.1 mM EGTA, 1 mg/ml BSA, 0.1%, b-Mercaptoethanol) is assayed against substrate peptide (DGE-FLRTSCGSPNYAARRR) in a final volume of 25.5 µl containing 50 mM Tris (pH 7.5), 0.1 mM EGTA, 0.5 mM CaCl2, 0.3 µM calmodulin, 0.1%, b-Mercaptoethanol, 300 µM substrate peptide, 10 mM magnesium acetate and 0.02 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

63. PIM1 Assay

PIM1 (5-20 mU diluted in 50 mM Tris pH 7.5, 0.1 mM EGTA, 0.1% b-mercaptoethanol, 1 mg/ml BSA) is assayed against a substrate peptide (RSRHSSYPAGT) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

64. PIM3 Assay

PIM3 (5-20 mU diluted in 50 mM Tris pH 7.5, 0.1 mM EGTA, 0.1% b-mercaptoethanol, 1 mg/ml BSA) is assayed against a substrate peptide (RSRHSSYPAGT) in a final volume of 25.5 µl containing 50 mM Tris pH 7.5, 0.05% b-mercaptoethanol, 300 µM substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

65. PLK1 Assay

PLK1 (5-20 mU diluted in 50 mM Tris pH 7.5, 0.1 mM EGTA, 0.1% b-mercaptoethanol, 1 mg/ml BSA, 100 M Vanadate) is assayed against a substrate peptide (ISDELM-DATFADQEAKKK) in a final volume of 25.5 µl containing 50 mM Tris pH 7.5, 0.05% b-mercaptoethanol, 10 M Vanadate, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

66. BRSK2 Assay

BRSK2 (5-20 mU diluted in 50 mM Tris pH 7.5, 0.1 mM EGTA, 0.1% b-mercaptoethanol, 1 mg/ml BSA) is assayed against a substrate peptide (KKLNRTLSFAEPG) in a final volume of 25.5 µl containing 50 mM Tris pH 7.5, 0.05% b-mercaptoethanol, 300 µM substrate peptide, 10 mM magnesium acetate and 0.05 mM [33P-g-ATP] (50-1000 cpm/ pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

67. MELK Assay

MELK (5-20 mU diluted in 50 mM Tris pH 7.5, 0.1 mM EGTA, 0.1% b-mercaptoethanol, 1 mg/ml BSA) is assayed against a substrate peptide (KKLNRTLSFAEPG) in a final volume of 25.5 µl containing 50 mM Tris pH 7.5, 0.05% b-mercaptoethanol, 200 µM substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

68. PKC Zeta Assay

PKC zeta (5-20 mU diluted in 50 mM Tris pH 7.5, 0.1 mM EGTA, 0.1% b-mercaptoethanol, 1 mg/ml BSA, 100 µM Vanadate) is assayed against a substrate peptide (ERMRPRKRQGSVRRRV) in a final volume of 25.5 µl containing 50 mM Tris pH 7.5, 0.05% b-mercaptoethanol, 10 M Vanadate, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

69. Aurora C Assay

Aurora C (5-20 mU diluted in 50 mM Tris pH 7.5, 0.1 mM EGTA, 0.1% b-mercaptoethanol, 1 mg/ml BSA) is assayed against a substrate peptide (LRRLSLGLRRLSLGLRRLSLGLRRLSLG) in a final volume of 25.5 µl containing 50 mM Tris pH 7.5, 0.05% b-mercaptoethanol, 300 µM substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

70. ERK1 Assay 5-20 mU of ERK1 (diluted in 50 mM Tris (pH 7.5), 0.1 mM EGTA, 1 mg/ml BSA, 0.1%, b-Mercaptoethanol) is assayed against MBP in a final volume of 25.5 µl containing 50 mM Tris (pH 7.5), 0.1 mM EGTA, 0.1%, b-Mercaptoethanol, 0.33 mg/ml MBP, 10 mM magnesium acetate and 0.005 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

71. FGF-R1 Assay

FGF-R1 (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

72. IRR Assay 5-20 mU of IRR (diluted in 50 mM Hepes (pH 7.5), 0.1 mM EGTA) is assayed against MBP in a final volume of 25.5 µl containing 50 mM Hepes (pH 7.5), 0.1 mM EGTA, 0.33 mg/ml MBP, 10 mM magnesium acetate and 0.005 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

73. EPH-A2 Assay

EPH-A2 (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 0.1 mg/ml substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

74. MST4 Assay 5-20 mU of MST4 (diluted in 50 mM Tris (pH 7.5), 0.1 mM EGTA) is assayed against MBP in a final volume of 25.51 containing 50 mM Tris (pH 7.5), 0.1 mM EGTA, 0.33 mg/ml MBP, 10 mM magnesium acetate and 0.02 mM [33P-g-ATP](500-1000 cpm/pmole) and incubated for 30 mins at room temperature. Assays are stopped by addition of 51 of 0.5M (3%) orthophosphoric acid. Assays are harvested onto P81 Unifilter plates using a wash buffer of 50 mM orthophosphoric acid.

75. SYK Assay

SYK (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

76. YES1 Assay

YES1 (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

77. IGF-1R Assay

IGF-1R (5-20 mU diluted in 50 mM Tris pH 7.5, 0.1 mM EGTA, 1 mg/ml BSA) is assayed against a substrate peptide (KKKSPGEYVNIEFG) in a final volume of 25.5 µl containing 50 mM Tris pH 7.5, 300 M substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

78. VEG-FR Assay

VEG-FR (5-20 mU diluted in 50 mM Tris pH 7.5, 0.1 mM EGTA, 1 mg/ml BSA) is assayed against a substrate peptide (KKKSPGEYVNIEFG) in a final volume of 25.5 µl containing 50 mM Tris pH 7.5, 300 M substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

79. BTK Assay

BTK (5-20 mU diluted in 50 mM Tris pH 7.5, 0.1 mM EGTA, 1 mg/ml BSA) is assayed against a substrate peptide (KVEKIGEGTYGVVYK) in a final volume of 25.5 µl containing 50 mM Tris pH 7.5, 300 M substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

80. IR-HIS Assay

IR-HIS (5-20 mU diluted in 50 mM Tris pH 7.5, 0.1 mM EGTA, 1 mg/ml BSA) is assayed against a substrate peptide (KKSRGDYMTMQIG) in a final volume of 25.5 µl containing 50 mM Tris pH 7.5, 300 M substrate peptide, 10 mM magnesium acetate and 0.02 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

81. EPH-B3 Assay

EPH-B3 (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 1 mg/ml substrate peptide, 10 mM magnesium acetate and 0.005 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

82. TBK1 (DU12569) Assay

TBK1 (DU12569) (5-20 mU diluted in 50 mM Tris pH 7.5, 0.1 mM EGTA, 1 mg/ml BSA) is assayed against a substrate peptide (KKKKERLLDDRHDSGLDSMKDEE) in a final volume of 25.5 µl containing 50 mM Tris pH 7.5, 300 µM substrate peptide, 10 mM magnesium acetate and 0.05 mM [33P-g-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

83. IKKepsilon (DU14231) Assay 5-20 mU of IKKepsilon (DU14231)(diluted in 50 mM Tris (pH 7.5), 0.1 mM EGTA, 1 mg/ml BSA) is assayed against MBP in a final volume of 25.5 µl containing 50 mM Tris (pH 7.5), 0.1 mM EGTA, 0.33 mg/ml MBP, 10 mM magnesium acetate and 0.05 mM [33P-g-ATP](500-1000 cpm/pmole) and incubated for 30 mins at room temperature. Assays are stopped by addition of 5 µl of 0.5M (3%) orthophosphoric acid. Assays are harvested onto P81 Unifilter plates using a wash buffer of 50 mM orthophosphoric acid.

84. GCK Assay

GCK (5-20 mU diluted in 50 mM Tris pH 7.5, 0.1 mM EGTA, 0.1% β-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

85. IRAK4 Assay

IRAK4 (5-20 mU diluted in 50 mM Tris pH 7.5, 0.1 mM EGTA, 0.1% 0-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

86. NUAK1 assay

NUAK1 (5-20 mU diluted in 50 mM Tris pH 7.5, 0.1 mM EGTA, 0.1% 0-mercaptoethanol, 1 mg/ml BSA) is assayed against ALNRTSSDSALHRRR in a final volume of 25.5 µl containing 50 mM Tris pH 7.5, 0.1 mM EGTA, 0.3 mM ALNRTSSDSALHRRR, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

87. MLK1 Assay

MLK1 (5-20 mU diluted in 50 mM Tris pH 7.5, 0.1 mM EGTA, 0.1% 0-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

88. MINK1 Assay

MINK1 (5-20 mU diluted in 50 mM Tris pH 7.5, 0.1 mM EGTA, 0.1% β-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.05 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

89. MLK3 Assay

MLK3 (5-20 mU diluted in 50 mM Tris pH 7.5, 0.1 mM EGTA, 0.1% 0-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

90. LKB1 Assay

LKB1 (5-20 mU diluted in 50 mM Tris pH 7.5, 0.1 mM EGTA, 0.1% β-mercaptoethanol, 1 mg/ml BSA) is assayed against LSNLYHQGKFLQTFCGSPLYRRR in a final volume of 25.5 µl containing 50 mM Tris pH 7.5, 0.1 mM EGTA, 0.2 mM LSNLYHQGKFLQTFCGSPLYRRR, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

91. HER4 Assay

HER4 (5-20 mU diluted in 50 mM Tris pH 7.5, 0.1 mM EGTA, 0.1% β-mercaptoethanol, 1 mg/ml BSA) is assayed against Poly Glut Tyr in a final volume of 25.51 µl containing 50 mM Tris pH 7.5, 0.1 mM EGTA, 1 mg/ml Poly Glut Tyr, 10 mM magnesium acetate and 0.005 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

92. TTK Assay

TTK (5-20 mU diluted in 50 mM Tris pH 7.5, 0.1 mM EGTA, 0.1% 0-mercaptoethanol, 1 mg/ml BSA) is assayed against RSRSRSRSRSRSRSR in a final volume of 25.51 µl containing 50 mM Tris pH 7.5, 0.1 mM EGTA, 0.3 mM RSRSRSRSRSRSRSR, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

93. RIPK2 Assay

RIPK2 (5-20 mU diluted in 50 mM Tris pH 7.5, 0.1 mM EGTA, 0.1% β-mercaptoethanol, 1 mg/ml BSA) is assayed against MBP in a final volume of 25.51 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

94. Aurora A Assay

Aurora A (5-20 mU diluted in 50 mM Tris pH 7.5, 0.1 mM EGTA, 0.1% β-mercaptoethanol, 1 mg/ml BSA) is assayed against LRRLSLGLRRLSLGLRRLSLGLRRLSLG in a final volume of 25.51 µl containing 50 mM Tris pH 7.5, 0.1 mM EGTA, 0.3 mM LRRLSLGLRRLSLGLRRLSLGLRRLSLQ 10 mM magnesium acetate and 0.005 mM [33P-γ-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

95. PAK2 Assay

PAK2 (5-20 mU diluted in 50 mM Tris pH 7.5, 0.1 mM EGTA, 0.1% β-mercaptoethanol, 1 mg/ml BSA) is assayed against RRRLSFAEPG in a final volume of 25.5 µl containing 50 mM Tris pH 7.5, 0.1 mM EGTA, 0.3 mM RRRLSFAEPG 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

96. BRSK1 Assay

BRSK1 (5-20 mU diluted in 50 mM Tris pH 7.5, 0.1 mM EGTA, 0.1% β-mercaptoethanol, 1 mg/ml BSA) is assayed against KKLNRTLSFAEPG in a final volume of 25.5 µl containing 50 mM Tris pH 7.5, 0.1 mM EGTA, 0.3 mM KKLNRTLSFAEPG, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

97. HIPK3 Assay

HIPK3 (5-20 mU diluted in 50 mM Tris pH 7.5, 0.1 mM EGTA, 0.1% β-mercaptoethanol, 1 mg/ml BSA) is assayed against MBP in a final volume of 25.51 containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

98. HIPK1 Assay

HIPK1 (5-20 mU diluted in 50 mM Tris pH 7.5, 0.1 mM EGTA, 0.1% 0-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

99. JNK3a1 Assay

JNK3 (5-20 mU diluted in 50 mM Tris pH 7.5, 0.1 mM EGTA, 1 mg/ml BSA, 0.1% β-mercaptoethanol) is assayed against ATF2 (activating transcription factor in a final volume of 25.5 µl in 50 mM Tris pH 7.5, 0.1 mM EGTA, 0.1% β-Mercaptoethanol, ATF2 (3 µM), 10 mM magnesium acetate and 0.02 mM [33P-γ-ATP] (500-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

100. MAPKAP-K3 Assay

MAPKAP-K3 (5-20 mU diluted in 20 mM MOPS pH 7.5, 1 mM EDTA, 0.01% Brij35, 5% glycerol, 0.1% β-mercaptoethanol, 1 mg/ml BSA) is assayed against KKLNRTLSVA in a final volume of 25.51 containing 50 mM Na-β-glycerophosphate pH 7.5, 0.5 mM EDTA, 30 µM substrate peptide, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

101. MARK2 Assay

MARK2 (5-20 mU diluted in 50 mM Tris pH 7.5, 0.1 mM EGTA, 0.1% 0-mercaptoethanol, 1 mg/ml BSA) is assayed against KKKVSRSGLYRSPSMPENLNRPR in a final volume of 25.5 µl containing 50 mM Tris pH 7.5, 0.1 mM EGTA, 0.3 mM KKKVSRSGLYRSPSMPENLNRPR, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

102. MARK4 Assay

MARK4 (5-20 mU diluted in 50 mM Tris pH 7.5, 0.1 mM EGTA, 0.1% 0-mercaptoethanol, 1 mg/ml BSA) is assayed against KKKVSRSGLYRSPSMPENLNRPR in a final volume of 25.5 µl containing 50 mM Tris pH 7.5, 0.1 mM EGTA, 0.3 mM KKKVSRSGLYRSPSMPENLNRPR, 10 mM magnesium acetate and 0.05 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

103. EPH-B4 Assay

EPH-B4 (5-20 mU diluted in 50 mM Tris pH 7.5, 0.1 mM EGTA, 10 mM MnCl, 1 mg/ml BSA) is assayed against a substrate peptide (Poly Glut Tyr) in a final volume of 25.5 µl containing 50 mM Tris pH 7.5, 0.1 mM EGTA, 10 mM MnCl, 1 mg/ml substrate peptide, 10 mM magnesium acetate and 0.05 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

104. JAK2 Assay

JAK2 (5-20 mU diluted in 50 mM Tris pH 7.5, 0.1 mM EGTA, 0.05% 0-mercaptoethanol, 1 mg/ml BSA) is assayed against PDKtide (KTFCGTPEYLAPEVRREPRILSEEEQ-EMFRDFDYIADWC) in a final volume of 25.5 µl containing 50 mM Tris pH 7.5, 0.1 mM EGTA, 0.05% 0-mercaptoethanol, 100 µM substrate peptide, 10 mM magnesium acetate and 0.005 mM [33P-γ-ATP] (50-1000 cpm/pmole) and incubated for 30 min at room temperature Assays are stopped by addition of 5 µl of 0.5 M (3%) orthophosphoric acid and then harvested onto P81 Unifilter plates with a wash buffer of 50 mM orthophosphoric acid.

105. EPH-A4 Assay

EPH-A4 (5-20 mU diluted in 50 mM Tris pH 7.5, 0.1 mM EGTA, 10 mM MnCl, 1 mg/ml BSA) is assayed against a substrate peptide (Poly Glut Tyr) in a final volume of 25.5 µl containing 50 mM Tris pH 7.5, 0.1 mM EGTA, 1 mg/ml substrate peptide, 10 mM magnesium acetate and 0.05 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

106. TAK1 Assay

TAK1 (5-20 mU diluted in 50 mM Tris pH 7.5, 0.1 mM EGTA, 1 mg/ml BSA) is assayed against a substrate peptide (RLGRDKYKTLRQIRQ) in a final volume of 25.5 µl containing 50 mM Tris pH 7.5, 0.1 mM EGTA, 0.1% β-Mercaptoethanol, 300 µM substrate peptide, 10 mM magnesium acetate, 0.5 mM MnCl and 0.005 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

107. TrkA Assay

TrkA (5-20 mU diluted in 50 mM Tris pH 7.5, 0.1 mM EGTA, 10 mM MnCl, 1 mg/ml BSA) is assayed against a substrate peptide (Poly Glut Tyr) in a final volume of 25.5 µl containing 50 mM Tris pH 7.5, 0.1 mM EGTA, 1 mg/ml substrate peptide, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

108. MEKK1 Assay

MEKK1 (5-20 mU diluted in 50 mM Tris pH 7.5, 0.1 mM EGTA, 0.1% 0-mercaptoethanol, 1 mg/ml BSA) is assayed against MBP in a final volume of 25.5 µl containing 50 mM Tris pH 7.5, 0.1 mM EGTA, 0.33 mg/ml MBP, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

109. MARK1 Assay

MARK1 (5-20 mU diluted in 50 mM Tris pH 7.5, 0.1 mM EGTA, 0.1% 0-mercaptoethanol, 1 mg/ml BSA) is assayed against KKKVSRSGLYRSPSMPENLNRPR in a final volume of 25.5 µl containing 50 mM Tris pH 7.5, 0.1 mM EGTA, 0.3 mM KKKVSRSGLYRSPSMPENLNRPR, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

110. CLK2 Assay

CLK2 (5-20 mU diluted in 50 mM Tris pH 7.5, 0.1 mM EGTA, 1 mg/ml BSA) is assayed against a substrate peptide (RNRYRDVSPFDHSR) in a final volume of 25.5 µl containing 50 mM Tris pH 7.5, 0.3 mM peptide, 10 mM DTT, 10 mM magnesium acetate and 0.005 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

111. DAPK1 Assay

DAPK1 (5-20 mU diluted in 50 mM Tris pH 7.5, 0.1 mM EGTA, 1 mg/ml BSA) is assayed against a substrate peptide KKLNRTLSFAEPG) in a final volume of 25.5 µl containing 50 mM Tris pH 7.5, 0.3 mM peptide, 10 mM DTT, 10 mM magnesium acetate and 0.005 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

112. EPH-B2 Assay

EPH-B2 (5-20 mU diluted in 50 mM Tris pH 7.5, 0.1 mM EGTA, 1 mg/ml BSA) is assayed against a substrate peptide (Poly Glut Tyr) in a final volume of 25.5 µl containing 50 mM Tris pH 7.5, 1 mg/ml substrate peptide, 10 mM magnesium acetate and 0.02 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

113. TSSK1 Assay

TSSK1 (5-20 mU diluted in 50 mM Tris pH 7.5, 0.1 mM EGTA, 0.1% β-mercaptoethanol, 1 mg/ml BSA, 10 mM DTT) is assayed against KKKVSRSGLYR-SPSMPENLNRPR in a final volume of 25.5 µl containing 50 mM Tris pH 7.5, 0.1 mM EGTA, 0.3 mM KKKVSRSG-LYRSPSMPENLNRPR, 10 mM magnesium acetate and 0.02 mM [33P-γ-ATP](50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

114. TESK1 Assay

TESK1 (5-20 mU diluted in 50 mM Tris pH 7.5, 0.1 mM EGTA, 0.1% β-mercaptoethanol, 1 mg/ml BSA, 10 MM DTT) is assayed against Cofilin 2 in a final volume of 25.5 µl containing 50 mM Tris pH 7.5, 0.1 mM EGTA, 0.2 mg/ml Cofilin 2, 10 mM magnesium acetate and 0.05 mM [33P-γ-ATP] (50-1000 cpm/pmole) and incubated for 30 min at room temperature. Assays are stopped by addition of 5 µl of 0.5 M (3%) orthophosphoric acid and then harvested onto P81 Unifilter plates with a wash buffer of 50 mM orthophosphoric acid.

115. TTBK1 Assay

TTBK1 (5-20 mU diluted in 50 mM Tris pH 7.5, 0.1 mM EGTA, 0.1% β-mercaptoethanol, 1 mg/ml BSA, 10 mM DTT) is assayed against RRKDLHDDEEDEAMSITA in a final volume of 25.5 µl containing 50 mM Tris pH 7.5, 0.1 mM EGTA, 0.3 mM RRKDLHDDEEDEAMSITA, 10 mM magnesium acetate and 0.005 mM [33P-γ-ATP] (50-1000 cpm/pmole) and incubated for 30 min at room temperature. Assays are stopped by addition of 5 µl of 0.5 M (3%)

orthophosphoric acid and then harvested onto P81 Unifilter plates with a wash buffer of 50 mM orthophosphoric acid.

LRRK2 Potency

The $IC_{50}$ values for inhibition of LRRK2 G2019S with Examples in this invention are illustrated in the table below.

TABLE

| LRRK2_$IC_{50}$ values of Examples | | | |
|---|---|---|---|
| Example | $IC_{50}$ (nM) | Example | $IC_{50}$ (nM) |
| 16 | 3000 | 45 | 71 |
| 17 | 810 | 46 | 49 |
| 19 | 230 | 47 | 54 |
| 20 | 450 | 48 | 68 |
| 22 | 140 | 49 | 67 |
| 23 | 150 | 50 | 120 |
| 25 | 3600 | 51 | 39 |
| 26 | 91 | 52 | 33 |
| 28 | 570 | 53 | 33 |
| 29 | 150 | 54 | 6400 |
| 30 | 250 | 55 | 50 |
| 31 | 110 | 56 | 58 |
| 32 | 34 | 57 | 260 |
| 33 | 30 | 58 | 74 |
| 34 | 41 | 59 | 46 |
| 35 | 75 | 60 | 47 |
| 37 | 20 | 61 | 57 |
| 38 | 180 | 65 | 4 |
| 40 | 140 | 66 | 26 |
| 42 | 31 | 67 | 7 |
| 44 | 48 | 82 | 39 |
| 70 | 23 | 83 | 23 |
| 71 | 11 | 85 | 50 |
| 72 | 15 | 86 | 29 |
| 73 | 21 | 87 | 62 |
| 74 | 50 | 88 | 31 |
| 75 | 16 | 89 | 49 |
| 68 | 34 | 90 | 12 |
| 81 | 40 | 91 | 6 |
| 84 | 46 | 92 | 13 |
| 93 | 170 | 94 | 820 |

JAK2 Selectivity

The JAK2 $IC_{50}$ values for Examples in this invention are illustrated in the table below.

TABLE

| JAK2_$IC_{50}$ values of Examples | | | |
|---|---|---|---|
| Example | $IC_{50}$ (nM) | Example | $IC_{50}$ (nM) |
| 19 | 3100 | 47 | 2200 |
| 22 | 8400 | 48 | 550 |
| 23 | 6600 | 51 | 580 |
| 29 | 17000 | 56 | 4800 |
| 45 | 2100 | 58 | 840 |
| 46 | 1900 | 61 | 900 |
| 71 | 920 | 83 | 4500 |
| 72 | 660 | 85 | 5400 |
| 73 | 1500 | 86 | 3000 |
| 74 | 2400 | 89 | 23000 |
| 75 | 2100 | 90 | 890 |
| 68 | 6300 | 91 | 1700 |
| 81 | 4600 | 92 | 13000 |
| 84 | 9900 | 93 | >30000 |
| 88 | 5400 | | |

Potency in *Drosophila* Model

Survival Rate

The survival rate for Examples in this invention are illustrated in the table below.

| Example | Survival Rate |
|---|---|
| 29 | * |
| 58 | ** |

** P < 0.01, compared to DMSO negative control;

* P < 0.05, compared to DMSO negative control.

Climbing Assay

The climbing assay for Examples in this invention are illustrated in the table below.

| | Climbing Assay | | | |
|---|---|---|---|---|
| Example | 3 weeks | 4 weeks | 5 weeks | 6 weeks |
| 29 | * | ** | * | * |
| 58 | * | * | ** | ** |

** P < 0.01, compared to DMSO negative control;

* P < 0.05, compared to DMSO negative control;

Kinase Assays at Week 6

The kinase assays for Examples in this invention are illustrated in the table below.

| Example | Kinase Assays |
|---|---|
| 29 | * |
| 58 | * |
| 44 | * |

* P < 0.05, compared to DMSO negative control.

Kinase Selectivity Data

Kinase selectivity data of representative compounds are shown in the table below. Values are expressed as percentage inhibition of the each specific kinase at 1 µM inhibitor concentration.

TABLE

Kinase selectivity data of representative compounds

| Kinase | Ex. 29 | Ex. 22 | Ex. 23 | Ex. 55 | Ex. 68 | Kinase | Ex. 29 | Ex. 22 | Ex. 23 | Ex. 55 | Ex. 68 |
|---|---|---|---|---|---|---|---|---|---|---|---|
| MKK1 | 21 | 15 | 0 | 65 | 31 | CK2 | 0 | 0 | 0 | 11 | 4 |
| ERK1 | 0 | 0 | 0 | 4 | 11 | DYRK1A | 4 | 16 | 0 | 8 | 0 |
| ERK2 | 0 | 0 | 0 | 0 | 11 | NEK2a | 0 | 13 | 8 | 14 | 0 |
| JNK1 | 0 | 0 | 0 | 49 | 48 | NEK6 | 1 | 3 | 1 | 0 | 0 |
| JNK2 | 0 | 1 | 0 | 41 | 37 | IKKb | 0 | 2 | 0 | 6 | 4 |
| p38aMAPK | 0 | 4 | 0 | 6 | 0 | IKKe | 9 | 0 | 0 | 5 | 0 |
| RSK1 | 10 | 0 | 0 | 41 | 69 | TBK1 | 0 | 0 | 0 | 5 | 5 |
| RSK2 | 0 | 8 | 5 | 21 | 54 | PIM1 | 0 | 0 | 0 | 26 | 77 |
| PDK1 | 2 | 7 | 0 | 42 | 21 | SRPK1 | 0 | 0 | 0 | 0 | 0 |
| PKBa | 0 | 3 | 0 | 1 | 0 | EF2K | 0 | 0 | 0 | 1 | 1 |
| PKBb | 0 | 0 | 0 | 10 | 9 | HIPK2 | 3 | 11 | 3 | 1 | 0 |
| SGK1 | 18 | 13 | 0 | 10 | 23 | PAK4 | 7 | 6 | 0 | 20 | 25 |
| S6K1 | 2 | 0 | 0 | 17 | 0 | MST2 | 10 | 20 | 0 | 28 | 2 |
| PKA | 0 | 0 | 0 | 0 | 0 | MST4 | 1 | 6 | 0 | 0 | 0 |
| ROCK2 | 11 | 5 | 0 | 14 | 21 | GCK | 67 | 56 | 41 | 71 | 27 |
| PRK2 | 0 | 2 | 0 | 0 | 8 | MINK1 | 0 | 0 | 0 | 12 | 7 |
| PKCa | 11 | 0 | 0 | 0 | 2 | MEKK1 | 0 | 0 | 0 | 5 | 0 |
| PKCz | 0 | 0 | 0 | 0 | 1 | MLK1 | 0 | 0 | 0 | 24 | 12 |
| PKD1 | 3 | 20 | 9 | 73 | 46 | MLK3 | 8 | 7 | 4 | 6 | 4 |
| MSK1 | 7 | 2 | 2 | 34 | 30 | TAK1 | 65 | 64 | 49 | 64 | 36 |
| MNK1 | 0 | 0 | 0 | 50 | 1 | IRAK4 | 15 | 13 | 0 | 9 | 14 |
| MNK2 | 0 | 0 | 0 | 40 | 18 | RIPK2 | 0 | 0 | 0 | 7 | 0 |
| PRAK | 0 | 0 | 0 | 18 | 13 | TTK | 2 | 0 | 0 | 35 | 2 |
| CAMKKb | 0 | 5 | 7 | 0 | 0 | ULK1 | 5 | 14 | 0 | 20 | 30 |
| CAMK1 | 0 | 0 | 0 | 25 | 45 | ULK2 | 7 | 12 | 1 | 31 | 10 |
| SmMLCK | 11 | 16 | 15 | 16 | 9 | Src | 0 | 13 | 0 | 1 | 0 |
| PHK | 35 | 41 | 18 | 73 | 43 | Lck | 0 | 0 | 0 | 6 | 0 |
| CHK1 | 0 | 2 | 0 | 42 | 28 | CSK | 0 | 1 | 0 | 0 | 0 |
| CHK2 | 2 | 11 | 0 | 80 | 53 | YES1 | 0 | 0 | 0 | 16 | 5 |
| GSK3b | 0 | 16 | 0 | 0 | 0 | BTK | 0 | 0 | 0 | 0 | 0 |
| CDK2-CyclinA | 30 | 16 | 0 | 10 | 0 | JAK2 | 16 | 5 | 12 | \ | \ |
| PLK1 | 0 | 4 | 3 | 28 | 21 | SYK | 0 | 0 | 0 | 0 | 1 |
| AuroraA | 0 | 0 | 0 | 9 | 13 | EPH-A2 | 0 | 0 | 0 | 0 | 0 |
| AuroraB | 29 | 23 | 1 | 38 | 19 | EPH-B3 | 0 | 0 | 0 | 12 | 5 |
| LKB1 | 6 | 20 | 16 | 0 | 0 | FGF-R1 | 12 | 11 | 19 | 9 | 35 |
| AMPK(hum) | 6 | 16 | 8 | 64 | 32 | HER4 | 10 | 8 | 3 | 0 | 1 |
| MARK3 | 13 | 1 | 0 | 47 | 43 | IGF-1R | 9 | 9 | 2 | 8 | 0 |
| BRSK2 | 2 | 0 | 0 | 50 | 31 | IR | 2 | 27 | 1 | 5 | 0 |
| MELK | 24 | 10 | 1 | 78 | 72 | IRR | 6 | 8 | 4 | 18 | 1 |
| NUAK1 | 7 | 8 | 17 | 76 | 65 | TrkA | 20 | 0 | 0 | 5 | 9 |
| CK1δ | 11 | 0 | 0 | 12 | 3 | VEG-FR | 9 | 0 | 6 | 19 | 42 |

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

1. Lees A J, Hardy J, Revesz T (2009) Parkinson's disease. Lancet 373: 2055-2066.
2. Nalls M A, Pankratz N, Lill C M, Do C B, Hernandez D G et al. (2014) Large-scale meta-analysis of genome-wide association data identifies six new risk loci for Parkinson's disease. Nat Genet 46: 989-993.
3. Simon-Sanchez J, Schulte C, Bras J M, Sharma M, Gibbs J R, et al. (2009) Genome-wide association study reveals genetic risk underlying Parkinson's disease. Nat Genet 41: 1308-1312.
4. Satake W, Nakabayashi Y, Mizuta I, Hirota Y, Ito C, et al. (2009) Genome-wide association study identifies common variants at four loci as genetic risk factors for Parkinson's disease. Nat Genet 41: 1303-1307.
5. Rudenko I N, Cookson M R (2014) Heterogeneity of leucine-rich repeat kinase 2 mutations: genetics, mechanisms and therapeutic implications. Neurotherapeutics 11: 738-750.
6. Fonzo A, Wu-Chou Y-H, Lu C-S, Doeselaar M, Simons E J, et al. (2006) A common missense variant in the LRRK2 gene, Gly2385Arg, associated with Parkinson's disease risk in Taiwan. Neurogenetics 7: 133-138.
7. Farrer M J, Stone J T, Lin C H, Dachsel J C, Hulihan M M, et al. (2007) Lrrk2 G2385R is an ancestral risk factor for Parkinson's disease in Asia. Parkinsonism Relat Disord 13: 89-92.
8. West A B, Moore D J, Biskup S, Bugayenko A, Smith W W, et al. (2005) From The Cover: Parkinson's disease-associated mutations in leucine-rich repeat kinase 2 augment kinase activity. Proceedings of the National Academy of Sciences 102: 16842-16847.
9. Khan N L, Jain S, Lynch J M, Pavese N, Abou-Sleiman P, et al. (2005) Mutations in the gene LRRK2 encoding dardarin (PARK8) cause familial Parkinson's disease: clinical, pathological, olfactory and functional imaging and genetic data. Brain.
10. Kachergus J, Mata I F, Hulihan M, Taylor J P, Lincoln S, et al. (2005) Identification of a Novel LRRK2 Mutation Linked to Autosomal Dominant Parkinsonism: Evidence of a Common Founder across European Populations. The American Journal of Human Genetics 76: 672-680.
11. Ozelius L J, Senthil Q Saunders-Pullman R, Ohmann E, Deligtisch A, et al. (2006) LRRK2 G2019S as a Cause of Parkinson's Disease in Ashkenazi Jews. New England Journal of Medicine 354: 424-425.
12. Jaleel M, Nichols R J, Deak M, Campbell David Q Gillardon F, et al. (2007) LRRK2 phosphorylates moesin at threonine-558: characterization of how Parkinson's disease mutants affect kinase activity. Biochemical Journal 405: 307-317.
13. Ishihara L, Gibson R A, Warren L, Amouri R, Lyons K, et al. (2007) Screening for Lrrk2 G2019S and clinical comparison of Tunisian and North American Caucasian Parkinson's disease families. Movement Disorders 22: 55-61.
14. Tan, E. K. (2006) Identification of a common genetic risk variant (LRRK2 Gly2385Arg) in Parkinson's disease. Ann Acad Med Singapore. 35: 840-842.
15. Ross O A, Wu Y-R, Lee M-C, Funayama M, Chen M-L, et al. (2008) Analysis of Lrrk2 R1628P as a risk factor for Parkinson's disease. Annals of Neurology 64: 88-92.
16. Ross O A, Soto-Ortolaza A I, Heckman M Q Aasly J O, Abahuni N, et al. (2011) Association of LRRK2 exonic variants with susceptibility to Parkinson's disease: a case-control study. The Lancet Neurology 10: 898-908.
17. Paisan-Ruiz C, Jain S, Evans E W, Gilks W P, Simón J, et al. (2004) Cloning of the Gene Containing Mutations that Cause PARK8-Linked Parkinson's Disease. Neuron 44: 595-600.
18. Zimprich A, Biskup S, Leitner P, Lichtner P, Farrer M, et al. (2004) Mutations in LRRK2 Cause Autosomal-Dominant Parkinsonism with Pleomorphic Pathology. Neuron 44: 601-607.
19. Agalliu I, San Luciano M, Mirelman A, et al. (2015) Higher frequency of certain cancers in lrrk2 g2019s mutation carriers with parkinson disease: A pooled analysis. JAMA Neurology 72: 58-65.
20. Singleton A B, Farrer M J, Bonifati V (2013) The genetics of Parkinson's disease: Progress and therapeutic implications. Movement Disorders 28: 14-23.
21. Jostins L, Ripke S, Weersma R K, Duerr R H, McGovern D P, et al. (2012) Host-microbe interactions have shaped the genetic architecture of inflammatory bowel disease. Nature 491: 119-124.
22. Marcinek P, Jha A N, Shinde V, Sundaramoorthy A, Rajkumar R, et al. (2013) LRRK2 and RIPK2 Variants in the NOD 2-Mediated Signaling Pathway Are Associated with Susceptibility to *Mycobacterium leprae* in Indian Populations. Plos One 8: e73103.
23. Marin I (2006) The Parkinson Disease Gene LRRK2: Evolutionary and Structural Insights. Molecular Biology and Evolution 23: 2423-2433.
24. Rudenko I N, Kaganovich A, Hauser D N, Beylina A, Chia R, et al. (2012) The G2385R variant of leucine-rich repeat kinase 2 associated with Parkinson's disease is a partial loss-of-function mutation. Biochemical Journal 446: 99-111.
25. Mata I F, Wedemeyer W J, Farrer M J, Taylor J P, Gallo K A (2006) LRRK2 in Parkinson's disease: protein domains and functional insights. Trends in Neurosciences 29: 286-293.
26. Taylor J P, Mata I F, Farrer M J (2006) LRRK2: a common pathway for parkinsonism, pathogenesis and prevention? Trends in Molecular Medicine 12: 76-82.
27. Greggio E, Jain S, Kingsbury A, Bandopadhyay R, Lewis P, et al. (2006) Kinase activity is required for the toxic effects of mutant LRRK2/dardarin. Neurobiology of Disease 23: 329-341.
28. Heo H Y, Park J-M, Kim C-H, Han B S, Kim K-S, et al. (2010) LRRK2 enhances oxidative stress-induced neurotoxicity via its kinase activity. Experimental Cell Research 316: 649-656.
29. Reinhardt P, Schmid B, Burbulla Lena F, Schondorf David C, Wagner L, et al. (2013) Genetic Correction of a LRRK2 Mutation in Human iPSCs Links Parkinsonian Neurodegeneration to ERK-Dependent Changes in Gene Expression. Cell Stem Cell 12: 354-367.
30. Sanders L H, Laganiere J, Cooper O, Mak S K, Vu B J, et al. (2014) LRRK2 mutations cause mitochondrial DNA damage in iPSC-derived neural cells from Parkinson's disease patients: Reversal by gene correction. Neurobiology of Disease 62: 381-386.
31. Manzoni C, Lewis P A (2013) Dysfunction of the autophagy/lysosomal degradation pathway is a shared feature of the genetic synucleinopathies. The FASEB Journal 27: 3424-3429.
32. Orenstein S J, Kuo S-H, Tasset I, Arias E, Koga H, et al. (2013) Interplay of LRRK2 with chaperone-mediated autophagy. Nat Neurosci 16: 394-406.
33. Manzoni C, Mamais A, Dihanich S, Abeti R, Soutar MPM, et al. (2013) Inhibition of LRRK2 kinase activity stimulates macroautophagy. Biochimica et Biophysica Acta (BBA)—Molecular Cell Research 1833: 2900-2910.
34. Swan M, Saunders-Pullman R (2013) The Association Between 1-Glucocerebrosidase Mutations and Parkinsonism. Current Neurology and Neuroscience Reports 13: 1-10.
35. Li L, Zhang X, Le W (2010) Autophagy Dysfunction in Alzheimer's Disease. Neurodegenerative Diseases 7: 265-271.
36. Nixon R A (2013) The role of autophagy in neurodegenerative disease. Nat Med 19: 983-997.
37. Westbroek W, Gustafson A M, Sidransky E (2011) Exploring the link between glucocerebrosidase mutations and parkinsonism. Trends in Molecular Medicine 17: 485-493.
38. Reddy J V, Ganley I G Pfeffer S R (2006) Clues to Neuro-Degeneration in Niemann-Pick Type C Disease from Global Gene Expression Profiling. Plos One 1: e19.—supporting information Dataset S1
39. Kawakami F, Yabata T, Ohta E, Maekawa T, Shimada N, et al. (2012) LRRK2 Phosphorylates Tubulin-Associated Tau but Not the Free Molecule: LRRK2-Mediated Regulation of the Tau-Tubulin Association and Neurite Outgrowth. Plos One 7: e30834.
40. Taymans J-M, Cookson M R (2010) Mechanisms in dominant parkinsonism: The toxic triangle of LRRK2, α-synuclein, and tau. BioEssays 32: 227-235.
41. Bailey R M, Covy J P, Melrose H L, Rousseau L, Watkinson R, et al. (2013) LRRK2 phosphorylates novel tau epitopes and promotes tauopathy. Acta Neuropathologica 126: 809-827.
42. Li Y, Liu W, Oo T F, Wang L, Tang Y, et al. (2009) Mutant LRRK2R1441G BAC transgenic mice recapitulate cardinal features of Parkinson's disease. Nat Neurosci 12: 826-828.
43. Goedert M, Jakes R (2005) Mutations causing neurodegenerative tauopathies. Biochimica et Biophysica Acta (BBA)—Molecular Basis of Disease 1739: 240-250.
44. Rothman R B, Blough B E, Baumann M H (2008) Dopamine/serotonin releasers as medications for stimulant addictions. In: Giuseppe Di Giovann V D M, Ennio E, editors. Progress in Brain Research: Elsevier. pp. 385-406.

45. Brand A H, Perrimon N (1993) Targeted gene expression as a means of altering cell fates and generating dominant phenotypes. Development 118: 401-415.

46. Liu Z, Wang X, Yu Y, Li X, Wang T, et al. (2008) A Drosophila model for LRRK2-linked parkinsonism. Proceedings of the National Academy of Sciences 105: 2693-2698.

47. Liu Z, Hamamichi S, Dae Lee B, Yang D, Ray A, et al. (2011) Inhibitors of LRRK2 kinase attenuate neurodegeneration and Parkinson-like phenotypes in *Caenorhabditis elegans* and *Drosophila* Parkinson's disease models. Human Molecular Genetics 20: 3933-3942.

What is claimed is:

1. A compound of formula I, or a stereoisomer, a tautomer, an N-oxide, a hydrate, a solvate, or a pharmaceutically acceptable salt thereof:

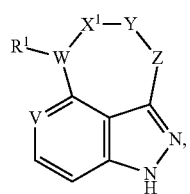

(I)

wherein:
V is N;
W is N;
$R^1$ is selected from the following groups:

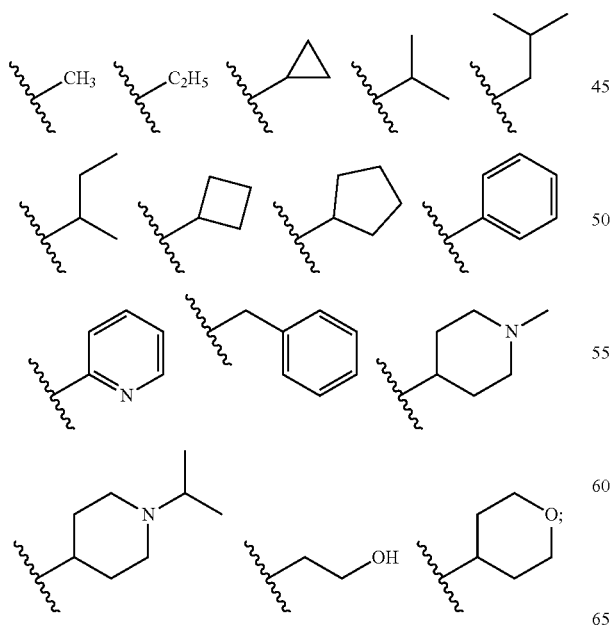

$X^1$ is CO or $-(CH_2)_n-$;
Y is

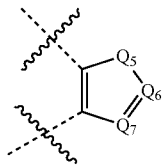

wherein
$Q_5$ is N optionally substituted with one or more substituents chosen from $C_{1-6}$ alkyl, $C_{3-7}$ cycloalkyl, $C_{3-7}$ heterocycloalkyl, F, Cl, Br, I, $-NO_2$, $-CN$, $-N_3$, $-NH_2$, $-OH$ or $C_{1-6}$ haloalkyl;
$Q_6$ is N;
$Q_7$ is CH;
Z is a bond;
n is 1;
$R^2$ and $R^3$ are independently selected from $-H$, $C_{1-6}$ alkyl, $C_{3-7}$ cycloalkyl, $C_{2-7}$ heterocycloalkyl, $C_{6-14}$ aryl or $C_{1-10}$ heteroaryl, wherein each of said $C_{1-6}$ alkyl, $C_{3-7}$ cycloalkyl, $C_{2-7}$ heterocycloalkyl, $C_{6-14}$ aryl and $C_{1-10}$ heteroaryl is optionally and independently substituted with one or more substituents chosen from F, Cl, Br, I, $-NO_2$, $-CN$, $-N_3$, $-NH_2$, $-OH$, and $-CO_2H$.

2. The compound according to claim 1, wherein $X^1$ is CO.

3. The compound according to claim 1 having one of the following structures or a stereoisomer, a tautomer, an N-oxide, a hydrate, a solvate or a pharmaceutically acceptable salt thereof:

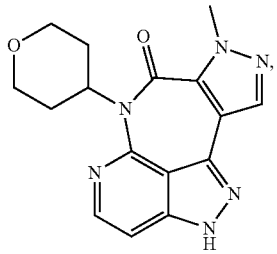

67

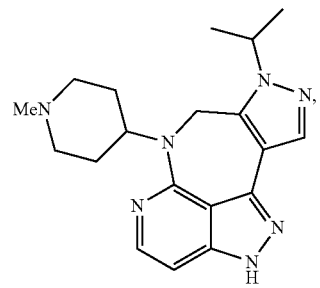

68

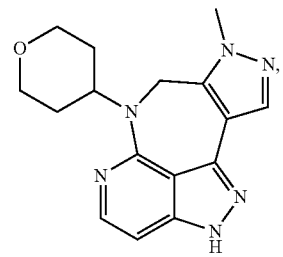

71

73

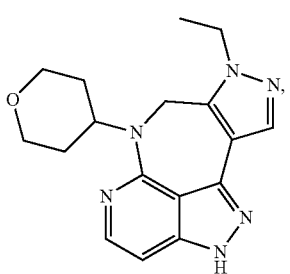

75

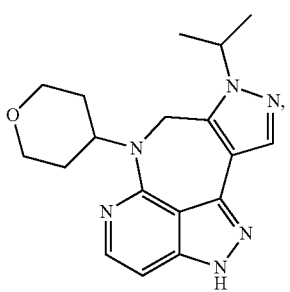 [SMILES: CC(C)n1ncc2c1CN(C1CCOCC1)c1nccc3[nH]nc-2c13]

80

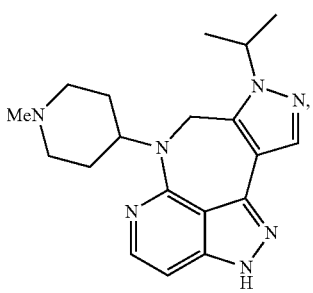

83

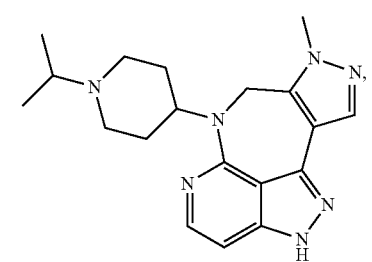

85

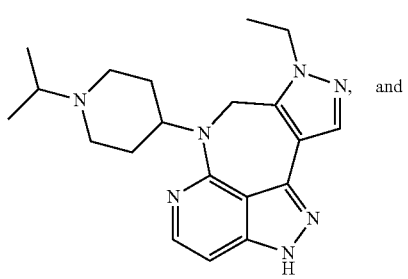

and

87

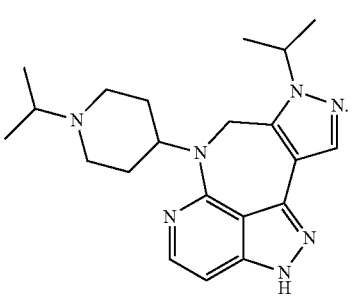

4. A pharmaceutical composition comprising the compound of claim 1 and a pharmaceutically acceptable carrier, diluent, excipient or a combination thereof.

5. The compound according to claim 1, wherein $R^1$ is selected from the following groups:

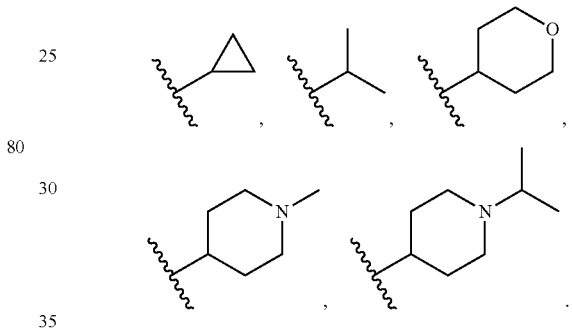

6. The compound of claim 1 having one of the following structures or a stereoisomer, a tautomer, an N-oxide, a hydrate, a solvate or a pharmaceutically acceptable salt thereof:

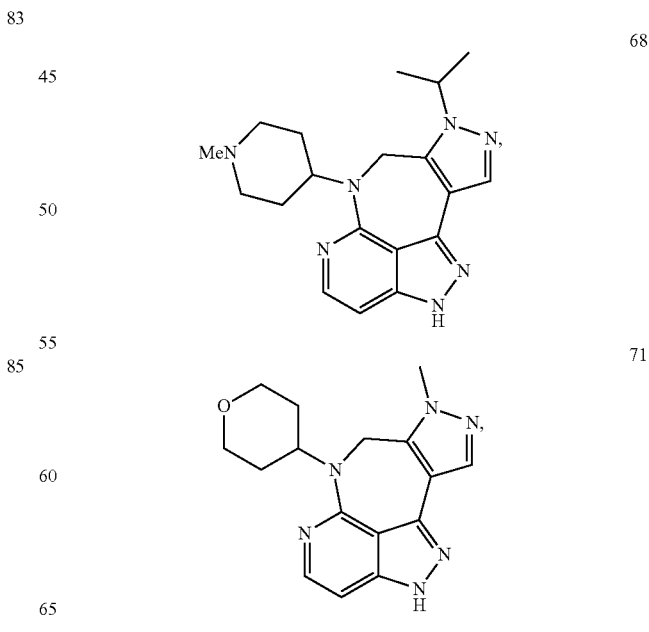

-continued
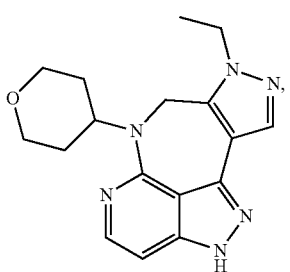
73
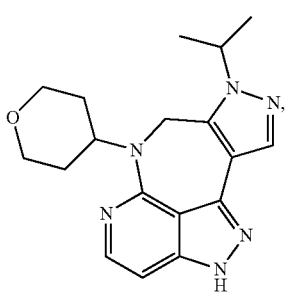
75
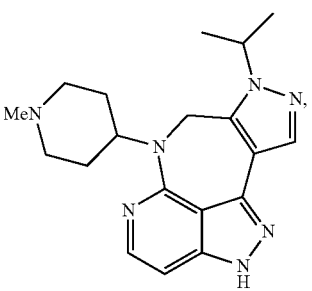
80
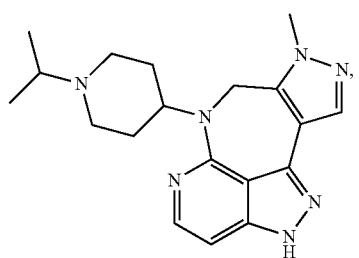
83
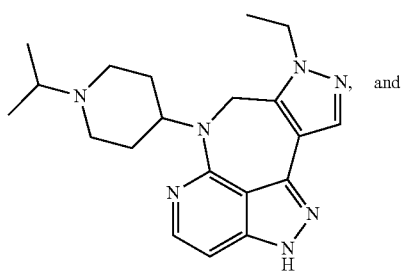
85
-continued
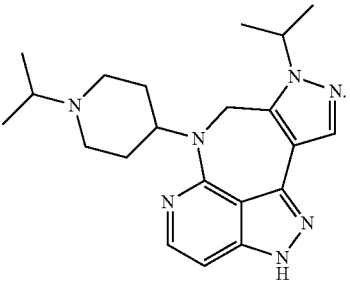
87
7. A compound that is
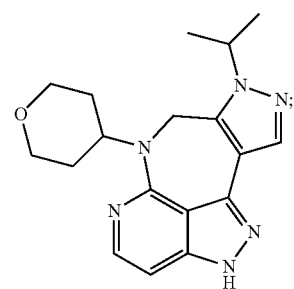
or a stereoisomer, a tautomer, an N-oxide, a hydrate, a solvate or a pharmaceutically acceptable salt thereof.
8. The compound according to claim 1, wherein $X^1$ is —CH$_2$—.
9. A compound selected from the group consisting of
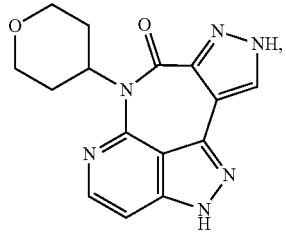
65
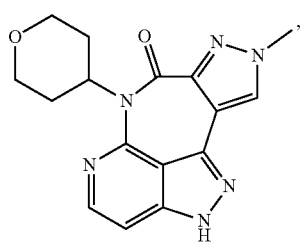
66
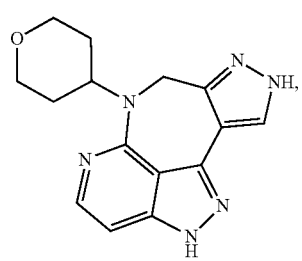
69

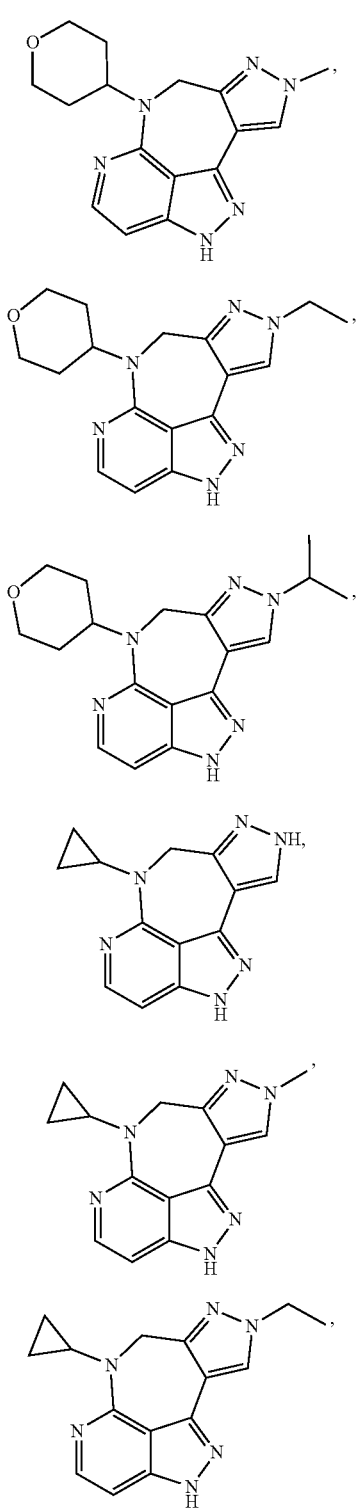
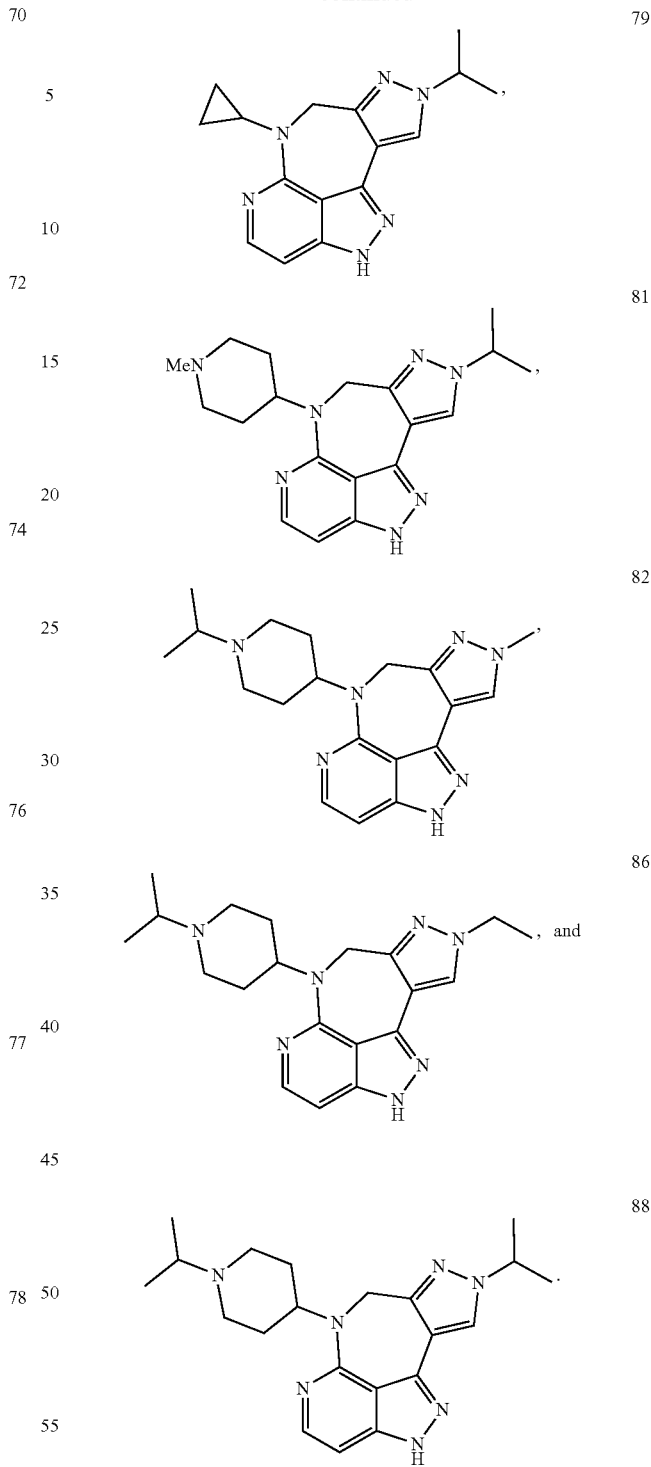
* * * * *